US008008280B2

(12) United States Patent
Saxena et al.

(10) Patent No.: US 8,008,280 B2
(45) Date of Patent: Aug. 30, 2011

(54) BETULINOL DERIVATIVES AS ANTI-HIV AGENTS

(75) Inventors: Brij B. Saxena, Englewood, NJ (US); Premila Rathnam, Englewood Cliffs, NJ (US)

(73) Assignee: Biorings LLC, New York, NY (US)

( * ) Notice: Subject to any disclaimer, the term of this patent is extended or adjusted under 35 U.S.C. 154(b) by 492 days.

(21) Appl. No.: 11/662,433

(22) PCT Filed: Sep. 12, 2005

(86) PCT No.: PCT/US2005/032363
§ 371 (c)(1),
(2), (4) Date: Jul. 17, 2008

(87) PCT Pub. No.: WO2006/031706
PCT Pub. Date: Mar. 23, 2006

(65) Prior Publication Data
US 2008/0286291 A1 Nov. 20, 2008

Related U.S. Application Data

(60) Provisional application No. 60/609,080, filed on Sep. 10, 2004, provisional application No. 60/630,103, filed on Nov. 22, 2004, provisional application No. 60/630,150, filed on Nov. 22, 2004.

(51) Int. Cl.
*A01N 45/00* (2006.01)
*A01N 37/08* (2006.01)
*A61K 31/56* (2006.01)
*A61K 31/215* (2006.01)

(52) U.S. Cl. ........................... 514/169; 514/530

(58) Field of Classification Search .............. 514/169, 514/530
See application file for complete search history.

(56) References Cited

U.S. PATENT DOCUMENTS

| | | | |
|---|---|---|---|
| 4,127,124 | A | 11/1978 | Clagett et al. |
| 4,350,683 | A | 9/1982 | Galfre et al. |
| 4,363,799 | A | 12/1982 | Kung et al. |
| 4,381,292 | A | 4/1983 | Bieber et al. |
| 4,423,147 | A | 12/1983 | Secher et al. |
| 5,468,888 | A | 11/1995 | Bouboutou et al. |
| 5,697,828 | A | 12/1997 | Smathers et al. |
| 5,750,578 | A | 5/1998 | Carlson et al. |
| 5,869,535 | A | 2/1999 | Pezzuto et al. |
| 6,048,847 | A | 4/2000 | Ramadoss et al. |
| 6,172,110 | B1 | 1/2001 | Lee et al. |
| 6,214,350 | B1 | 4/2001 | Hwang |
| 6,225,353 | B1 | 5/2001 | Pezzuto et al. |
| 6,403,816 | B1 | 6/2002 | Jaggi et al. |
| 6,495,600 | B1 | 12/2002 | Pezzuto |
| 6,569,842 | B2 | 5/2003 | Pezzuto et al. |
| 6,890,533 | B2 | 5/2005 | Bomshteyn et al. |
| 7,026,305 | B2 | 4/2006 | Chen et al. |
| 2002/0119935 | A1 | 8/2002 | Krasutsky et al. |
| 2003/0166507 | A1 | 9/2003 | Li et al. |

FOREIGN PATENT DOCUMENTS

| | | |
|---|---|---|
| WO | WO 94/26725 | 11/1994 |
| WO | WO-96/39033 | 12/1996 |
| WO | WO 02/16395 | 2/2002 |
| WO | WO 02/091858 | 11/2002 |
| WO | WO 2005/112929 | 12/2005 |

OTHER PUBLICATIONS

BMJ (2002) 324:235-241.*
Flekhter et al., "Synthesis and Antiviral Activity of Betulonic Acid Amides and Conjugates with Amino Acids", Russian Journal of Bioorganic Chemistry, 30:80-88 (2004).
Wermuth, "The Practice of Medicinal Chemistry, Passage", Practice of Medicinal Chemistry, pp. 756-776 (1996).
Search and Communication from European Patent Office concerning corresponding European application.
"Betulinic Acid Derviatives in AIDS," *Marketletter UK,* Article No. 941623800 (May 2, 1994).
Ahmad, Chemical Examination of *Scirpus tuberosus* (Cyperacaeae), *J. Indian Chem. Soc.,* 61:92-93 (1964).
De Clercq et al., "Current lead natural products for the chemotherapy of human immunodeficiency virus (HIV) infection," *Medicinal Research Reviews,* 20:323-349 (2000).
Evers et al., "Betulinic acid derivatives: a new class of human immunodeficiency virus type 1 specific inhibitors with a new mode of action," *J. Med. Chem.,* 39:1056-1068 (1996).
Flekhter et al., "Synthesis and pharmacological activity of betulin dinicotinate," *Bioorg. Khim.,* 28:543-550 (2002).
Hashimoto et al., "Anti-AIDS agents—27. Synthesis and anti-HIV activity of betulinic acid and dihydrobetulinic acid derivatives," *Bioorg. Med. Chem.,* 5:2133-2143 (1997).
Hiroya et al., "Synthesis of betulin derivatives and their protective effects against the cytotoxicity of cadmium," *Bioorg. Med. Chem.,* 10:3229-3236 (2002).
International Search Report of International Application No. PCT/US05/32363 (dated Jul. 26, 2006).
Ito et al., "Anti-AIDS Agents. 48. Anti-HIV activity of moronic acid cerivatives and the new melliferone-related triterpenoid isolated from brazilian propolis," *Journal of Natural Products,* 64:1278-1281 (2001).
Karam et al., "Human CYP2C19 is a major omeprazole 5-hydroxylase, as demonstrated with recombinant cytochrome P450 enzymes," *Drug Metab. Dispos.,* 24:1081-1087 (1996).

(Continued)

*Primary Examiner* — Marcos L Sznaidman
(74) *Attorney, Agent, or Firm* — Stroock & Stroock & Lavan LLP

(57) ABSTRACT

The present invention relates to methods of treating HIV-1 infection in a subject. These methods involve administering to the subject with HIV-1 infection a therapeutically effective amount of a conjugated or immunoconjugated betulinol derivative compound, or a pharmaceutically acceptable salt or derivative thereof, under conditions effective to treat the subject for HIV-1 infection. Also disclosed are methods inhibiting HIV-1 activity in a cell. These methods involve providing a cell infected with HIV-1 and contacting the cell with a conjugated or immunoconjugated betulinol derivative compound, or a pharmaceutically acceptable salt or derivative thereof, under conditions effective to inhibit HIV-1 activity in the cell.

9 Claims, 19 Drawing Sheets

OTHER PUBLICATIONS

Kashiwada et al., "3,28-Di-O-(dimethylsuccinyl)-betulin isomers as anti-HIV agents," *Bioorg. Med. Chem. Lett.*, 11:183-185 (2001).

Kashiwada et al., "Betulinic acid and dihydrobetulinic acid derivatives as potent anti-HIV agents," *J. Med. Chem.*, 39:1016-1017 (1996).

Kim et al., "A concise semi-synthetic approach to betulinic acid from betulin," *Synthetic Communications*, 27:1607-1612 (1997).

Kim et al., "Synthesis of betulinic acid derivatives with activity against human melanoma," *Bioorg. Med. Chem. Lett.*, 8:1707-1712 (1998).

Komissarova et al., "Selective oxidation of betulin by Cr(VI) reagents," *Chemistry of Natural Compounds*, 38:58-61 (2002).

Sheth et al., "Antitumor agents from alnus oregona (betulaceae)," *J. Pharm. Sci.*, 62:139-140 (1973).

Sheth et al., "Tumor-inhibitory agent from hyptis emoryi (labiatae)," *J. Pharm. Sci.*, 61:1819 (1972).

Soler et al., "Betulinic acid derivatives: A new class of specific inhibitors of human immunodeficiency virus type 1 entry," *J. Med. Chem.*, 39:1069-1083 (1996).

Sun et al., "Anti-AIDS agents 49. Synthesis, anti-HIV, and anti-fusion activities of IC9564 analogues based on betulinic acid," *J. Med. Chem.*, 45:4271-4275 (2002).

Sun et al., "Anti-AIDS agents. 34. Synthesis and structure-activity relationships of betulin derivatives as anti-HIV agents," *J. Med. Chem.* 5:4648-4657 (1998).

Tomas-Barberan et al., "A cytotoxic triterpenoid and flavonoids from crossopteryx febrifuga," *Planta Med.*, 54:266-267 (1988).

Ukkonen, *Birch Bark Extractive Kemia Kemi*, 6:217 (1979).

Vlietinck et al., "Plant-derived leading comopunds for chemotherapy of human immunodeficiency virus (HIV) infection," *Planta Med.*, 64:97-109 (1998).

Written Opinion of the International Searching Authority of International Application No. PCT/US05/32363 (dated May 31, 2006).

* cited by examiner

| TUBE | CONDITION | 1 OD450 ON DAY 8 | 2 OD450 ON DAY 5 | AVERAGE | S.D. | INHIBITION |
|---|---|---|---|---|---|---|
| 1 | MT-2 NO INFECTION | 0.076 | 0.089 | 0.083 | 0.0092 | |
| 2 | MT-2 964A NO DRUG | 0.804 | 0.586 | 0.695 | 0.1541 | |
| 3 | MT-2 964A AZT 2µM | 0.570 | 0.475 | 0.523 | 0.0672 | 25% |
| 4 | MT-2 964A BA 2µM | 0.717 | 0.673 | 0.695 | 0.0311 | 0% |
| 7 | MT-2 964B NO DRUG | 0.633 | 0.718 | 0.676 | 0.0601 | |
| 8 | MT-2 964B AZT 2µM | 0.676 | 0.755 | 0.716 | 0.0559 | -6% |
| 9 | MT-2 964B BA 2µM | 0.345 | 0.407 | 0.376 | 0.0438 | 44% |

NOTES:
2.5 x 10-4 MT-2 CELLS PER WELL OF 96 WELL PLATE,
p24 CAPTURE ASSAY ON DAY 8,
964A = AZT RESISTANT HIV-1, 7 A012 G762-3 PRE-DRUG ISOLATE,
964B = AZT RESISTANT HIV-1, 8 A012 G691-6 POST-DRUG ISOLATE.

BETULINOL DERIVATIVES AS ANTI-HIV AGENTS

This application is a U.S. National Phase of PCT/US2005/032363, which was filed Sep. 12, 2005, which in turn claims priority to U.S. Provisional Application Ser. No. 60/609,080, filed Sep. 10, 2004; U.S. Provisional Application Ser. No. 60/630,103, filed on Nov. 22, 2004; and U.S. Provisional Application Ser. No. 60/630,150, filed on Nov. 22, 2004, each of which is incorporated in its entirety by reference herein.

FIELD OF THE INVENTION

The present invention relates generally to methods of treating HIV-1 infection in a subject and methods of inhibiting HIV-1 activity in a cell using betulinol derivative compounds.

BACKGROUND OF THE INVENTION

Human Immunodeficiency Virus ("HIV"), the virus that causes AIDS, has reached pandemic proportions in the world. Some one million people are infected with HIV in the U.S. alone, and more than forty million worldwide. Each day, approximately 12,000 adults and 1,800 children become infected. Currently, there are three classes of drug treatments for HIV, namely, reverse transcriptase ("RT") inhibitors, such as AZT (3'-azido-3'-deoxythymidine), protease inhibitors, and fusion inhibitors. Common HIV drug therapy includes a cocktail drug regiment, which may utilize, for example, nucleoside analogs like AZT, 2',3'-dideoxyinosine, and 2',3'-dideoxycytidine. These drugs act through the inhibition of the HIV reverse transcriptase activity and/or by a mechanism of oligonucleotide chain termination.

However, these currently acceptable treatment drugs are limited by either their toxicity or the emergence of drug-resistant HIV strains (Evers et al., *J. Med. Chem.* 39:1056-1063 (1996)). In addition, these drugs are costly, difficult to manufacture, and have adverse side effects. Subjects also frequently develop resistance to these drugs. Therefore, the search for new types of anti-HIV compounds is timely and important.

Betulin, or betulinol, is one of the more plentiful triterpenes, constituting up to twenty-four percent of the outer bark of the white birch (*Betula alba*) and as much as thirty-five percent of the outer bark and about five percent of the inner bark of the Manchurian white birch (*Betula platyphylla*) (Hirota et al., *J.S.C.I. Japan* 47:922 (1944)). Betulin also occurs in a free state in the bark of yellow and black birch (Steiner, *Mikrochemie, Molisch-Festschrift*, p. 405 (1936)), *Corylus avellana* and *Carpinus betulus* (Feinberg et al., *Monatsh* 44:261 (1924); Brunner et al., *Monatsh* 63:368 (1934); Brunner et al., *Monatsh* 64:21 (1934)), and *Lophopetalum toxicum* (Dieterle et al., *Arch. Pharm.* 271:264 (1933)). The exudate from the bark of *Trochodendron aralioides*, which constitutes Japanese bird-lime, contains betulin palmitate (Shishido et al., *J.S.C.I. Japan* 45:436 (1942)). Betulin has also been isolated from rosehips (Zimmermann, *Helv. Chim. Acta* 27:332 (1944)) and from the seeds of *Zizyphus vulgaris* Lamarck var. *spinosus* Bunge (Rhamnaceae) (Kawaguti et al., *J. Pharm. Soc. Japan* 60:343 (1940)). Ruhemann et al., *Brennstoff-Ch.* 13.341 (1932) discloses the presence of betulin, allobetulin, and an "oxyallobetulin" in the saponifiable portion of a benzene-alcohol extract of mid-German brown coal. In addition, the following group of lupon-row derivatives from the birch cortex extract have been identified: (a) betulinol, (b) betulinic acid, (c) betulin aldehyde, (d) betulonic acid, and (e) betulone aldehyde (Rimpler et al., *Arch. Pharm. Und. Ber. Dtsh. Ppharmaz Jes.* 299:422-428 (1995); Lindgren et al., *Acta Chem.* 20:720 (1966); and Jaaskelainen, *P. Papperi Ja Puu-Papper Och Tra.* 63:599-603 (1989)).

Birch tree cortex-extracted betulinol was first mentioned as an antiseptic in 1899. Subsequently, compounds singled out from extracts of *Hyptis emory* and *Alnus oregonu*, identified as pentacyclic styrenes and their derivatives, were shown to inhibit carcinosarcoma growth (Sheth et al., *J. Pharm. Sci.* 61:1819 (1972); Sheth et al., *J. Pharm. Sci.* 62:139-140 (1973)). It has been suggested that betulinic acid is the main anti-tumor agent in the mixture of terpenoids (Tomas et al., *Planta Medicina* 54:266-267 (1988); Ahmat et al., *J. Indian Chem. Soc.* 61:92-93 (1964)). In particular, betulinic acid showed cytotoxic activity against carcinoma cell line CO-115 of the large intestine (LD 50-0.375 mg/ml) (Ukkonen et al., *Birch Bark Extractive Kenzia Keini* 6:217 (1979)). U.S. Pat. No. 6,890,533 to Bomshteyn et al., discloses betulinol derivatives and betulinol-antibody conjugates useful in treating cancer.

Betulinol (lup-20(29)-ene-3.beta., 28-diol) is commercially available (e.g., Sigma Chemical Co., St. Louis, Mo.) and is described for example, in "Merck 1212," *The Merck Index*, 11th ed. (1989), and Simonsen et al., *The Terpenes* Vol. IV, Cambridge U. Press, pp. 187-328 (1957).

The chemical structure of betulinol is:

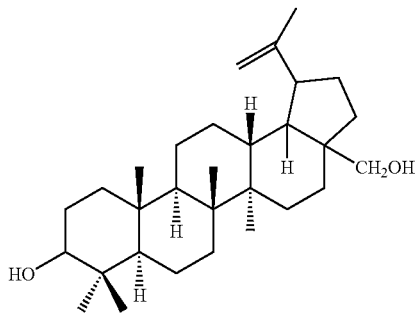

Betulinol has been shown to have anti-viral activity, including anti-herpes virus activity (U.S. Pat. No. 5,750,578 to Carlson et al.) and anti-HIV activity (U.S. Pat. No. 6,172,110 to Lee et al.; Sun et al., *J. Med. Chem.* 41:4648-4657 (1998)). Certain betulinol derivatives have also been investigated with regard to potential for anti-viral activity.

Betulonic acid and derivatives thereof (Hashimoto et al., *Bioorg. Med. Chem.* 5:2133-2143 (1997); Sun et al., *J. Med. Chem.* 41:4648-4657 (1998)), betulinic acid and derivatives thereof, dihydrobetulinic acid and derivatives thereof (Hashimoto et al., *Bioorg. Med. Chem.* 5:2133-2143 (1997); Sun et al., *J. Med. Chem.* 45:4271-4275 (2002); Kashiwada et al., *Bioorg. Med. Chem. Lett.* 11:183-185 (2001); Kashiwada et al., *J. Med. Chem.* 39:1016-1017 (1996); Flekhter et al., *Bioorg. Khim.* 28:543-550 (2003); "Betulinic Acid Derivatives in AIDS," *Marketletter* (May 2, 1994); DeClercq, *Med. Res. Rev.* 20:323-349 (2000); Vlietinck et al., *Plant Med.* 64:97-109 (1998); Soler et al., *J. Med. Chem.* 39:1069-1083 (1996); Evers et al., *J. Med. Chem.* 39:1056-1068 (1996); U.S. Pat. Nos. 5,468,888 to Bouboutou et al., 5697828 to Lee et al., 5,869,535, 6,225,353, 6495600, and 6569842 to Pezzuto, 6048847 to Ramadoss et al., and 6403816 to Jaggi et al.; and PCT Application Publication No. WO 96/39033 to Lee et al.), betulin diacetate (Sun et al., *Med. Chem.* 41:4648-4657 (1998)), and betulone aldehyde (U.S. Pat. Nos. 5,869,535, 6,225,353 and 6,495,600 to Pezzuto et al.) have been investigated with regard to potential for anti-HIV activity. In addition, certain betulin derivatives, including betulin diacetate (U.S. Pat. No. 5,750,578 to Carlson) and betulinic acid (U.S. Pat. No. 6,214,350 to Hwang) have been shown to exhibit anti-herpes virus activity.

Unfortunately, however, many of these betulinol derivative compounds have significant drawbacks to their use. Betulin diacetate and betulonic acid, for example, have been shown to exhibit a low therapeutic index (Sun et al., *J. Med. Chem.* 41:4648-4657 (1998)). In addition, certain betulinic acid derivatives, such as betulonic acid, have been found to be cytotoxic, interfering with the proliferation of cells (Hashimoto et al., *Bioorg. Med. Chem.* 5:2133-2143 (1997)). In addition, no current anti-HIV agent, with the exception of α-interferon, has any effect on release of virus from a chronically infected cell. Thus, the search for new anti-HIV compounds remains timely and important.

Betulinol derivatives in general, and betulonic acid in particular, are soluble in a number or organic solvents such as ethanol and DMSO. However, betulonic acid and the known betulinol derivatives are generally insoluble in aqueous environment or other pharmaceutically acceptable solvents. Good solubility in an aqueous environment is an important property for a pharmaceutical agent. Absent this property, administration of the pharmaceutical agent to mammals can be difficult and biological activity in such mammals (including humans) may be impeded or entirely absent. Due to their limited solubility in aqueous solutions, the use of terpenoids such as betulinol and it derivatives as pharmaceuticals has been limited. To be effective as a pharmaceutical agent, especially for oral ingestion, water soluble betulinol derivatives would be desirable.

The present invention is directed to overcoming these and other deficiencies in the art.

SUMMARY OF THE INVENTION

One aspect of the present invention relates to a method of treating HIV-1 infection in a subject. This method involves administering to a subject with HIV-1 infection a therapeutically effective amount of a compound having the formula

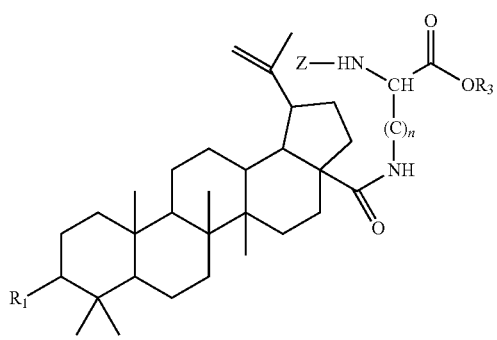

where
$R_1$ is selected from the group consisting of $-CH_3$, $=O$, $-OH$, $-OCH_3$, $-OC(O)CH_3$, $-NNH-2,4$-Dinitrophenyl Hydrazine ("DNP"), and $=S$ and
$R_3$ is selected from the group consisting of H and $C_1$-$C_5$ alkyl,
n is an integer from 1 to 12; and
Z is H or a protective group,
or a pharmaceutically acceptable salt or derivative thereof, under conditions effective to treat the subject for HIV-1 infection.

As used herein, in the formulas, both $-(C)_n-$ and $-(CH_2)_n-$ represent a saturated hydrocarbon chain of the formula $-(CH_2)_n-$.

Another aspect of the present invention relates to a method of treating HIV-1 infection in a subject. This method involves administering to a subject with HIV-1 infection a therapeutically effective amount of a compound having the formula

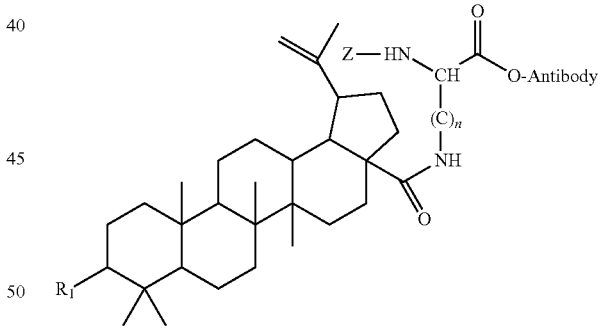

where
$R_1$ is selected from the group consisting of $-CH_3$, $=O$, $-OH$, $-OCH_3$, $-OC(O)CH_3$, $-NNH-2,4$-DNP, and $=S$ and
n is an integer from 1 to 12; and
Z is H or a protective group,
or a pharmaceutically acceptable salt or derivative thereof, under conditions effective to treat the subject for HIV-1 infection.

A further aspect of the present invention relates to a method of treating HIV-1 infection in a subject. This method involves administering to a subject with HIV-1 infection a therapeutically effective amount of a compound having the formula

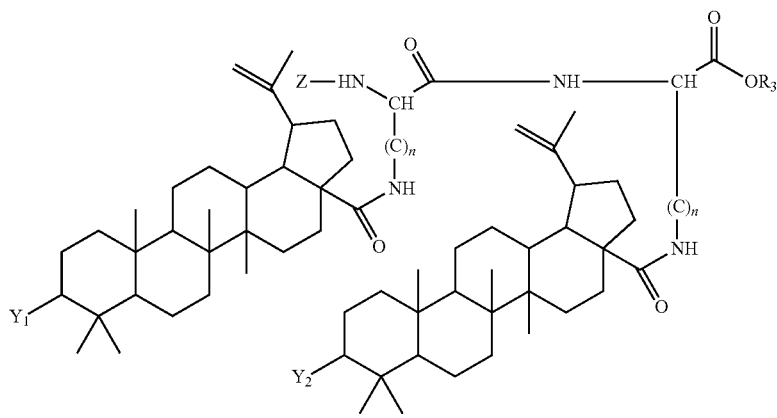

where

Y$_1$ and Y$_2$ are independently selected from the group consisting of —CH$_3$, =O, —OH, —OCH$_3$, —OC(O)CH$_3$, —NNH-2,4-DNP, and =S;

R$_3$ is selected from the group consisting of H and C$_1$-C$_5$ alkyl;

Z is H or a protective group; and n is an integer from 1 to 12, or a pharmaceutically acceptable salt or derivative thereof, under conditions effective to treat the subject for HIV-1 infection.

Yet another aspect of the present invention relates to a method of treating HIV-1 infection in a subject. This method involves administering to a subject with HIV-1 infection a therapeutically effective amount of a compound having the formula

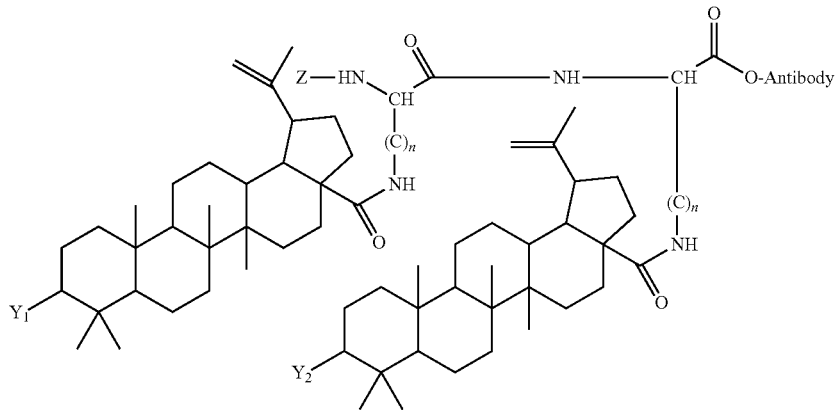

where

Y$_1$ and Y$_2$ are independently selected from the group consisting of —CH$_3$, =O, —OH, —OCH$_3$, —OC(O)CH$_3$, —NNH-2,4-DNP, and =S;

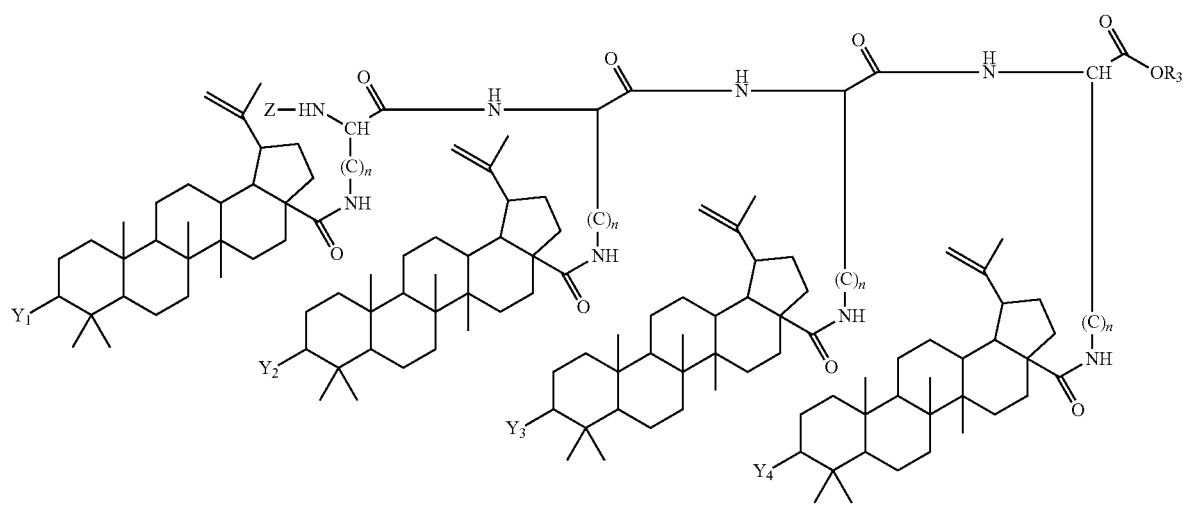

where $Y_1$, $Y_2$, $Y_3$, and $Y_4$ are independently selected from the group consisting of —$CH_3$, =O, —OH, —$OCH_3$, —OC(O)$CH_3$, —NNH-2,4-DNP, and =S;

$R_3$ is selected from the group consisting of H and $C_1$-$C_5$ alkyl;

n is an integer from 1 to 12; and

Z is H or a protective group, or a pharmaceutically acceptable salt or derivative thereof, under conditions effective to treat the subject for HIV-1 infection.

Still another aspect of the present invention relates to a method of treating HIV-1 infection in a subject. This method involves administering to a subject with HIV-1 infection a therapeutically effective amount of a compound having the formula where $Y_1$, $Y_2$, $Y_3$, and $Y_4$ are independently selected from the group consisting of —$CH_3$, =O, —OH, —$OCH_3$, —OC(O)$CH_3$, —NNH-2,4-DNP, and =S;

n is an integer from 1 to 12; and

Z is H or a protective group, or a pharmaceutically acceptable salt or derivative thereof, under conditions effective to treat the subject for HIV-1 infection.

Still a further aspect of the present invention relates to a method of treating HIV-1 infection in a subject. This method involves administering to a subject with HIV-1 infection a therapeutically effective amount of a compound having the formula

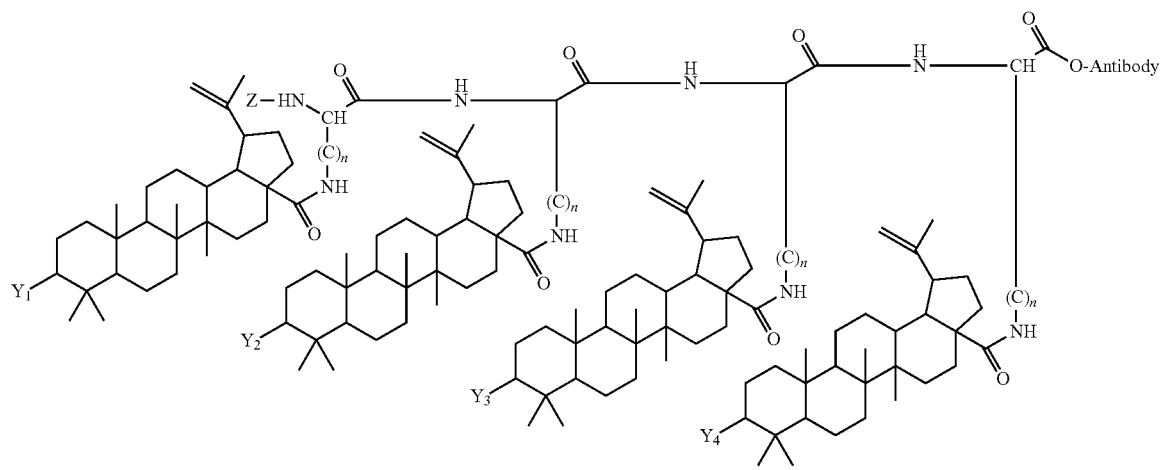

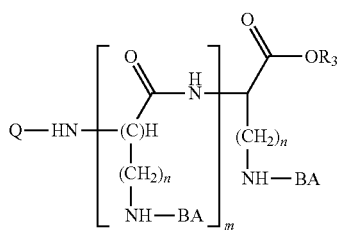

wherein

BA is a compound having the formula:

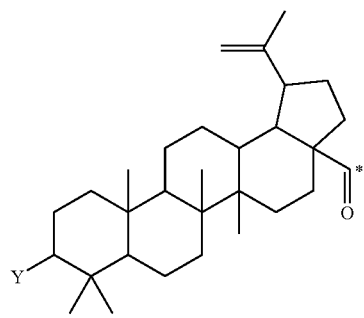

wherein

Y is selected from the group consisting of —CH$_3$, =O, —OH, —OCH$_3$, —OC(O)CH$_3$, —NNH-2,4-DNP, and =S;

* is a binding site;

Q is BA, a leaving group, or H;

R$_3$ is H or C$_1$-C$_5$ alkyl;

n is an integer from 1 to 12; and m is an integer from 1 to 6, or a pharmaceutically acceptable salt or derivative thereof, under conditions effective to treat the subject for HIV-1 infection.

Another aspect of the present invention relates to a method of treating HIV-1 infection in a subject. This method involves administering to a subject with HIV-1 infection a therapeutically effective amount of a compound having the formula

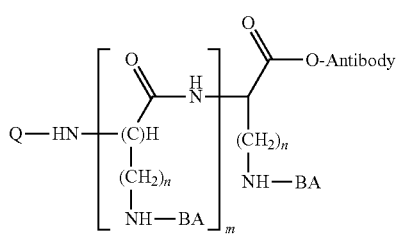

where

BA is a compound having the formula:

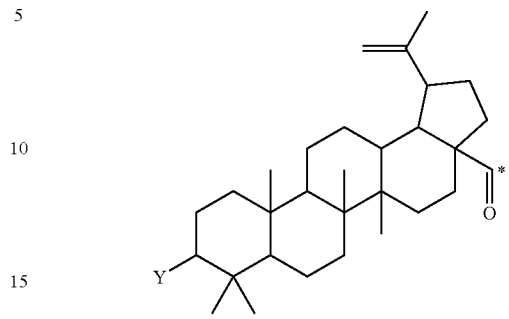

where

Y is selected from the group consisting of —CH$_3$, =O, —OH, —OCH$_3$, —OC(O)CH$_3$, —NNH-2,4-DNP, and =S;

* is a binding site;

Q is BA, a leaving group, or H;

n is an integer from 1 to 12; and m is an integer from 1 to 6, or a pharmaceutically acceptable salt or derivative thereof, under conditions effective to treat the subject for HIV-1 infection.

A further aspect of the present invention relates to a method of inhibiting HIV-1 activity in a cell. This method involves providing a cell infected with HIV-1 and contacting the cell with a compound having the formula

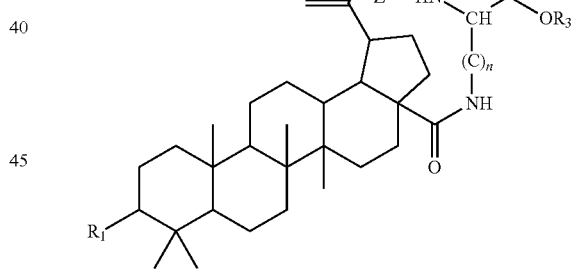

where

R$_1$ is selected from the group consisting of —CH$_3$, =O, —OH, —OCH$_3$, —OC(O)CH$_3$, —NNH-2,4-DNP, and =S and R$_3$ is selected from the group consisting of H and C$_1$-C$_5$ alkyl, n is an integer from 1 to 12; and Z is H or a protective group, or a pharmaceutically acceptable salt or derivative thereof, under conditions effective to inhibit HIV-1 activity in the cell.

Yet another aspect of the present invention relates to a method of inhibiting HIV-1 activity in a cell. This method involves providing a cell infected with HIV-1 and contacting the cell with a compound having the formula

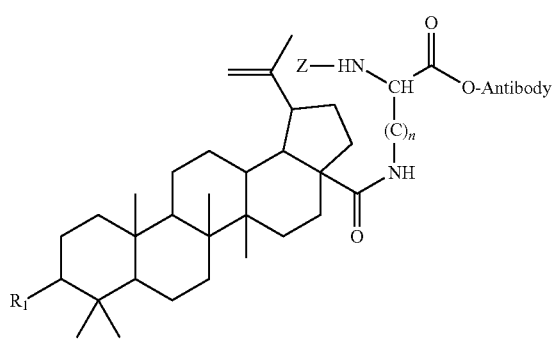

where
R₁ is selected from the group consisting of —CH₃, =O, —OH, —OCH₃, —OC(O)CH₃, —NNH-2,4-DNP, and =S
and
n is an integer from 1 to 12; and
Z is H or a protective group,
or a pharmaceutically acceptable salt or derivative thereof, under conditions effective to inhibit HIV-1 activity in the cell.

Yet a further aspect of the present relates to a method of inhibiting HIV-1 activity in a cell. This method involves providing a cell infected with HIV-1 and contacting the cell with a compound having the formula where $Y_1$ and $Y_2$ are independently selected from the group consisting of —CH₃, =O, —OH, —OCH₃, —OC(O)CH₃, —NNH-2,4-DNP, and =S;

$R_3$ is selected from the group consisting of H and $C_1$-$C_5$ alkyl;

Z is H or a protective group; and n is an integer from 1 to 12, or a pharmaceutically acceptable salt or derivative thereof, under conditions effective to inhibit HIV-1 activity in the cell.

Still another aspect of the present invention relates to a method of inhibiting HIV-1 activity in a cell. This method involves providing a cell infected with HIV-1 and contacting the cell with a compound having the formula

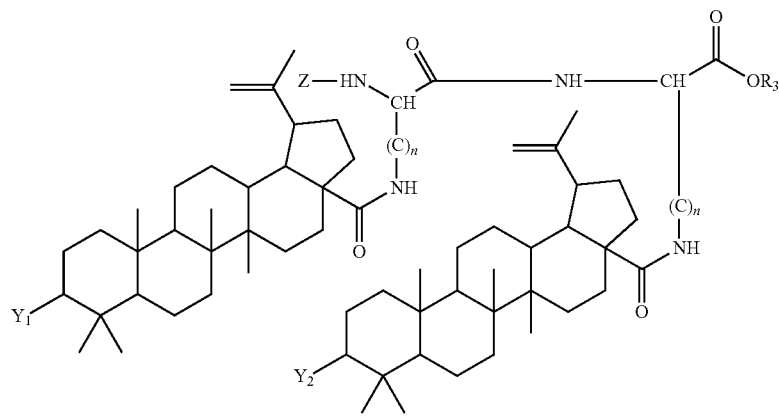

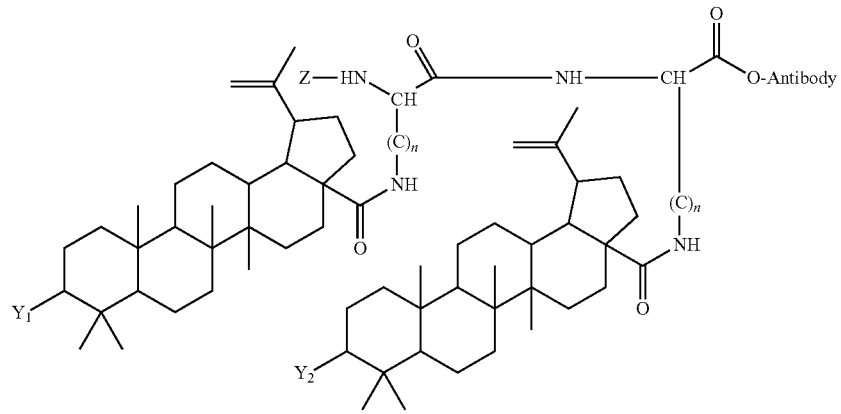

where $Y_1$ and $Y_2$ are independently selected from the group consisting of —$CH_3$, =O, —OH, —$OCH_3$, —$OC(O)CH_3$, —NNH-2,4-DNP, and =S;

Z is H or a protective group; and n is an integer from 1 to 12, or a pharmaceutically acceptable salt or derivative thereof, under conditions effective to inhibit HIV-1 activity in the cell.

Another aspect of the present invention relates to a method of inhibiting HIV-1 activity in a cell. This method involves providing a cell infected with HIV-1 and contacting the cell with a compound having the formula where $Y_1$, $Y_1$, $Y_3$, and $Y_4$ are independently selected from the group consisting of —$CH_3$, =O, —OH, —$OCH_3$, —$OC(O)CH_3$, —NNH-2,4-DNP, and =S;

$R_3$ is selected from the group consisting of H and $C_1$-$C_5$ alkyl;

n is an integer from 1 to 12; and

Z is H or a protective group, or a pharmaceutically acceptable salt or derivative thereof, under conditions effective to inhibit HIV-1 activity in the cell.

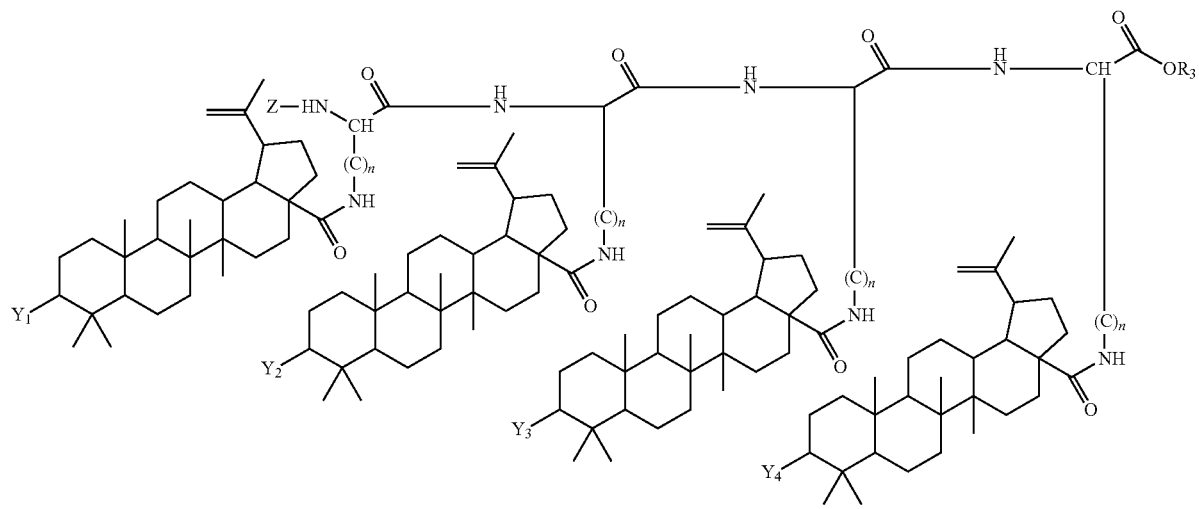

A further aspect of the present invention relates to a method of inhibiting HIV-1 activity in a cell. This method involves providing a cell infected with HIV-1 and contacting the cell with a compound having the formula

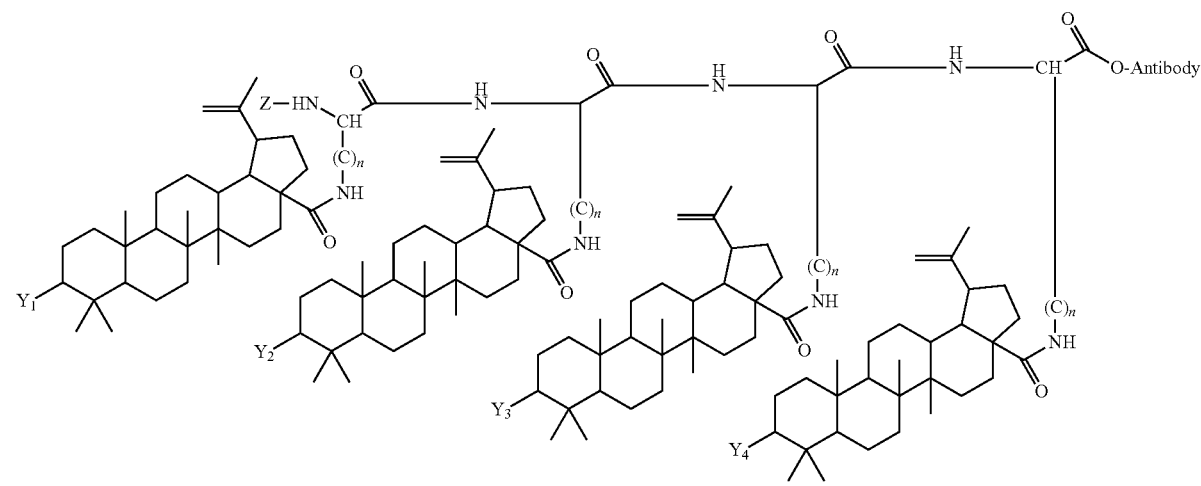

where $Y_1$, $Y_2$, $Y_3$, and $Y_4$ are independently selected from the group consisting of —$CH_3$, =O, —OH, —$OCH_3$, —$OC(O)CH_3$, —NNH-2,4-DNP, and =S;

n is an integer from 1 to 12; and

Z is H or a protective group, or a pharmaceutically acceptable salt or derivative thereof, under conditions effective to inhibit HIV-1 activity in the cell.

Yet another aspect of the present invention relates to a method of inhibiting HIV-1 activity in a cell. This method involves providing a cell infected with HIV-1 and contacting the cell with a compound having the formula

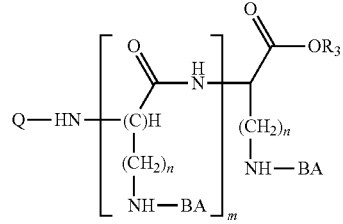

wherein

BA is a compound having the formula:

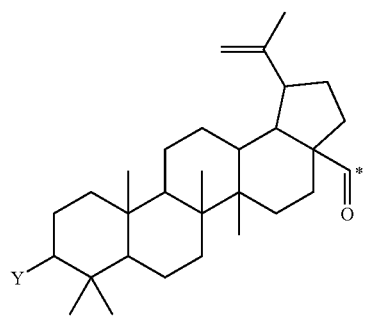

wherein

Y is selected from the group consisting of —$CH_3$, =O, —OH, —$OCH_3$, —$OC(O)CH_3$, —NNH-2,4-DNP, and =S;

* is a binding site;

Q is BA, a leaving group, or H;

$R_3$ is H or $C_1$-$C_5$ alkyl;

n is an integer from 1 to 12; and m is an integer from 1 to 6, or a pharmaceutically acceptable salt or derivative thereof, under conditions effective to inhibit HIV-1 activity in the cell.

Yet a further aspect of the present invention relates to a method of inhibiting HIV-1 activity in a cell. This method involves providing a cell infected with HIV-1 and contacting the cell with a compound having the formula

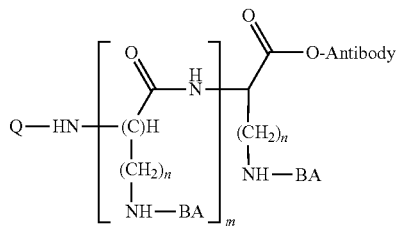

where

BA is a compound having the formula:

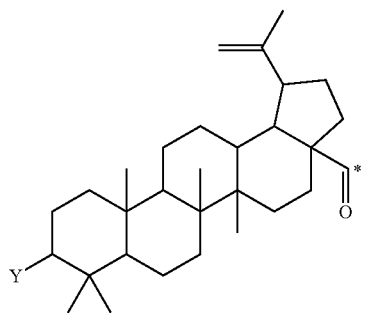

where

Y is selected from the group consisting of —$CH_3$, =O, —OH, —$OCH_3$, —$OC(O)CH_3$, —NNH-2,4-DNP, and =S;

* is a binding site;

Q is BA, a leaving group, or H;

n is an integer from 1 to 12; and m is an integer from 1 to 6, or a pharmaceutically acceptable salt or derivative thereof, under conditions effective to inhibit HIV-1 activity in the cell.

Still another aspect of the present invention relates to a method of treating and/or inhibiting HIV-1 infection in a human. This method involves administering to a human infected with HIV-1 a therapeutically effective amount of a compound having the formula

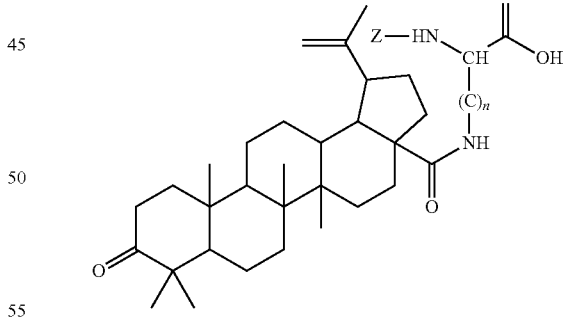

where n is an integer from 1 to 12 and

Z is H or a protective group, or a pharmaceutically acceptable salt or derivative thereof, under conditions effective to treat and/or inhibit the human for HIV-1 infection.

Still a further aspect of the present invention relates to a method of treating and/or inhibiting HIV-1 infection in a human. This method involves administering to a human infected with HIV-1 a therapeutically effective amount of a compound having the formula

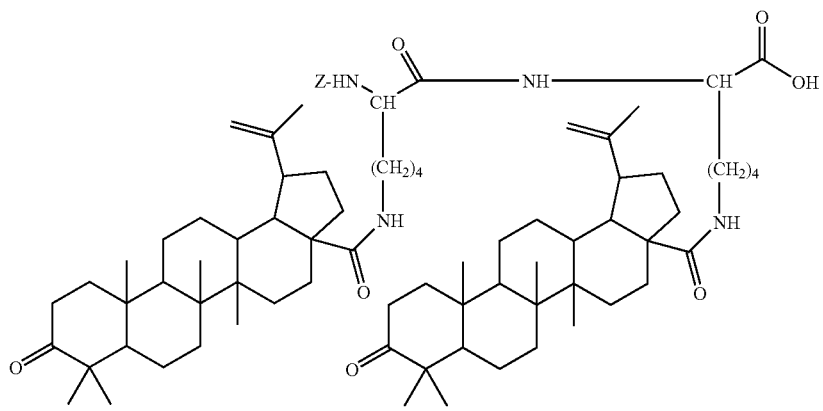

where

Z is H or a protective group, or a pharmaceutically acceptable salt or derivative thereof, under conditions effective to treat and/or inhibit the human for HIV-1 infection.

Another aspect of the present invention relates to a method of treating and/or inhibiting HIV-1 infection in a subject. This method involves administering to a subject infected with HIV-1 a therapeutically effective amount of a compound having the formula:

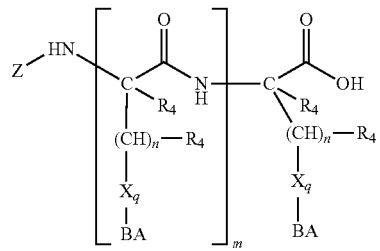

where

BA is a compound having the formula:

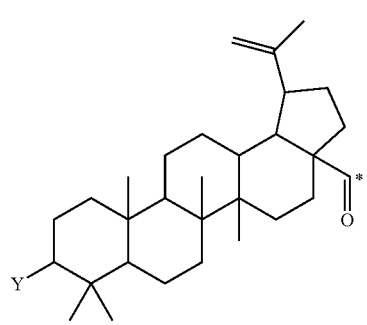

where

Y is selected from the group consisting of —$CH_3$, =O, —OH, —$OCH_3$, —$OC(O)CH_3$, —NNH-2,4-dinitrophenyl hydrazine, and =S;

* is a binding site;

X is selected from the group consisting of

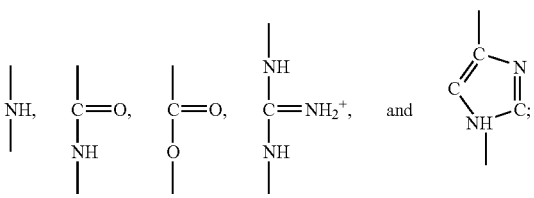

each $R_4$ is independently selected from the group consisting of H, $CH_3$, $CH_2$—$CH_3$, $NH_2$ and OH;

Z is H, a protective group, or BA;

n is an integer from 1 to 8;

m is an integer from 1 to 6; and q is 0 or 1, or a pharmaceutically acceptable salt thereof.

A further aspect of the present invention relates to a method of treating HIV-1 infection in a subject. This method involves administering to a subject infected with HIV-1 a therapeutically effective amount of a compound having the formula:

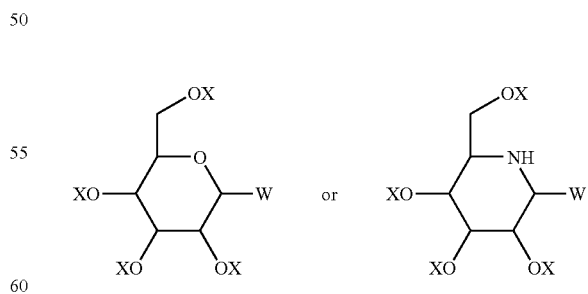

where

W is H, OX, or $CH_2$—OX; and each X is independently H, a sugar, or BA, and wherein at least 1 X is BA; and BA is a compound having the formula:

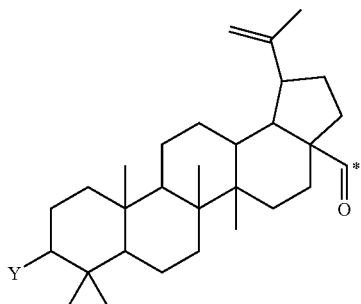

where
Y is selected from the group consisting of —CH₃, =O, —OH, —OCH₃, —OC(O)CH₃, —NNH-2,4-dinitrophenyl hydrazine, and =S; and
* is a binding site,
or a pharmaceutically acceptable salt thereof.

Yet another aspect of the present invention relates to a method of treating HIV-1 infection in a human. This method involves administering to a human infected with HIV-1 a therapeutically effective amount of a compound having the formula:

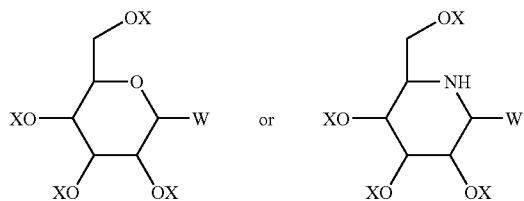

where
W is H, OX, or CH₂—OX; and
each X is independently H, a sugar, or BA, and wherein at least 1 X is BA; and
BA is a compound having the formula:

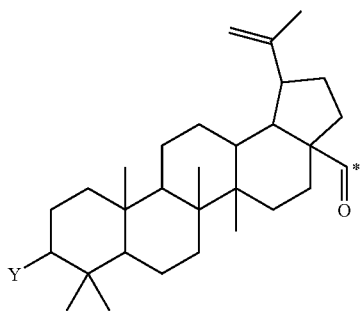

where
Y is selected from the group consisting of —CH₃, =O, —OH, —OCH₃, —OC(O)CH₃, —NNH-2,4-dinitrophenyl hydrazine, and =S; and
* is a binding site,
or a pharmaceutically acceptable salt thereof under conditions effective to treat the human for HIV-1 infection.

Yet a further aspect of the present invention relates to a method of treating HIV-1 infection in a subject. This method involves administering to a subject infected with HIV-1 a therapeutically effective amount of a compound having the formula:

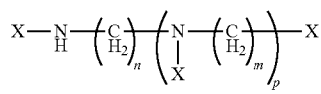

where
each X is H or a compound of the formula:

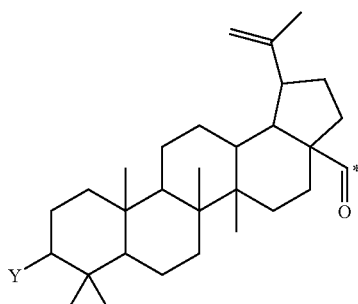

where
Y is selected from the group consisting of —CH₃, =O, —OH, —OCH₃, —OC(O)CH₃, —NNH-2,4-dinitrophenyl hydrazine, and =S;
* is a binding site,
n is an integer from 1 to 8;
p is 0 or 1; and
m is an integer from 1 to 8;
wherein at least one X is not H,
or a pharmaceutically acceptable salt thereof.

Still another aspect of the present invention relates to a method of treating HIV-1 infection in a human. This method involves administering to a human infected with HIV-1 a therapeutically effective amount of a compound having the formula:

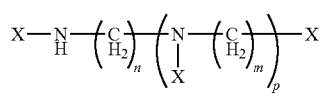

where
each X is H or a compound of the formula:

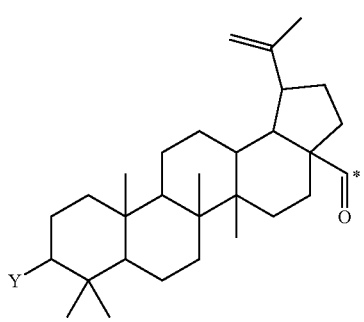

where

Y is selected from the group consisting of —CH₃, =O, —OH, —OCH₃, —OC(O)CH₃, —NNH-2,4-dinitrophenyl hydrazine, and =S;

\* is a binding site, n is an integer from 1 to 8;

p is 0 or 1; and m is an integer from 1 to 8;

wherein at least one X is not H, or a pharmaceutically acceptable salt thereof under conditions effective to treat the human for HIV-1 infection.

Still a further aspect of the present invention relates to a method of treating HIV-1 infection in a subject. This method involves administering to a subject infected with HIV-1 a therapeutically effective amount of a compound having the formula:

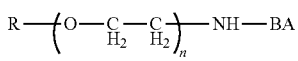

where

R is a $C_1$ to $C_5$ alkyl;

n is an integer between 5 and 1000; and

BA is a compound having the formula:

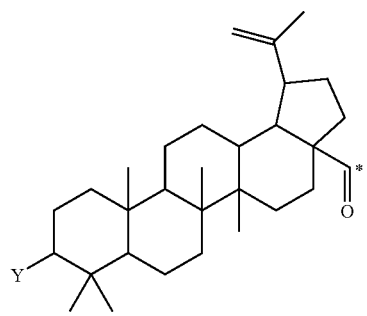

where

Y is selected from the group consisting of —CH₃, =O, —OH, —OCH₃, —OC(O)CH₃, —NNH-2,4-dinitrophenyl hydrazine, and =S; and \* is a binding site, or a pharmaceutically acceptable salt thereof.

Another aspect of the present invention relates to a method of treating HIV-1 infection in a human. This method involves administering to a human infected with HIV-1 a therapeutically effective amount of a compound having the formula:

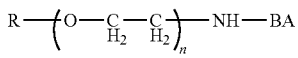

where

R is a $C_1$ to $C_5$ alkyl;

n is an integer between 5 and 1000; and

BA is a compound having the formula:

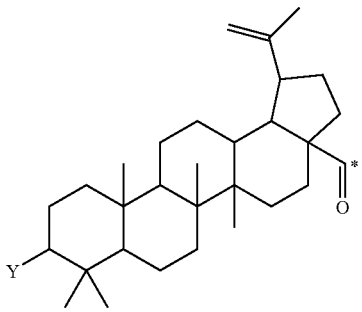

where

Y is selected from the group consisting of —CH₃, =O, —OH, —OCH₃, —OC(O)CH₃, —NNH-2,4-dinitrophenyl hydrazine, and =S; and \* is a binding site, or a pharmaceutically acceptable salt thereof under conditions effective to treat the human for HIV-1 infection.

While the prior art discloses a number of different betulinol derivatives having antiviral activity, the betulinol derivatives of the present invention are particularly effective against Human Immunodeficiency Virus and, in particular, HIV-1. Moreover, the betulinol derivatives of the present invention produce anti-HIV-1 activity superior to anti-HIV-1 activity known in the art for other betulinol derivatives. In addition, the compounds of the present invention provide this superior anti-HIV-1 activity without affecting the proliferation of cells.

BRIEF DESCRIPTION OF THE DRAWINGS

In FIG. 4A, the most intense peak in the ESI mass spectrum is the singly protonated ion at m/z 1261. The low level impurities with ion at m/z 581, 627, 639, and 683 are present. Since the sensitivity for the structure is low, 40 μM concentration solution was used to observe a strong m/z 1261 peak. In FIG. 4B, the predominant fragmentation process, as it was in monomer ester, is the loss of a 100 Da neutral, presumably in the form of isobutylene+$CO_2$. Among the additional, very weak, product ions those at m/z 1204 and 734 are significant, because they can be interpreted as a loss of $C_4H_8$ and a loss of a betulonic acid residue, respectively.

DETAILED DESCRIPTION OF THE INVENTION

Figure 1A:
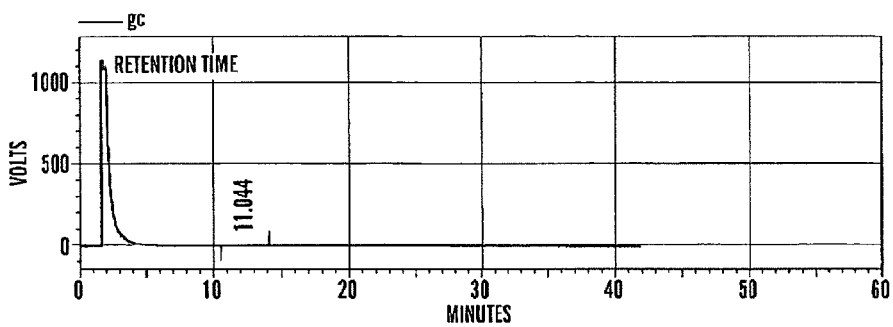
FIGS. 1A-C show chromatograms of betulonic acid and its derivatives with their corresponding retention time. Close examination of these chromatograms reveals that the conjugated betulonic acid monomer and dimer gave neat chromatograms.

The present invention relates to methods of treating HIV-1 infection in a subject. These methods involve administering to a subject with HIV-1 infection a therapeutically effective amount of a betulinol derivative compound, or pharmaceutically acceptable salt or derivative thereof, under conditions effective to treat the subject for HIV-1 infection.

Betulinol and betulinol derivatives are compounds having the general chemical structure of Formula I (I)

where
$R^1$ is selected from the group consisting of —$CH_3$, =O, —OH, —$OCH_3$, —OC(O)$CH_3$, —NNH-2,4-DNP, and =S and
$R^2$ is selected from the group consisting of —H, —$CH_3$, —CHO, —$CH_2$OH, —$CH_2OCH_3$, —$CH_2$OC(O)$CH_3$, —$COCH_3$, —COOH, and —CH=NNH-2,4-DNP.

Specific configurations of betulinol and its derivatives are summarized in Table 1.

TABLE 1

Betulinol and Its Derivatives

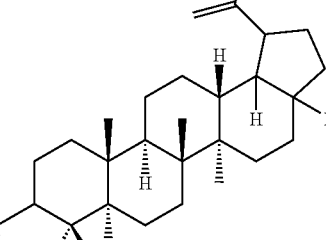

| Betulinol Derivative | $R_1$ =<br>$R_2$ = | Formula/<br>Molecular Weight |
|---|---|---|
| 1. Betulinol | $R_1$—OH<br>$R_2$—$CH_2$OH | $C_{30}H_{50}O_2$<br>442 g/mol |
| 2. Betulinic Acid | $R_1$—OH<br>$R_2$—COOH | $C_{30}H_{48}O_3$<br>456 |
| 3. Betulin Aldehyde | $R_1$—OH<br>$R_2$—CHO | $C_{30}H_{48}O_2$<br>440 |
| 4. Betulonic Acid | $R_1$=O<br>$R_2$—COOH | $C_{30}H_{47}O_3$<br>455 |
| 5. Betulon Aldehyde | $R_1$=O<br>$R_2$—CHO | $C_{30}H_{47}O_2$<br>439 |
| 6. Betulin Diacetate | $R_1$—OCOCH$_3$<br>$R_2$—$CH_2$OCOCH$_3$ | $C_{34}H_{54}O_4$<br>526 |
| 7. Betulin Dimethyl ether (Cornelon) | $R_1$—OCH$_3$<br>$R_2$—$CH_2$OCH$_3$ | $C_{32}H_{54}O_2$<br>470 |
| 8. 3-Acetoxy Betulin | $R_1$—OCOCH$_3$<br>$R_2$—OH | C32H54O3<br>484 |
| 9. 28-Acetoxy Betulin | $R_1$—OH<br>$R_2$—$CH_2$OCOCH$_3$ | $C_{32}H_{54}O_3$<br>484 |
| 10. 3,28-2,4-DNP Betulin Hydrazone | $R_1$—NNH-2,4-DNP<br>$R_2$—CH=NNH-2,4-DNP | $C_{42}H_{55}O_8N_6$<br>800 |
| 11. Betulin 3-Thione | $R_1$=S<br>$R_2$—COOH | $C_{30}H_{46}O_2S$<br>470 |

Betulinol can be isolated from the outer layer of the bark of the white birch tree *Betula alba* by sublimation (Lowitz, *Crell's Annalen* 1.312 (1788) and Mason, *Silliman's Am. J.*, 20.282 (1831), which are hereby incorporated by reference in their entirety) or by extraction with an alcohol, such as ethanol (Hunefeld, *J. Prakt. Chem.* 7:53 (1836) and Hess, *Poggendorff's Annalen* 46.319 (1839), which are hereby incorporated by reference in their entirety). Other sources of betulinol and methods for its isolation and purification have been described in, for example, Sheth et al., *J. Pharm. Sci.* 61:1819 (1972) (raw vegetables and extracts of *Hyptis emory*) and Sheth et al., *J. Pharm. Sci.* 62:139-140 (1973) (*Alnus oregonu*), which are hereby incorporated by reference in their entirety.

In a preferred method, betulinol is isolated from the non-saponifiable substance of floral soap. Briefly, the crushed initial leaf wood and components of a sulfate boiling procedure (NaOH, $Na_2SO_4$, $Na_2S_2O_3$, $Na_2SO_3$) are lodged to a boiling pot in a batch or continuous process. Under the temperature of 110° C. to 120° C. and, optionally, at increased pressure, lignin (the component of wood) dissolves. Crude cellulose is derived from the pulping liquor which is composed of lignin, cellulose, and black buck. Black buck is a composition of black buck with salts of tall acid and non-saponifiable substances. The crude cellulose is used in paper production, whereas the sulfate soap is separated from the black buck by centrifugation or by a settling process. Treatment of the sulfate soap with sulfuric acid produces tall oil. The non-saponifiable substances are separated as crude betulinol. Recrystallization of the crude betulinol, such as from acetone, ethyl acetate, isopropanol, butanol, ethanol, and the like, yields pure betulinol. The black buck residue present after centrifugation or settling can be advantageously recycled.

Betulinol derivative compounds of Formula I are synthesized by standard methods that are well known in the art. For example, detailed instructions on how to synthesize and prepare compounds of Formula I are set forth in U.S. Pat. No. 6,890,533, to Bomshteyn et al., which is hereby incorporated by reference in its entirety. The structure of betulinol is based on a 30-carbon skeleton of four, six-member rings and one five-member E-ring containing an a-isopropyl group. The structural component of betulinol has a primary and a secondary hydroxyl group at C-3 and C-28. Betulinol has three sites, at carbon 3, 20, and 28, where chemical modification can occur to yield derivatives. Synthetic schemes for the preparation of betulinol derivative compounds are described in the Examples below.

It has now been discovered that betulinol derivatives can be made more water soluble by conjugation to one or more members of a group of solubility enhancing compounds. The conjugate has a significantly greater solubility in aqueous solutions but retains a high level of biological activity including, for example, activity against HIV-1 infection. This is particularly important since the chemistry required for making therapeutic agents more soluble often causes the biological activity of the therapeutic agent to be reduced or in some cases, entirely lost.

Conjugated and immunoconjugated betulinol derivative compounds useful in the methods of the present invention can also be synthesized from betulinol. Synthetic schemes for the preparation of conjugated and immunoconjugated betulinol derivative compounds are described the Examples below.

One aspect of the present invention relates to a method of treating HIV-1 infection in a subject. This method involves administering to a subject with HIV-1 infection a therapeutically effective amount of a compound having the formula

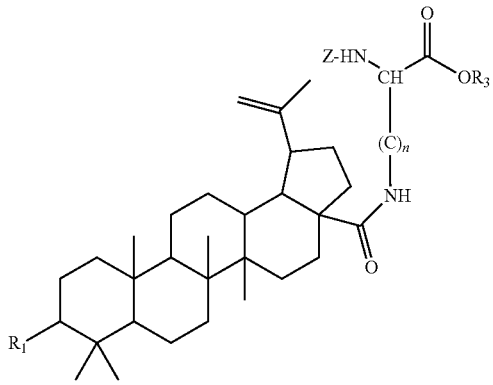

where $R_1$ is selected from the group consisting of —$CH_3$, =O, —OH, —$OCH_3$, —OC(O)$CH_3$, —NNH-2,4-DNP, and =S and $R_3$ is selected from the group consisting of H and $C_1$-$C_5$ alkyl, n is an integer from 1 to 12; and Z is H or a protective group, or a pharmaceutically acceptable salt or derivative thereof, under conditions effective to treat the subject for HIV-1 infection.

In a preferred embodiment, n is an integer from 2 to 8.

Preferably, the above compound has a structure where:

$R_1$ is =O, $R_3$ is methyl, and n is 4;

$R_1$ is =O, $R_3$ is H, Z is —C(=O)—O-t-buty 1, and n is 4; or $R_1$ is —OH, $R_3$ is H, Z is —C(=O)—O-t-buty 1, and n is 4.

In carrying out this and other methods of the present invention, protective group Z is H or is selected from the group consisting of butyloxycarbonyl and carbobenzoxy. Preferably, Z is butyloxycarbonyl.

The above method employs a conjugated betulinol derivative monomer compound, which can be made by a method that involves reacting a reactant compound of the formula

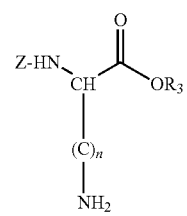

with a betulinol derivative compound of the formula

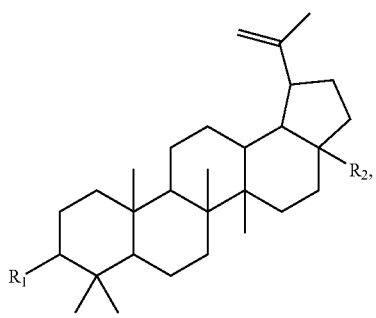

where $R_2$ is a carbonyl containing group, under conditions effective to make the conjugated betulinol derivative monomer compound.

Another aspect of the present invention relates to a method of treating HIV-1 infection in a subject. This method involves administering to a subject with HIV-1 infection a therapeutically effective amount of a compound having the formula

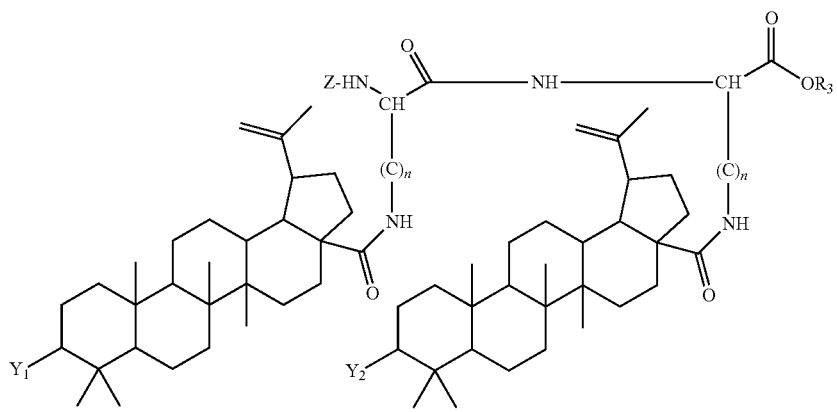

where $Y_1$ and $Y_2$ are independently selected from the group consisting of —$CH_3$, =O, —OH, —$OCH_3$, —$OC(O)CH_3$, —NNH-2,4-DNP, and =S;

$R_3$ is selected from the group consisting of H and $C_1$-$C_5$ alkyl;

Z is H or a protective group; and n is an integer from 1 to 12, or a pharmaceutically acceptable salt or derivative thereof, under conditions effective to treat the subject for HIV-1 infection.

In a preferred embodiment, n is an integer from 2 to 8.

Preferably, the above compound has a structure where:

$Y_1$ and $Y_2$ are =O, $R_3$ is methyl, and n is 4;

$Y_1$ and $Y_2$ are =O, $R_3$ is H, Z is —C(=O)—O-t-buty 1, and n is 4; or $Y_1$ and $Y_2$ are —OH, $R_3$ is H, Z is —C(=O)—O-t-buty 1, and n is 4.

The above method employs a conjugated betulinol derivative dimer compound, which can be made by a method that involves reacting a reactant compound of the formula

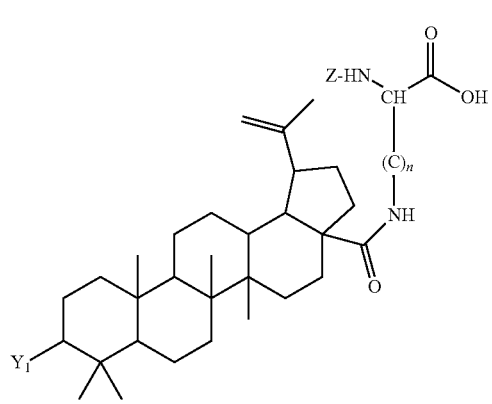

with a compound of the formula

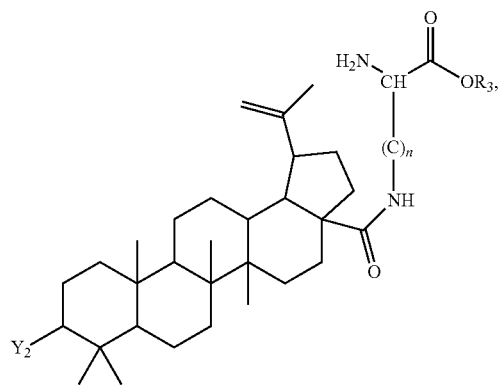

under conditions effective to make the conjugated betulinol derivative dimer compound.

A further aspect of the present invention relates to a method of treating HIV-1 infection in a subject. This method involves administering to a subject with HIV-1 infection a therapeutically effective amount of a compound having the formula

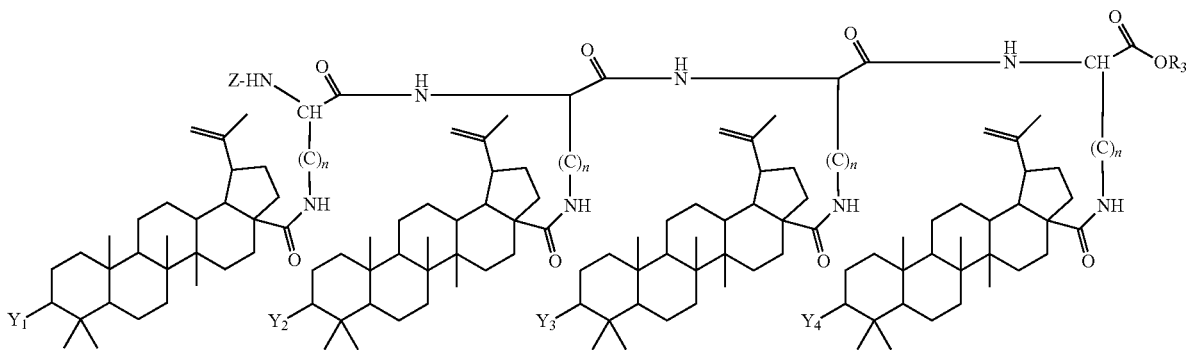

where $Y_1$, $Y_2$, $Y_3$, and $Y_4$ are independently selected from the group consisting of $CH_3$, =O, —OH, —OCH$_3$, —OC(O)CH$_3$, —NNH-2,4-DNP, and =S;

$R_3$ is selected from the group consisting of H and $C_1$-$C_5$ alkyl;

n is an integer from 1 to 12; and

Z is H or a protective group, or a pharmaceutically acceptable salt or derivative thereof, under conditions effective to treat the subject for HIV-1 infection.

In a preferred embodiment, n is an integer from 2 to 8. Preferably, the above compound has a structure where:

$Y_1$, $Y_2$, $Y_3$, and $Y_4$ are =O, $R_3$ is methyl, and n is 4;

$Y_1$, $Y_2$, $Y_3$, and $Y_4$ are =O, $R_3$ is H, Z is —C(=O)—O-t-butyl, and n is 4; or $Y_1$, $Y_2$, $Y_3$, and $Y_4$ are —OH, $R_3$ is H, Z is —C(=O)—O-t-butyl, and n is 4.

The above method employs a conjugated betulinol derivative tetramer compound, which is made by a method that involves reacting a reactant compound of the formula

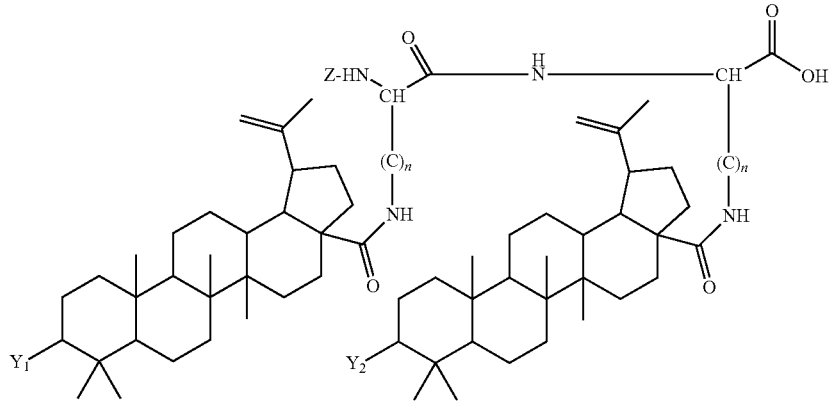

with a compound of the formula

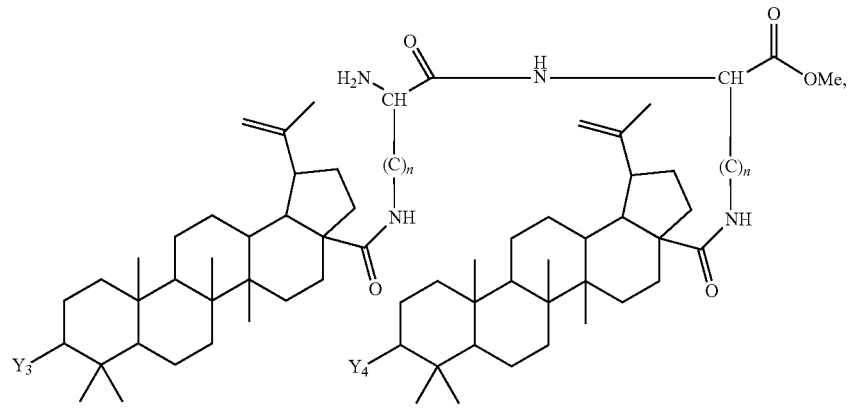

under conditions effective to make the conjugated betulinol derivative tetramer.

Another aspect of the present invention relates to a method of treating HIV-1 infection in a subject. This method involves administering to a subject with HIV-1 infection a therapeutically effective amount of a compound having the formula

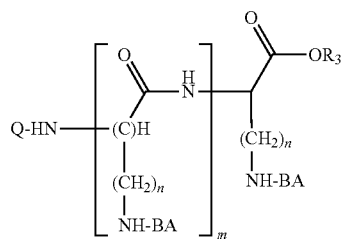

wherein
BA is a compound having the formula:

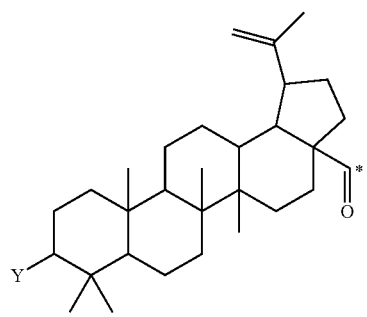

wherein
Y is selected from the group consisting of —$CH_3$, =O, —OH, —$OCH_3$, —$OC(O)CH_3$, —NNH-2,4-DNP, and =S;
* is a binding site;
Q is BA, a leaving group, or H;
$R_3$ is H or $C_1$-$C_5$ alkyl;
n is an integer from 1 to 12; and
m is an integer from 1 to 6,
or a pharmaceutically acceptable salt or derivative thereof, under conditions effective to treat the subject for HIV-1 infection.

In a preferred embodiment, n is an integer from 2 to 8.
Preferably, the above compound has a structure where:
Y is =O, n is 5, and m is 4;
Y is =O, Z is —C(=O)—O-t-buty 1, and n is 4; or
Y is —OH, Z is —C(=O)—O-t-buty 1, and n is 4.

The above method employs a conjugated betulinol derivative polymer compound, which is made by a method that involves polymerizing a monomer of the formula

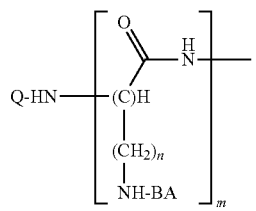

under conditions effective to make the conjugated betulinol derivative polymer compound.

Yet a further aspect of the present invention relates to a method of treating and/or inhibiting HIV-1 infection in a human. This method involves administering to a human infected with HIV-1 a therapeutically effective amount of a compound having the formula

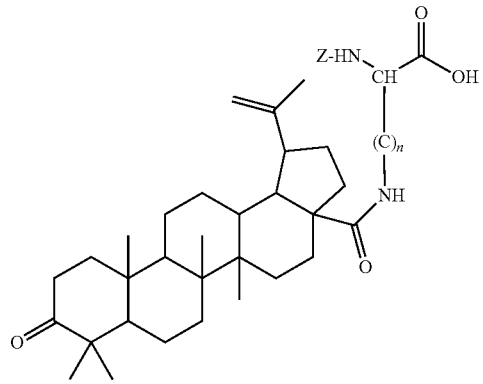

where
n is an integer from 1 to 12 and
Z is H or a protective group,
or a pharmaceutically acceptable salt or derivative thereof, under conditions effective to treat and/or inhibit the human for HIV-1 infection.

In a preferred embodiment, the above compound is administered as a tablet in a dosage range of 1 mg-500 mg.

A further aspect of the present invention relates to a method of treating and/or inhibiting HIV-1 infection in a human. This method involves administering to a human infected with HIV-1 a therapeutically effective amount of a compound having the formula

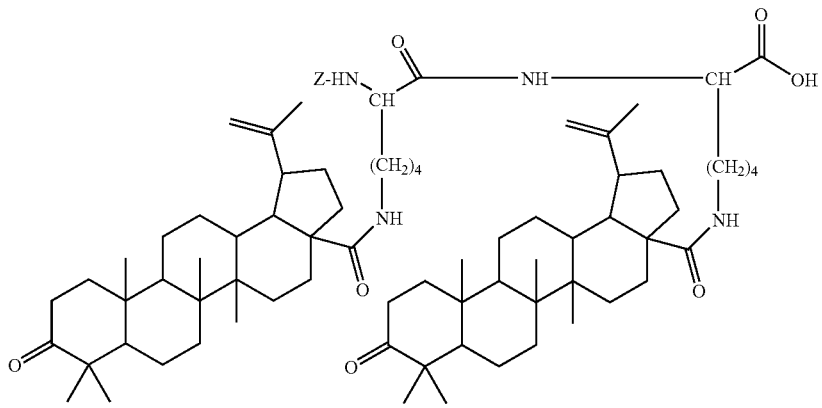

where

Z is H or a protective group,
or a pharmaceutically acceptable salt or derivative thereof, under conditions effective to treat and/or inhibit the human for HIV-1 infection.

In a preferred embodiment, the above compound is administered as a tablet in a dosage range of 1 mg-500 mg.

For purposes of the present invention, the compounds suitable for carrying out the above methods are referred to as conjugated betulinol derivative compounds, and include conjugated betulinol derivative monomers, dimers, tetramers, and polymers. Compounds herein referred to as immunoconjugated betulinol derivative compounds are also suitable for carrying out the methods of the present invention. Immunoconjugated betulinol derivative compounds, including monomers, dimers, tetramers, and polymers are prepared by attaching an antibody directly to a conjugated betulinol derivative compound.

Thus, another aspect of the present invention relates to a method of treating HIV-1 infection in a subject by administering to a subject with HIV-1 infection a therapeutically effective amount of a compound having the formula

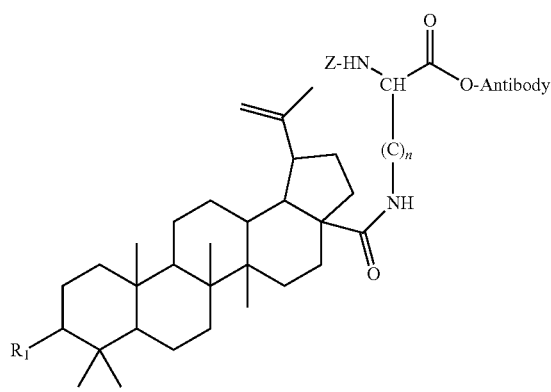

where $R_1$ is selected from the group consisting of $-CH_3$, $=O$, $-OH$, $-OCH_3$, $-OC(O)CH_3$, $-NNH-2,4-DNP$, and $=S$
and n is an integer from 1 to 12; and Z is H or a protective group,
or a pharmaceutically acceptable salt or derivative thereof, under conditions effective to treat the subject for HIV-1 infection.

In a preferred embodiment, $R_1$ is $=O$ and n=4.

A further aspect of the present invention relates to a method of treating HIV-1 infection in a subject. This method involves administering to a subject with HIV-1 infection a therapeutically effective amount of a compound having the formula

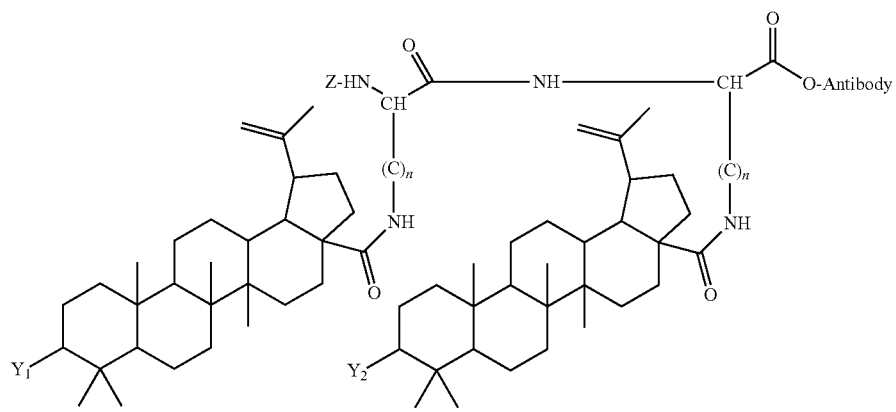

where $Y_1$ and $Y_2$ are independently selected from the group consisting of $-CH_3$, $=O$, $-OH$, $-OCH_3$, $-OC(O)CH_3$, $-NNH-2,4-DNP$, and $=S$;

Z is H or a protective group; and n is an integer from 1 to 12, or a pharmaceutically acceptable salt or derivative thereof, under conditions effective to treat the subject for HIV-1 infection.

In a preferred embodiment, $Y_1$ and $Y_2$ are $=O$ and n=4.

Yet another aspect of the present invention relates to a method of treating HIV-1 infection in a subject. This method involves administering to a subject with HIV-1 infection a therapeutically effective amount of a compound having the formula

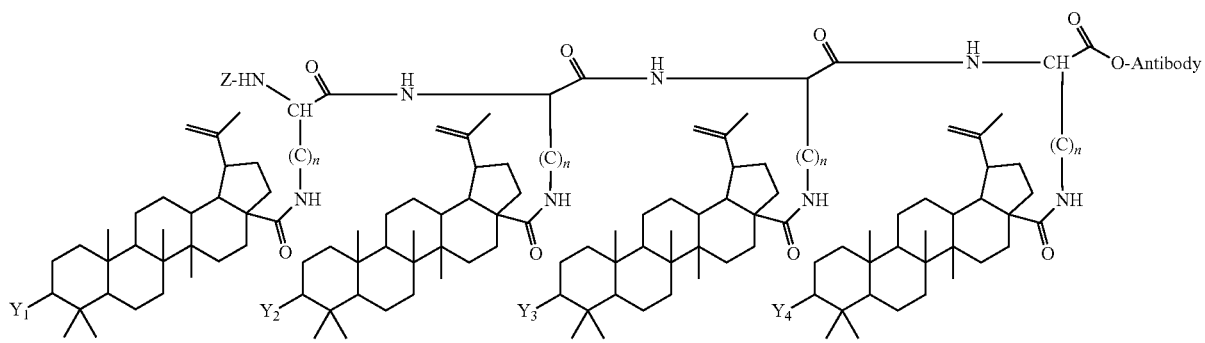

where $Y_1$, $Y_2$, $Y_3$, and $Y_4$ are independently selected from the group consisting of —$CH_3$, =O, —OH, —$OCH_3$, —OC(O)$CH_3$, —NNH-2,4-DNP, and =S;

n is an integer from 1 to 12; and

Z is H or a protective group, or a pharmaceutically acceptable salt or derivative thereof, under conditions effective to treat the subject for HIV-1 infection.

In a preferred embodiment, $Y_1$, $Y_2$, $Y_3$, and $Y_4$ are =O and n=4.

Yet a further aspect of the present invention relates to a method of treating HIV-1 infection in a subject. This method involves administering to a subject with HIV-1 infection a therapeutically effective amount of a compound having the formula

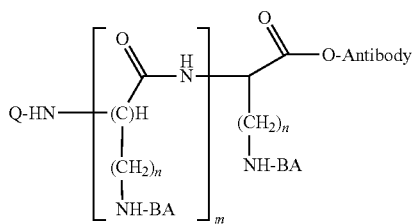

where

BA is a compound having the formula:

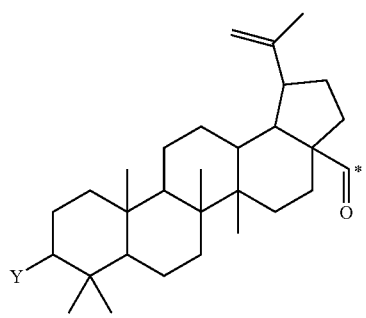

where

Y is selected from the group consisting of —$CH_3$, =O, —OH, —$OCH_3$, —OC(O)$CH_3$, —NNH-2,4-DNP, and =S;

* is a binding site;

Q is BA, a leaving group, or H;

n is an integer from 1 to 12; and m is an integer from 1 to 6, or a pharmaceutically acceptable salt or derivative thereof, under conditions effective to treat the subject for HIV-1 infection.

In a preferred embodiment, Y is =O, n=5, and m=4.

A preferred type of antibody for making the above immunoconjugated betulinol derivative compounds and for use in the above methods is a gammaglobulin. IgG, IgA, IgE, and IgM subclasses are particularly preferred. Some representative immunoglobulins are monoclonal or polyclonal antibodies to human or animal tumor associated antigens; human B- and T-cell antigens; human Ia antigens; viral, fungal and bacterial antigens; and cells involved in human inflammatory or allergic reactions.

Methods for preparing antibodies and monoclonal antibodies to particular haptenic or antigenic target substrates are described in Goding, *Monoclonal Antibodies: Principles and Practice,* 2nd. ed., New York: Academic Press, (1986); Kennett et al., *Monoclonal Antibodies,* New York: Plenum Press (1980); U.S. Pat. No. 4,423,147 to Secher et al.; U.S. Pat. No. 4,381,292 to Bieber et al.; U.S. Pat. No. 4,363,799 to Kung et al.; U.S. Pat. No. 4,350,683 to Galfre et al.; U.S. Pat. No. 4,127,124 to Clagett et al., which are hereby incorporated by reference.

Preferred subjects for treating HIV-1 infection in accordance with the methods of the present invention include, without limitation, any mammal, preferably a human.

In carrying out the methods of treating HIV-1 infection in a subject of the present invention, a therapeutically effective amount of a betulinol derivative compound is preferably administered to the subject to treat the subject for AIDS. Alternatively, the administering step is carried out to prevent AIDS in the subject infected with HIV-1.

As used here, the term "treating" means amelioration, prevention, or relief from the symptoms and/or effects associated with HIV-1 infection, and includes the prophylactic administration of a conjugated or immunoconjugated betulinol derivative compound, or a pharmaceutically acceptable salt or derivative thereof, to substantially diminish the likelihood or seriousness of the condition.

The relative activity, potency, and specificity of the compound may be determined by a pharmacological study in animals, for example, according to the method of Nyberg et al., *Psychopharmacology* 119:345-348 (1995), which is hereby incorporated by reference in its entirety. Although the differential metabolism among patient populations can be determined by a clinical study in humans, less expensive and time-consuming substitutes are provided by the methods of Kerr et al., *Biochem. Pharmacol.* 47:1969-1979 (1994) and Karam et al., *Drub Metab. Discov.* 24:1081-1087 (1996), which are hereby incorporated by reference in their entirety. The potential for drug-drug interactions may be assessed clinically according to the methods of Leach et al., *Epilepsia* 37:1100-1106 (1996), which is hereby incorporated by reference in its entirety, or in vitro according to the methods of Kerr et al., *Biochem. Pharmacol.* 47:1969-1979 (1994) and Turner et al., *Can. J. Physio. Pharmacol.* 67:582-586 (1989), which are hereby incorporated by reference in their entirety.

The magnitude of a prophylactic or therapeutic dose of the compound will vary with the nature and severity of the condition to be treated and the route of administration. The dose, and perhaps the dose frequency, will also vary according to the age, body weight, and response of the individual subject. The total daily dose of compound may be administered in single or divided doses.

The compound should be administered in an effective amount. Exemplary doses of betulinol derivatives for oral administration that provide an effective amount of the betulinol derivative typically range from about 1 mg per unit dose to 2,000 mg per unit dose and more typically from about 10 mg per unit dose to 500 mg per unit dose. Preferably, the dosage is in the range of 1.0 to 200 mg/kg/day and the preferred dosage range is 1.0 to 50 mg/kg/day.

It is further recommended that children, subjects over 65 years old, and those with impaired renal or hepatic function, initially receive low doses and that the dosage be titrated based on individual responses and blood levels. It may be necessary to use dosages outside these ranges in some cases, as will be apparent to those of ordinary skill in the art. Further, it is noted that the clinician or treating physician knows how and when to interrupt, adjust, or terminate therapy in conjunction with and individual subject's response.

Any suitable route of administration may be employed and, may include, without limitation, oral, intradermal, intramuscular, intraperitoneal, intravenous, subcutaneous, or intranasal administration. The agent may be administered alone or with suitable pharmaceutical carriers, and can be in solid or liquid form, such as tablets, capsules, powders, solutions, suspensions, or emulsions. Dosage forms include, for example, tablets, troches, dispersions, suspensions, solutions, capsules, powders, solutions, suspensions, emulsions, and patches.

Pharmaceutical compositions of the present invention include at least one betulinol derivative compound, a pharmaceutically acceptable salt or derivative thereof, or combinations thereof. Such compositions may include a pharmaceutically acceptable carrier, and optionally, other therapeutic ingredients or excipients.

The term "pharmaceutically acceptable salt thereof" refers to salts prepared from pharmaceutically acceptable, non-toxic acids including inorganic acids and organic acids, such as, for example, acetic acid, benzenesulfonic (besylate) acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, and p-toluenesulfonic acid.

The pharmaceutical compositions may be conveniently presented in unit dosage form, and may be prepared by any of the methods well known in the art of pharmacy. Preferred unit dosage formulations are those containing an effective dose, or an appropriate fraction thereof, of the active ingredients.

The compositions of the present invention may include a pharmaceutically acceptable carrier. The carrier may take a wide variety of forms, depending on the forms preparation desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by a standard aqueous or nonaqueous technique. Oral and parenteral sustained release dosage forms may also be used.

Oral syrups, as well as other oral liquid formulations, are well known to those skilled in the art, and general methods for preparing them are found in any standard pharmacy school textbook. For example, chapter 86, of the 19th Edition of *Remington: The Science and Practice of Pharmacy*, entitled "Solutions, Emulsions, Suspensions and Extracts," describes in complete detail the preparation of syrups (pages 1503-1505, which are hereby incorporated by reference in their entirety) and other oral liquids.

Similarly, sustained release formulations are well known in the art, and Chapter 94 of the same reference, entitled "Sustained-Release Drug Delivery Systems," describes the more common types of oral and parenteral sustained-release dosage forms (pages 1660-1675, which are hereby incorporated by reference in their entirety). Because they reduce peak plasma concentrations, as compared to conventional oral dosage forms, controlled release dosage forms are particularly useful for providing therapeutic plasma concentrations while avoiding the side effects associated with high peak plasma concentrations that occur with conventional dosage forms.

The solid unit dosage forms can be of the conventional type. The solid form can be a capsule, such as an ordinary gelatin type containing the betulinol derivative and a carrier, for example, lubricants and inert fillers, such as lactose, sucrose, or cornstarch. In another embodiment, these betulinol derivatives can be tableted with conventional tablet bases, such as lactose, sucrose, or cornstarch, in combination with binders, like acacia, cornstarch, or gelatin, disintegrating agents, such as cornstarch, potato starch, or alginic acid, and lubricants, like stearic acid or magnesium stearate.

The pharmaceutical compositions may also be administered in injectable dosages by solution or suspension of these materials in a physiologically acceptable diluent with a pharmaceutical carrier. Such carriers include sterile liquids, such as water and oils, with or without the addition of a surfactants, adjuvants, excipients, or stabilizers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

For use as aerosols, the pharmaceutical compositions in solution or suspension may be packaged in a pressurized aerosol container together with suitable propellants, for example, hydrocarbon propellants like propane, butane, or isobutane, and with conventional adjuvants. The pharmaceutical compositions may also be administered in a non-pressurized form, such as in a nebulizer or atomizer.

The present invention also relates to methods of inhibiting HIV-1 activity in a cell using betulinol derivative compounds.

Thus, in accordance with one aspect of the present invention, a cell infected with HIV-1 is provided and contacted with a compound having the formula 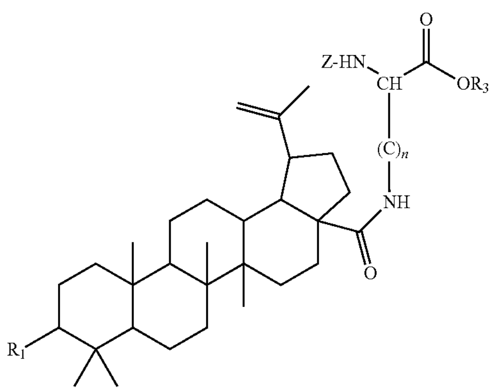 where $R_1$ is selected from the group consisting of —$CH_3$, =O, —OH, —$OCH_3$, —OC(O)$CH_3$, —NNH-2,4-DNP, and =S and $R_3$ is selected from the group consisting of H and $C_1$-$C_5$ alkyl, n is an integer from 1 to 12; and Z is H or a protective group, or a pharmaceutically acceptable salt or derivative thereof, under conditions effective to inhibit HIV-1 activity in the cell.

In a preferred embodiment, n is an integer from 2 to 8.

Preferably, the above compound has a structure where:

$R_1$ is =O, $R_3$ is methyl, and n is 4;

$R_1$ is =O, $R_3$ is H, Z is —C(=O)—O-t-buty 1, and n is 4; or $R_1$ is —OH, $R_3$ is H, Z is —C(=O)—O-t-buty 1, and n is 4.

Another aspect of the present invention relates to a method of inhibiting HIV-1 activity in a cell. This method involves providing a cell infected with HIV-1 and contacting the cell with a compound having the formula 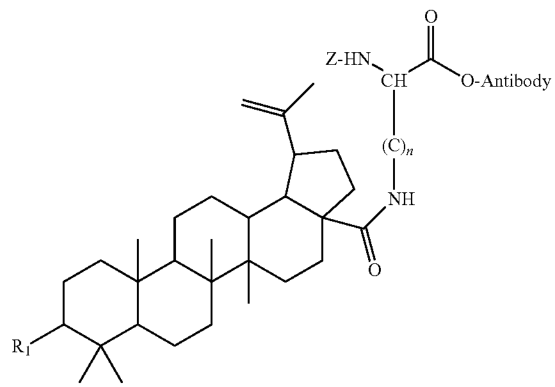 where $R_1$ is selected from the group consisting of —$CH_3$, =O, —OH, —$OCH_3$, —OC(O)$CH_3$, —NNH-2,4-DNP, and =S and n is an integer from 1 to 12; and Z is H or a protective group, or a pharmaceutically acceptable salt or derivative thereof, under conditions effective to inhibit HIV-1 activity in the cell.

In a preferred embodiment, $R_1$ is =O and n=4.

A further aspect of the present relates to a method of inhibiting HIV-1 activity in a cell. This method involves providing a cell infected with HIV-1 and contacting the cell with a compound having the formula where $Y_1$ and $Y_2$ are independently selected from the group consisting of —$CH_3$, =O, —OH, —$OCH_3$, —OC(O)$CH_3$, —NNH-2,4-DNP, and =S;

$R_3$ is selected from the group consisting of H and $C_1$-$C_5$ alkyl;

Z is H or a protective group; and n is an integer from 1 to 12, or a pharmaceutically acceptable salt or derivative thereof, under conditions effective to inhibit HIV-1 activity in the cell.

In a preferred embodiment, n is an integer from 2 to 8.

Preferably, the above compound has a structure where:

$Y_1$ and $Y_2$ are =O, $R_3$ is methyl, and n is 4;

$Y_1$ and $Y_2$ are =O, $R_3$ is H, Z is —C(=O)—O-t-buty 1, and n is 4; or $Y_1$ and $Y_2$ are —OH, $R_3$ is H, Z is —C(=O)—O-t-buty 1, and n is 4.

Yet another aspect of the present invention relates to a method of inhibiting HIV-1 activity in a cell. This method involves providing a cell infected with HIV-1 and contacting the cell with a compound having the formula

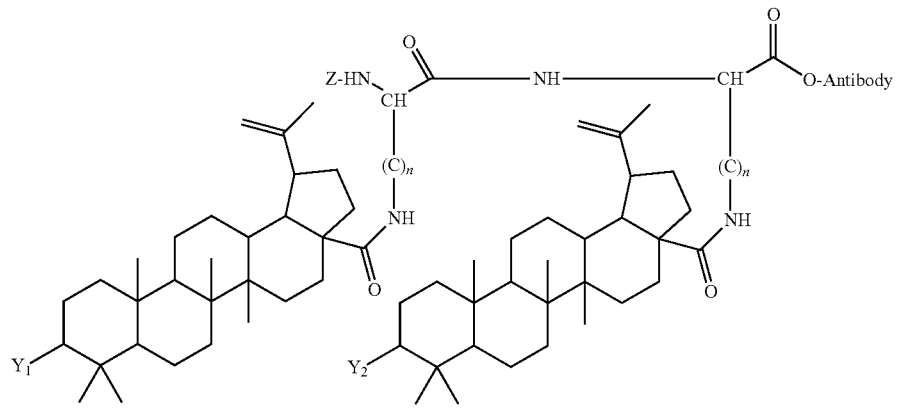

where $Y_1$ and $Y_2$ are independently selected from the group consisting of —CH$_3$, =O, —OH, —OCH$_3$, —OC(O)CH$_3$, —NNH-2,4-DNP, and =S;

Z is H or a protective group; and n is an integer from 1 to 12, or a pharmaceutically acceptable salt or derivative thereof, under conditions effective to inhibit HIV-1 activity in the cell.

In a preferred embodiment, $Y_1$ and $Y_2$ are =O and n=4.

Yet a further aspect of the present invention relates to a method of inhibiting HIV-1 activity in a cell. This method involves providing a cell infected with HIV-1 and contacting the cell with a compound having the formula where $Y_1$, $Y_2$, $Y_3$, and $Y_4$ are independently selected from the group consisting of —CH$_3$, =O, —OH, —OCH$_3$, —OC(O)CH$_3$, —NNH-2,4-DNP, and =S;

$R_3$ is selected from the group consisting of H and $C_1$-$C_5$ alkyl;

n is an integer from 1 to 12; and

Z is H or a protective group, or a pharmaceutically acceptable salt or derivative thereof, under conditions effective to inhibit HIV-1 activity in the cell.

In a preferred embodiment, n is an integer from 2 to 8.

Preferably, the above compound has a structure where:

$Y_1$, $Y_2$, $Y_3$, and $Y_4$ are =O, $R_3$ is methyl, and n is 4;

$Y_1$, $Y_2$, $Y_3$, and $Y_4$ are =O, $R_3$ is H, Z is —C(=O)—O-t-buty 1, and n is 4; or $Y_1$, $Y_2$, $Y_3$, and $Y_4$ are —OH, $R_3$ is H, Z is —C(=O)—O-t-buty 1, and n is 4.

Another aspect of the present invention relates to a method of inhibiting HIV-1 activity in a cell. This method involves providing a cell infected with HIV-1 and contacting the cell with a compound having the formula

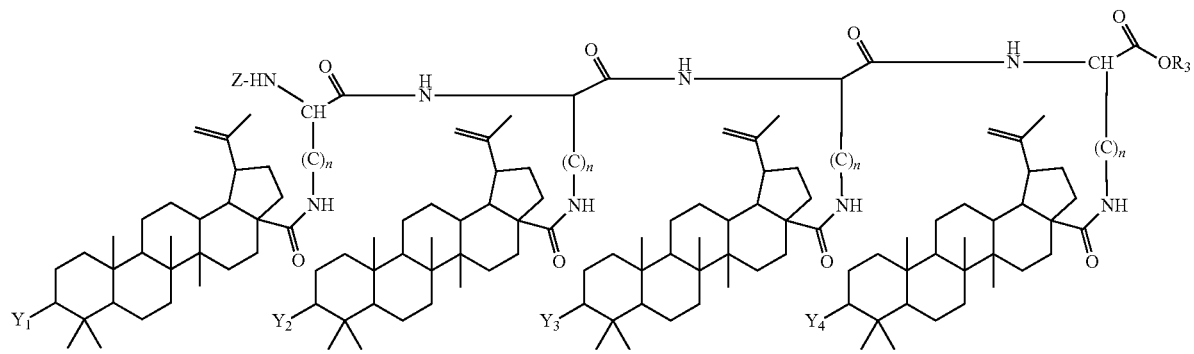

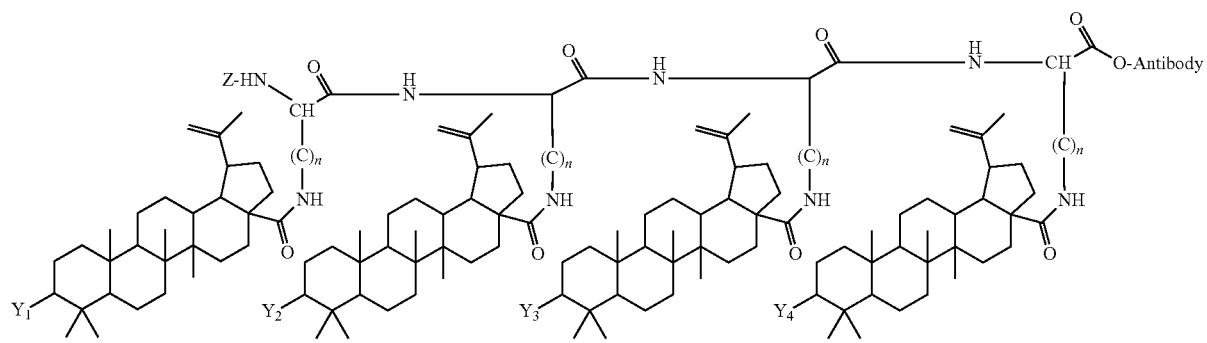

where
$Y_1$, $Y_2$, $Y_3$, and $Y_4$ are independently selected from the group consisting of —$CH_3$, =O, —OH, —$OCH_3$, —OC(O)$CH_3$, —NNH-2,4-DNP, and =S;
n is an integer from 1 to 12; and
Z is H or a protective group,
or a pharmaceutically acceptable salt or derivative thereof, under conditions effective to inhibit HIV-1 activity in the cell.
In a preferred embodiment, $Y_1$, $Y_2$, $Y_3$, and $Y_4$ are =O and n=4.

A further aspect of the present invention relates to a method of inhibiting HIV-1 activity in a cell. This method involves providing a cell infected with HIV-1 and contacting the cell with a compound having the formula

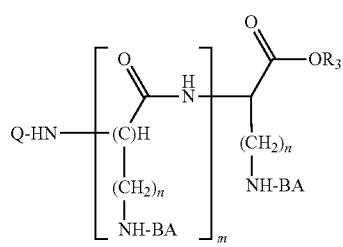

wherein
BA is a compound having the formula:

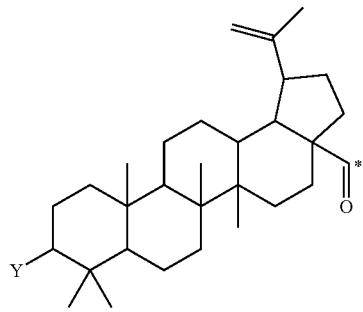

wherein
Y is selected from the group consisting of —$CH_3$, =O, —OH, —$OCH_3$, —OC(O)$CH_3$, —NNH-2,4-DNP, and =S;
* is a binding site;
Q is BA, a leaving group, or H;
$R_3$ is H or $C_1$-$C_5$ alkyl;
n is an integer from 1 to 12; and
m is an integer from 1 to 6, or a pharmaceutically acceptable salt or derivative thereof, under conditions effective to inhibit HIV-1 activity in the cell.
In a preferred embodiment, n is an integer from 2 to 8.
Preferably, the above compound has a structure where:
Y is =O, n is 5, and m is 4;
Y is =O, Z is —C(=O)—O-t-buty 1, and n is 4; or
Y is —OH, Z is —C(=O)—O-t-buty 1, and n is 4.

Yet another aspect of the present invention relates to a method of inhibiting HIV-1 activity in a cell. This method involves providing a cell infected with HIV-1 and contacting the cell with a compound having the formula

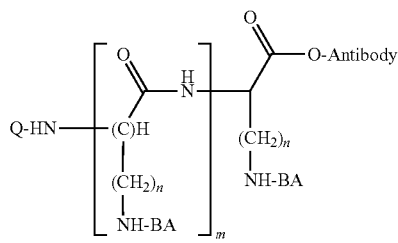

where
BA is a compound having the formula:

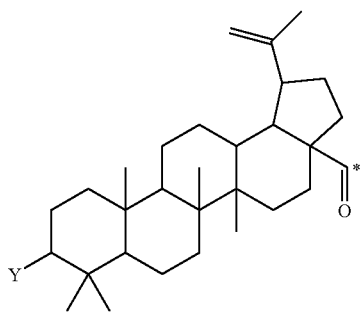

where
Y is selected from the group consisting of —$CH_3$, =O, —OH, —$OCH_3$, —OC(O)$CH_3$, —NNH-2,4-DNP, and =S;
* is a binding site;
Q is BA, a leaving group, or H;
n is an integer from 1 to 12; and
m is an integer from 1 to 6,
or a pharmaceutically acceptable salt or derivative thereof, under conditions effective to inhibit HIV-1 activity in the cell.
In a preferred embodiment, Y is =O, n=5, and m=4.

In carrying out the methods of inhibiting HIV-1 activity in a cell of the present invention, "contacting" can be carried out as desired, including, but not limited to, contacting cells in culture in a suitable growth medium. Alternatively, mice, rats or other mammals are injected with compounds.

Other betulinol derivative compounds are also amenable to the methods of the present invention. In particular, betulinol derivatives with increased solubility may be achieved by a variety of other methods besides preparation of the above-described conjugates and immunoconjugates. In one preferred embodiment, increased solubility of a betulinol derivative compound is achieved by attaching a solubilizing agent at C28 or C3 of the betulin derivative. Preferred solubilizing agents include, without limitation, polyethylene glycol (PEG) or miniPEGs. PEG chemistry is well known and can be used to attach the PEG to the betulin derivative.

By another preferred embodiment, preferred betulinol derivative compounds with increased solubility are achieved by employing hydrophilic amino acids. Specifically, the hydrophilic basic amino acids (Lys, Arg, or His) can attach to the betulinol derivatives. The other highly hydrophilic amino acids (Glu, Asp, Gln, or Asn) may also be used. Di-peptides, for example, Lys-Lys, Lys-His, Lys-Arg, Arg-His, Lys-Glu, Arg-Gln, Lys-Gln, and tri-peptides may be used to enhance the solubility of the betulinol derivative. Additionally, the di-peptides and tri-peptides may include amino acids that are mildly hydrophilic in character (Tyr, Trp, Ser, Thr, and Gly). The coupling of these peptides may occur in a hindered position, allowing the hydrophilic portion of the peptides to remain available for solvation.

The coupling of peptides, including a lysine residue, can be carried out in a manner similar to that disclosed herein for coupling lysine to a betulinol derivative with the addition of, for example, a reaction step that serves to protect the active group on the other residue(s). Similarly, amino acids or peptides containing amino acid residues having a primary or secondary amine (i.e., Arg and His) can be attached to the betulinol derivative in a manner similar to that disclosed herein for the lysine conjugation. The chemistry for forming other amino acid or peptide conjugates is well known to those skilled in the art.

In yet another preferred embodiment, polyamines such as spermidine, putrescine, and spermine may be attached to the betulinol derivative to increase solubility. These compounds are attached through a primary or secondary amine group.

Carbohydrate moieties including (1) monosaccharides (e.g. glucose, galactose, fucose, and fructose), (2) disaccharides (e.g., sucrose and maltose), and (3) aminosugars (e.g., glucosamine, galactosamine, 2-amino-2-deoxy-glucuronic acid, 2-amino-2-deoxy-glucose, 2-amino-2-deoxy-3-O-â-D-glucopyranurosyl-D-galactose, galactonojirimycin, gluconojirimycin, and derivatives thereof) may also be attached to betulinol derivatives to increase solubility. Cyclodextrins, including, for example, 2-amino-2-deoxy-3-O-β-D-glucopyranurosyl-D-galactose, α-cyclodextrin (six glucose residues); β-cyclodextrin (seven glucose residues); and γ-cyclodextrin (eight glucose residues) may be attached to the betulin derivative to increase solubility.

The coupling of a carbohydrate to the betulinol derivative can be done by the methods known in the art of carbohydrate chemistry.

Increased solubility of betulinol derivative compounds may also be achieved by attaching a betulinol derivative to each of 4 glycine chains having around 2-3 glycine molecules of a sugar molecule (or 2 betulonic acid groups in the case of lysine), leaving one OH group open to attach to an antibody. In a preferred embodiment, glycine chains are used due to increased solubility in organic solution and to avoid hinderance. An exemplary structure is as follows:

where

BA∿O is BA-amino acid-O;

BA is a compound having the formula where

Y is selected from the group consisting of —CH$_3$, =O, —OH, —OCH$_3$, —OC(O)CH$_3$, —NNH-2,4-DNP, and =S and

* is a binding site to facilitate attachment of BA to the exemplary structure.

Alternatively, instead of leaving an OH group to bond to an antibody, it may be attached to a lipid. An exemplary structure is as follows:

where

BA∿O is BA-amino acid-BA;

BA is a compound having the formula where

Y is selected from the group consisting of —CH$_3$, =O, —OH, —OCH$_3$, —OC(O)CH$_3$, —NNH-2,4-DNP, and =S;

* a binding site to facilitate attachment of BA to the exemplary structure;

p is an integer from 1 to 10;

n is an integer from 1 to 6; and m is an integer from 1 to 6.

Although there will be no conjugation with an antibody, the whole compound is water-soluble. Also, there will be no toxicity since the entire compound is biocompatible.

In another preferred embodiment, a long chain with $NH_2$ and COOH groups may be employed, alternating with an OH group at the end. These structure are achieved by attaching a betulinol derivative compound to $NH_2$ groups. The OH group can then be used to attach to an antibody. An exemplary structure is as follows:

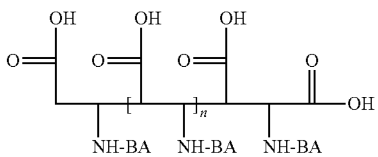

where BA is a compound having the formula 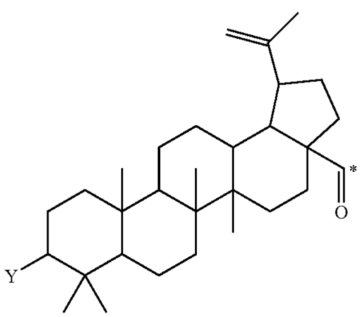 where

Y is selected from the group consisting of —$CH_3$, ═O, —OH, —$OCH_3$, —OC(O)$CH_3$, —NNH-2,4-DNP, and ═S;

* a binding site to facilitate attachment of BA to the exemplary structure; and n is an integer from 1 to 6.

Different ratios of carboxylic acid to the amine on the chain may be employed.

Another aspect of the present invention relates to a method of treating and/or inhibiting HIV-1 infection in a subject. This method involves administering to a subject infected with HIV-1 a therapeutically effective amount of a compound having the formula:

where

BA is a compound having the formula:

where

Y is selected from the group consisting of —$CH_3$, ═O, —OH, —$OCH_3$, —OC(O)$CH_3$, —NNH-2,4-dinitrophenyl hydrazine, and ═S;

* is a binding site;

X is selected from the group consisting of 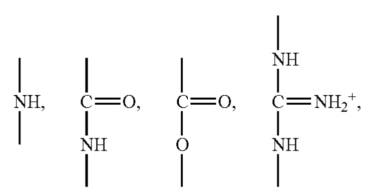 and 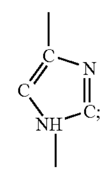 each $R_4$ is independently selected from the group consisting of H, $CH_3$, $CH_2$—$CH_3$, $NH_2$ and OH;

Z is H, a protective group, or BA;

n is an integer from 1 to 8;

m is an integer from 1 to 6; and q is 0 or 1, or a pharmaceutically acceptable salt thereof.

Yet another aspect of the present invention relates to a method of treating HIV-1 infection in a subject. This method involves administering to a subject infected with HIV-1 a therapeutically effective amount of a compound having the formula:

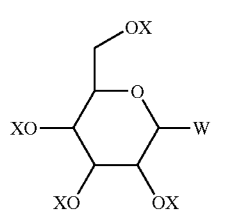

or 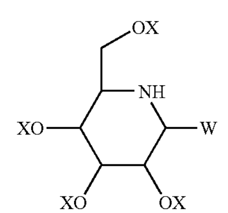 where

W is H, OX, or $CH_2$—OX; and each X is independently H, a sugar, or BA, and wherein at least 1 X is BA; and BA is a compound having the formula:

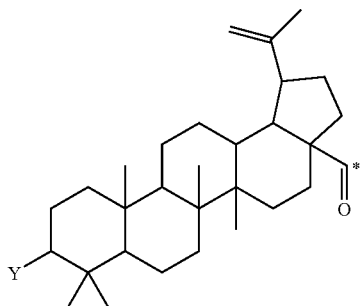

where
  Y is selected from the group consisting of —CH$_3$, =O, —OH, —OCH$_3$, —OC(O)CH$_3$, —NNH-2,4-dinitrophenyl hydrazine, and =S; and
  * is a binding site,
or a pharmaceutically acceptable salt thereof.

Yet a further aspect of the present invention relates to a method of treating HIV-1 infection in a human. This method involves administering to a human infected with HIV-1 a therapeutically effective amount of a compound having the formula:

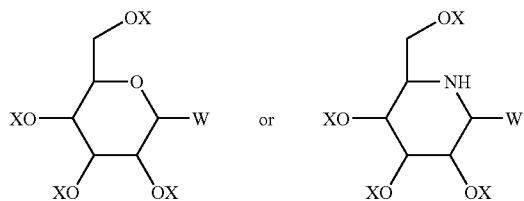

where
  W is H, OX, or CH$_2$—OX; and
  each X is independently H, a sugar, or BA, and wherein at least 1 X is BA; and
BA is a compound having the formula:

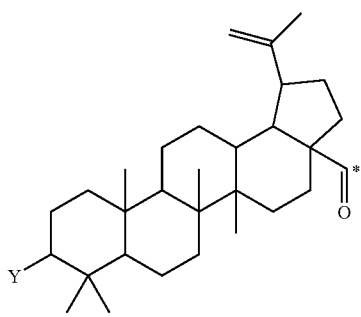

where
  Y is selected front the group consisting of —CH$_3$, =O, —OH, —OCH$_3$, —OC(O)CH$_3$, —NNH-2,4-dinitrophenyl hydrazine, and =S; and
  * is a binding site,
or a pharmaceutically acceptable salt thereof under conditions effective to treat the human for HIV-1 infection.

Still another aspect of the present invention relates to a method of treating HIV-1 infection in a subject. This method involves administering to a subject infected with HIV-1 a therapeutically effective amount of a compound having the formula:

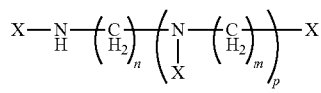

where
  each X is H or a compound of the formula:

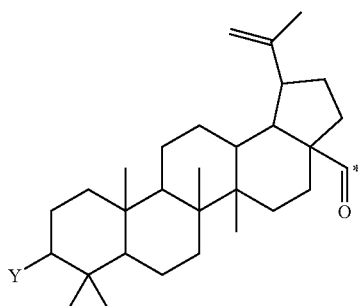

where
  Y is selected from the group consisting of —CH$_3$, =O, —OH, —OCH$_3$, —OC(O)CH$_3$, —NNH-2,4-dinitrophenyl hydrazine, and =S;
  * is a binding site,
  n is an integer from 1 to 8;
  p is 0 or 1; and
  m is an integer from 1 to 8;
wherein at least one X is not H,
or a pharmaceutically acceptable salt thereof.

Still a further aspect of the present invention relates to a method of treating HIV-1 infection in a human. This method involves administering to a human infected with HIV-1 a therapeutically effective amount of a compound having the formula:

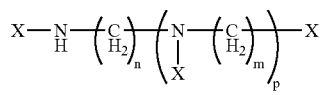

where
  each X is H or a compound of the formula:

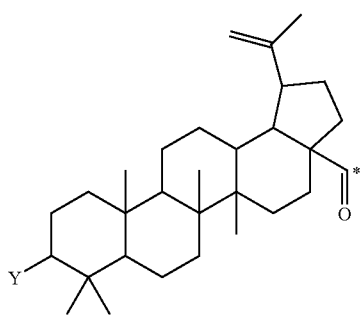

where

Y is selected from the group consisting of —CH₃, =O, —OH, —OCH₃, —OC(O)CH₃, —NNH-2,4-dinitrophenyl hydrazine, and =S;

\* is a binding site, n is an integer from 1 to 8;

p is 0 or 1; and m is an integer from 1 to 8;

wherein at least one X is not H, or a pharmaceutically acceptable salt thereof under conditions effective to treat the human for HIV-1 infection.

Another aspect of the present invention relates to a method of treating HIV-1 infection in a subject. This method involves administering to a subject infected with HIV-1 a therapeutically effective amount of a compound having the formula:

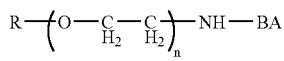

where

R is a $C_1$ to $C_5$ alkyl;

n is an integer between 5 and 1000; and

BA is a compound having the formula:

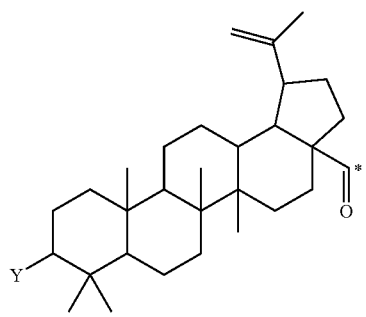

where

Y is selected from the group consisting of —CH₃, =O, —OH, —OCH₃, —OC(O)CH₃, —NNH-2,4-dinitrophenyl hydrazine, and =S; and \* is a binding site, or a pharmaceutically acceptable salt thereof.

A further aspect of the present invention relates to a method of treating HIV-1 infection in a human. This method involves administering to a human infected with HIV-1 a therapeutically effective amount of a compound having the formula:

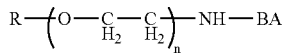

where

R is a $C_1$ to $C_5$ alkyl;

n is an integer between 5 and 1000; and

BA is a compound having the formula:

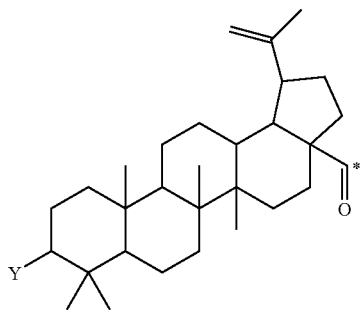

where

Y is selected from the group consisting of —CH₃, =O, —OH, —OCH₃, —OC(O)CH₃, —NNH-2,4-dinitrophenyl hydrazine, and =S; and \* is a binding site, or a pharmaceutically acceptable salt thereof under conditions effective to treat the human for HIV-1 infection.

EXAMPLES

The examples below are intended to exemplify the practice of the present invention but are by no means intended to limit the scope thereof.

Example 1

Isolation and Structure of Betulinol and Its Derivatives

Betulinol is isolated from the non-saponofiable fraction of the crude sulfate soap prepared by boiling the outer bark of the white birch tree in NaOH, $Na_2SO_4$, $Na_2SO_3$, and $Na_2S_2O_3$ at 110-120° C. Betulinol is then crystallized by using solvents such as acetone, ethyl acetate, isopropanol, butanol, ethanol, etc. The chemical structure of betulinol is:

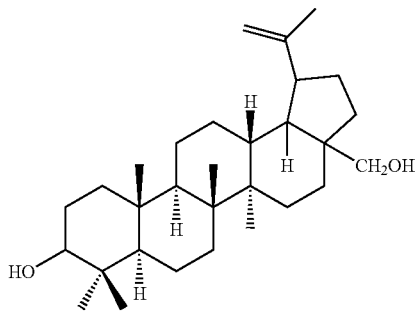

Betulinol is a non-steroidal, lupeol-derived, pentacyclical, lupan-row alcohol of the group of styrenes. Betulinol (also known as betulin) has a chemical formula of $C_{30}H_{50}O_2$ and a molecular weight of 442.7 g/mol. The structure of betulinol is based on a 30-carbon skeleton of four, six-member rings and one, five-member E-ring containing an a-isopropyl group. The structural component of betulinol has a primary and a secondary hydroxyl group at C-3 and C-28. Betulinol has three sites (C-3, C-20, and C-28) where chemical modification can occur to yield derivatives. With the availability of betulinol and its ability to react with various other organic compounds, eleven derivatives of betulinol were synthesized as shown in Scheme 1.

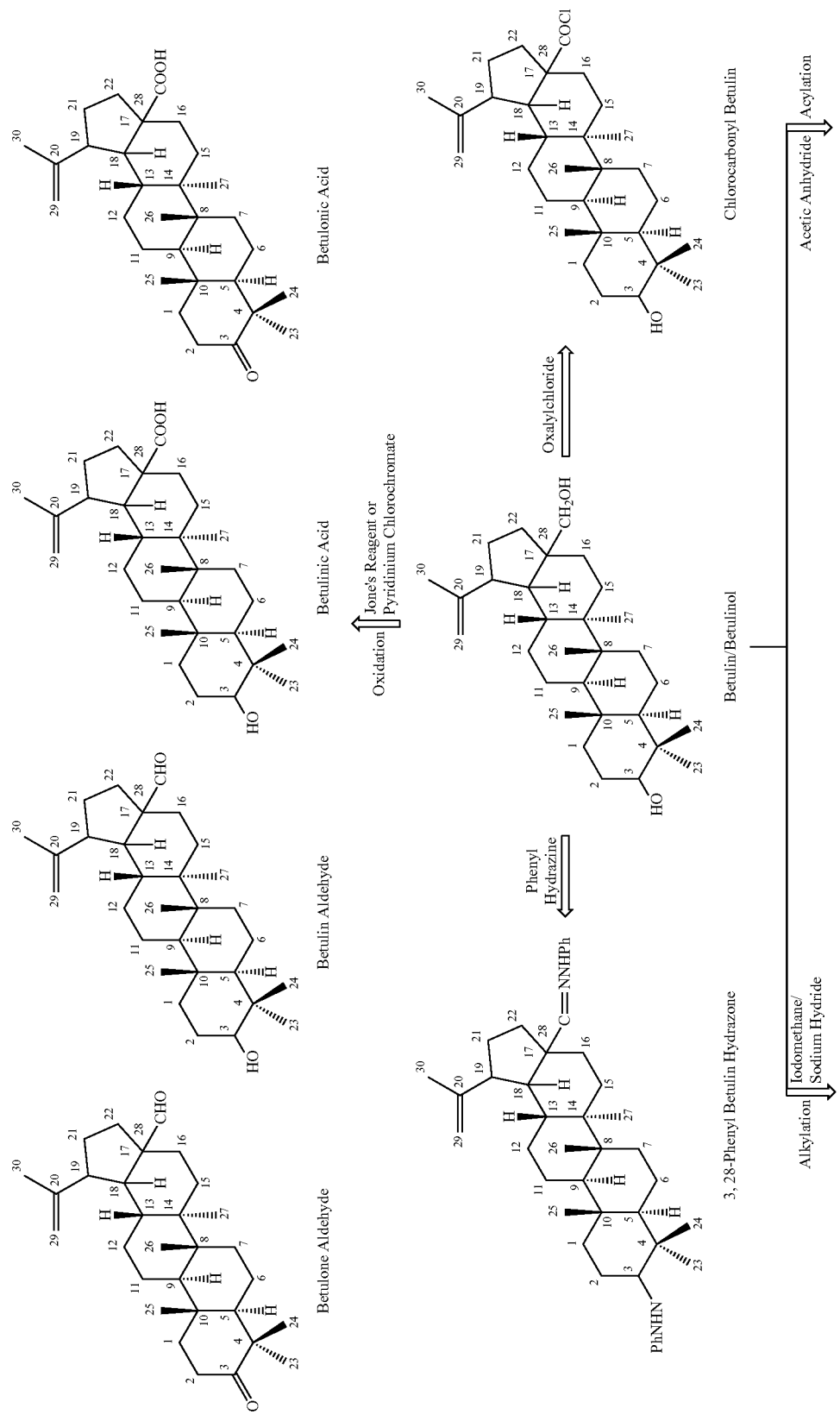

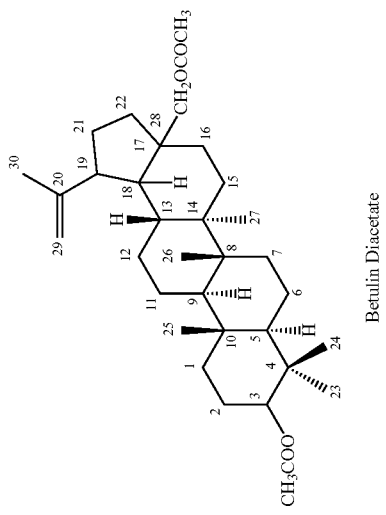# Betulin Diacetate
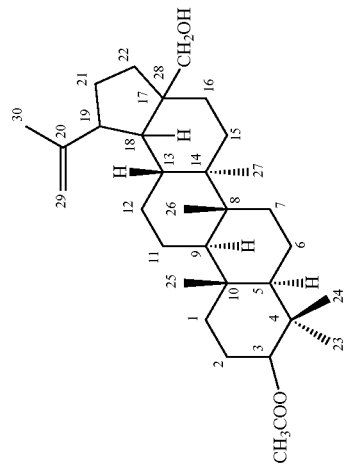# 3-Acetoxy Betulin
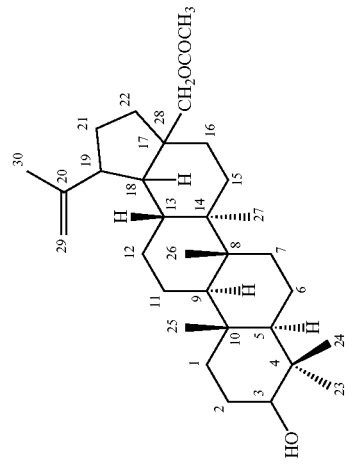# 28-Acetoxy Betulin
-continued
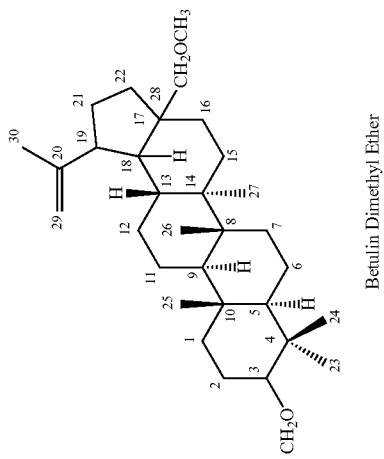# Betulin Dimethyl Ether The alkylated betulinol derivatives can be prepared in a variety of ways. Keto-derivatives can be acquired by treating betulinol with suitable oxidizing reagent, such as Jone's reagent or pyridinium chlorochromate (PCC) (Kim et al., *Synthetic Communications* 27:1607-1612 (1997); Komissarova et al., *Chemistry of National Compounds* 38:58-61 (2002); Ito et al., *J. Nat. Prod.* 64:1278-1281 (2001), which are hereby incorporated by reference in their entirety). In a preferred method, betulinol is first dissolved in acetone, and then oxidized with oxidizing reagent at 0° C. to synthesize carbonyl derivatives of betulinol, such as betulone aldehyde, betulin aldehyde, betulonic acid, and betulonic acid. Betulin acetate derivatives betulin diacetate, 3-acetoxy betulin, and 28-acetoxy betulin were prepared by acylation reaction (Kim et al., *Bioorg. Med. Chem. Lett.,* 8:1707-1712 (1998); Hiroya et al., *Bioorg. Med. Chem.* 10:3229-3236 (2002), which are hereby incorporated by reference in their entirety). In particular, a dry pyridine solution of betulinol was treated with anhydrous acetic anhydride and stirred for 6 hrs. The workup of the resulting mixture was done by diluting with ethyl acetate and washed with 10% HCl and saturated $NaHCO_3$ to yield betulin diacetate, 3-acetoxy betulin, and 28-acetoxy betulin. Betulin dimethyl ether was prepared by alkylation. To a solution of NaOH and betulinol in dry tetrahydrofuran, iodomethane was added and the resulting mixture was refluxed for 40 hrs. Distilled water was added drop wise to stop the reaction. Betulin dimethylether was obtained after column chromatography. Chlorocarbonyl betulin was obtained by treatment with oxalyl chloride (Sun et al., *J. Med. Chem* 45:4271-4275 (2002), which is hereby incorporated by reference in its entirety). A solution of oxalyl chloride was added to betulinic acid and stirred for 2 hrs. Most of the solvent was removed under vacuo. Additional dry $CH_2Cl_2$ was added and subsequently concentrated to yield chlorocarbonyl betulin.

Example 2

Synthesis of Betulonic Acid from Betulinol

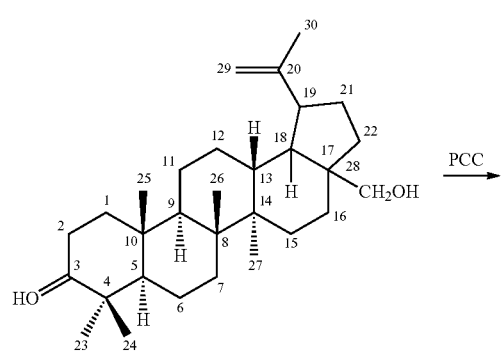

Betulin/Betulinol

1

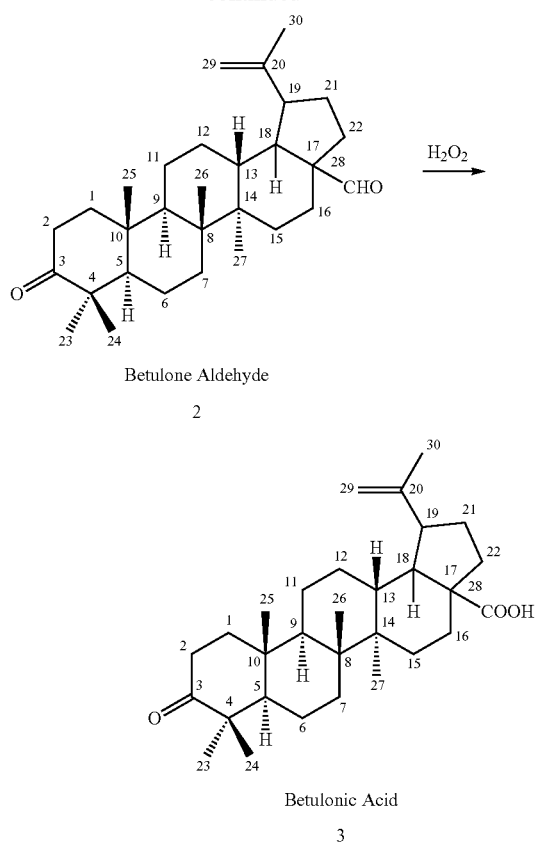

Betulone Aldehyde

2

Betulonic Acid

3

In a typical procedure, 500 mg of betulinol (1) was added to a suspension of 1.2 g of freshly activated 4 Å molecular sieves, 1.2 g of celite, 1.2 g of florisil, 500 mg of sodium acetate, and 1.2 g of pyridinium chlorochromate in 25 mL of $CH_2Cl_2$. The mixture was stirred for 2 hrs, and then filtered through a 2.5×15 cm column silica gel of 230-400 mesh and 60 Å (HF-254, E. Merck). The filtrate was evaporated in vacuum. The residue was subjected to column chromatography of silica gel to recover 370 mg of betulone aldehyde (2) as white solid. This betulone aldehyde was dissolved in 17 mL $CH_3CN$—$H_2O$ containing 877 mg of $NaH_2PO_4.H_2O$ and cooled to 0-5° C. 220 µL of 30% of aqueous $H_2O_2$ and 200 mg of $NaClO_2$ dissolved in 16 mL water were added in tandem. The mixture was brought up to room temperature and stirred for one hour. The reaction was quenched by the addition of 380 mg of $Na_2S_2O_5$. The betulonic acid was extracted with 300 mL ethyl acetate. The organic extract was washed with water and brine, and dried by 100 mg of $Na_2SO_4$. The organic solution was filtered through filter paper and the filtrate was evaporated. The residue was subjected to silica gel column chromatography to recover 347 mg of betulonic acid (3) as white solid powder. The yield and activities of betulonic acid prepared by the above method were compared with the betulonic acid prepared by the Jones reagent (Kim et al., *Synthetic Communications* 27:1607-1612 (1997), which is hereby incorporated by reference in its entirety).

Example 3

Results of Chemistry Characterizations: GC

The purity of betulonic acid and its derivatives was studied by taking gas chromatographic profiles. 8 µL of each sample was injected to yield the following retention time ($t_R$):

TABLE 2

Retention Times from Gas Chromatogram Profiles

| Sample | Retention Time ($t_R$) |
| --- | --- |
| Betulonic Acid | 11.044 |
| Monomer | 10.936 |
| Dimer | 10.793 |

Figure 1B:
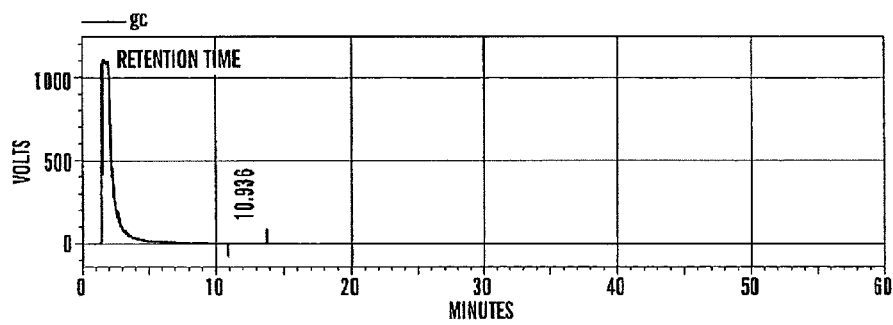
Figure 1C:
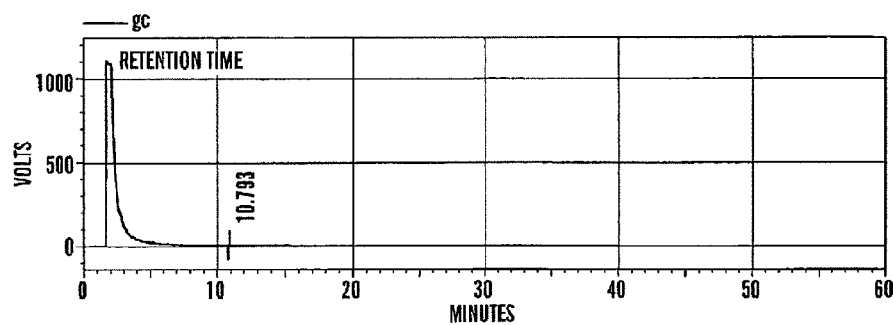

FIGS. 1A-C show a typical chromatogram of betulonic acid and its derivatives with their corresponding retention time. Close examination of these chromatograms reveals that the conjugated betulonic acid monomer and dimer, gave neat chromatograms.

Example 4

Spectroscopic Analysis

Table 3 summarizes the NMR shifts for the synthesized betulonic acid derivatives.

TABLE 3

NMR Chemical Shifts of Betulonic Acid Derivatives

| Betulinol Derivative | $^1$H NMR (500 MHz, CDCl$_3$) | $^{13}$C NMR (500 MHz, CDCl$_3$) |
| --- | --- | --- |
| Betulonic Acid | δ 0.93, 0.97, 0.99, 1.01, 1.07 (15 H, 3 H each, all s, H-23-27), 1.2-1.6 (16 H, m, H-1,5-7,9,11,12,15,16,21,22), 1.7 (3 H, s, H-30), 1.8-2.0 (3 H, m, H-1,18,21), 2.2-2.3 (3 H, m, H-2,16,22), 2.4-2.5 (2 H, m, H-2,13), 3.0 (1 H, dt, J = 5, 11 Hz, H-19), 4.6 (1 H, s, H-29), 4.7 (1 H, s, H-29) | δ 14.8 (C-27), 16.0 (C-26), 16.2 (C-25), 19.6 (C-30), 19.8 (C-6), 21.2 (C-24), 21.5 (C-11), 26.8 (C-12,23), 30.7 (C-15,21), 32.3 (C-16), 33.7 (C-7), 34.3 (C-2), 37.1 (C-10), 37.2 (C-22), 38.7 (C-13), 37.8 (C-1,8), 42.6 (C-14), 47.5 (C-18), 49.3 (C-4), 50.0 (C-9,19), 55.0 (C-5), 56.6 (C-17), 110.0 (C-29), 150.5 (C-20), 183.1 (C-28), 218.6 (C-3) |
| Monomer Ester | δ 0.85, 0.89, 0.94, 0.98 (15 H, all s, H-23-27), 1.1-1.5 (18 H, m, H-1,5-7,9,11,12,15,16,18,21,22,33), 1.36 (9 H, brs, H-40), 1.60 (3 H, s, H-30), 1.6-1.8 (4 H, m, H-1,16,21,22), 1.8-2.0 (4 H, m, H-32,34), 2.2-2.3 (1 H, m, H-2), 2.3-2.5 (2 H, m, H-2,13), 3.0-3.1 (1 H, dt, J = 4, 11 Hz, H-19), 3.10-3.15 (1 H, m, H-31), 3.15-3.21 (1 H, m, H-31), 3.66 (3 H, s, H-37), 4.20 (1 H, m, H-35), 4.51 (1 H, s, H-29), 4.65 (1 H, s, H-29), 5.11 (1 H, d, J = 8 Hz, H-42), 5.88 (1 H, t, J = 5 Hz, H-41) | δ 14.5 (C-27), 15.9 (C-26), 16.0 (C-25), 19.5 (C-30), 19.6 (C-6), 21.0 (C-24), 21.5 (C-33), 22.8 (C-11), 25.6 (C-12), 26.6 (C-23), 28.3 (C-40), 29.4 (C-15), 30.8 (C-21,32), 32.4 (C-34), 33.6 (C-7), 33.7 (C-16), 34.1 (C-2), 36.9 (C-10), 37.7 (C-13), 38.4 (C-22), 38.8 (C-1), 39.6 (C-8), 40.7 (C-31), 42.5 (C-14), 46.6 (C-19), 47.3 (C-4), 50.0 (C-9), 50.1 (C-18), 52.2 (C-37), 53.3 (C-35), 54.9 (C-5), 55.5 (C-17), 79.8 (C-39), 109.4 (C-29), 150.9 (C-20), 155.4 (C-38), 73.2 (C-36), 176.1 (C-28), 218.2 (C-3) |
| Monomer | δ 0.94, 0.99, 1.00, 1.04, 1.09 (15 H, 3 H each, all s, H-23-27), 1.3-1.6 (18 H, m, H-1,5-7,9,11,12,15,16,18,21,22,33), 1.47 (9 H, brs, C-39), 1.70 (3 H, s, H-30), 1.70-1.75 (4 H, m, H-1,16,21,22), 1.90-1.98 (4 H, m, H-32,34), 2.39-2.44 (1 H, m, H-2), 2.44-2.55 (2 H, m, H-2,13), 3.12 (1 H, dt, J = 3.5, 10.8 Hz, H-19), 3.22-3.32 (2 H, m, H-31), 4.31 (1 H, m, H-35), 4.62 (1 H, s, H-29), 4.76 (1 H, s, H-29), 5.17 (1 H, d, J = 7 Hz, H-41), 5.80 (1 H, m, H-40) | δ 14.8 (C-27), 16.1 (C-26), 16.2 (C-25), 19.7 (C-30), 19.8 (C-6), 21.2 (C-24), 21.7 (C-33), 22.8 (C-11), 25.8 (C-12), 26.8 (C-23), 28.5 (C-39), 29.6 (C-15), 31.0 (C-21,32), 32.2 (C-34), 33.9 (C-7), 34.0 (C-16), 34.4 (C-2), 37.1 (C-10), 38.0 (C-13), 38.7 (C-22), 39.1 (C-1), 39.8 (C-8), 40.9 (C-31), 42.7 (C-14), 46.9 (C-19), 47.6 (C-4), 50.2 (C-9,18), 53.8 (C-35), 55.2 (C-5), 55.8 (C-17), 80.8 (C-38), 110.0 (C-29), 151.4 (C-20), 156.4 (C-37), 176.1 (C-28), 177.1 (C-36), 218.2 (C-3) |

TABLE 3-continued

NMR Chemical Shifts of Betulonic Acid Derivatives

| Betulinol Derivative | $^1$H NMR (500 MHz, CDCl$_3$) | $^{13}$C NMR (500 MHz, CDCl$_3$) |
|---|---|---|
| 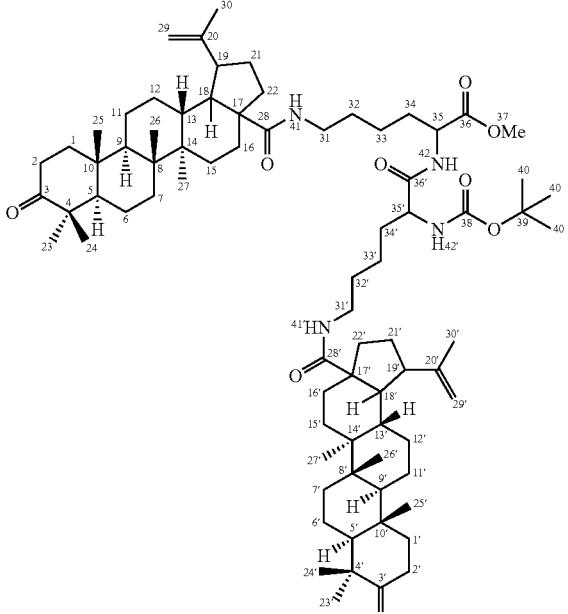<br>Dimer Ester | δ 0.89, 0.91, 0.92, 0.93, 0.97, 0.98, 1.02, 1.03, 1.06, 1.08 (30 H, 3 H each, all s, H-23-27,23'-27'), 1.3-1.6 (38 H, m, H-1,1',5-7,5'-7',9,9',11,11',12,12',15,15',16,16',18,18',21,21',22,22',33,33'), 1.45 (9 H, brs, H-40), 1.68 (6 H, s, H-30,30'), 1.70-1.75 (8 H, m, H-1,1',16,16',21,21',22,22'), 1.90-1.98 (8 H, m, H-32,32',34,34'), 2.39-2.44 (2 H, m, H-2,2'), 2.44-2.55 (4 H, m, H-2,2',13,13'), 3.12 (2 H, dt, J = 3.5, 10.8 Hz, H-19,19'), 3.22-3.32 (4 H, m, H-31,31'), 3.73 (3 H, s, H-37), 4.31 (1 H, m, H-35), 4.55 (1 H, m, H-35'), 4.59 (2 H, s, H-29,29'), 4.73 (2 H, s, H-29,29'), 5.18 (1 H, d, J = 7 Hz, H-42'), 5.85 (2 H, t, J = 5.6 Hz, H-41,41'), 6.82 (1 H, d, J = 7.6 Hz, H-42) | δ 14.6 (C-27), 15.3 (C-27'), 16.1 (C-26,26'), 16.4 (C-25,25'), 19.6 (C-30,30'), 19.7 (C-6,6'), 21.1 (C-24), 21.1 (C-24'), 21.2 (C-33'), 21.5 (C-33), 22.7 (C-11,11'), 25.7 (C-12), 25.8 (C-12'), 26.7 (C-23), 26.8 (C-23'), 28.4 (C-40), 29.4 (C-15), 29.5 (C-15'), 30.1 (C-21',30'), 31.0 (C-21,30), 32.2 (C-34'), 32.5 (C-34), 33.7 (C-7), 33.8 (C-7'), 34.0 (C-16), 34.1 (C-16'), 34.2 (C-2), 34.3 (C-2'), 36.6 (C-10'), 37.0 (C-10), 37.0 (C-13'), 37.8 (C-13), 38.5 (C-22,22'), 38.7 (C-1,1'), 39.7 (C-8), 39.9 (C-8'), 40.6 (C-31), 40.8 (C-31'), 42.6 (C-14,14'), 46.7 (C-19), 46.9 (C-19'), 47.4 (C-4), 47.4 (C-4'), 50.1 (C-9), 50.2 (C-9'), 50.6 (C-18,18'), 52.4 (C-37), 54.2 (C-35,35'), 55.0 (C-5), 55.1 (C-5'), 55.6 (C-17,17'), 80.0 (C-39), 109.4 (C-29,29'), 151.1 (C-20,20'), 155.7 (C-38), 171.9 (C-36'), 172.9 (C-36), 176.2 (C-28,28'), 218.2 (C-3), 218.4 (C-3') |
| 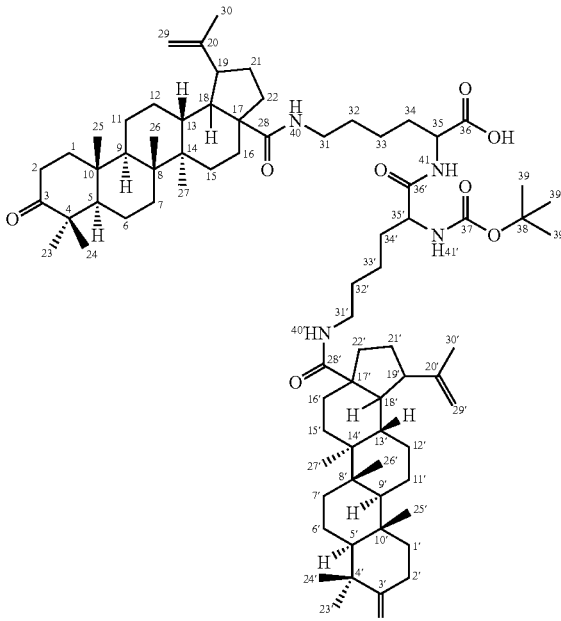<br>Dimer | δ 0.88, 0.91, 0.95, 0.98, 1.01, 1.02, 1.05, 1.06 (30 H, all s, H-23-27,23'-27'), 1.2-1.1.53 (38 H, m, H-1,1',5-7,5'-7',9,9',11,11',12,12',15,15',16,16',18,18',21,21',22,22',33,33'), 1.41 (9 H, brs, H-39), 1.66 (6 H, s, H-30,30'), 1.70-1.75 (8 H, m, H-1,1',16,16',21,21',22,22'), 1.90-1.98 (8 H, m, H-32,32',34,34'), 2.39-2.55 (6 H, m, H-2,2',13,13'), 3.10-3.43 (6 H, m, H-19,19',31,31'), 4.13 (1 H, m, H-35'), 4.31 (1 H, m, H-35), 4.57 (2 H, s, H-29,29'), 4.71 (2 H, s, H-29,29'), 5.18 (1 H, d, J = 7 Hz, H-41'), 5.85 (2 H, t, J = 5.6 Hz, H-40,40'), 6.82 (1 H, d, J = 7.6 Hz, H-41) | δ 14.7 (C-27), 15.4 (C-27'), 16.1 (C-26,26'), 16.5 (C-25,25'), 19.6 (C-30,30'), 19.8 (C-6,6'), 21.1 (C-24), 21.6 (C-24'), 21.5 (C-33'), 21.6 (C-33), 22.9 (C-11,11'), 25.8 (C-12,12'), 26.8 (C-23), 26.9 (C-23'), 28.6 (C-39), 28.9 (C-15), 29.5 (C-15'), 31.1 (C-21,21',30,30'), 32.4 (C-34,34'), 33.6 (C-7), 33.8 (C-7'), 34.0 (C-16), 34.1 (C-16'), 34.3 (C-2,2'), 36.0 (C-10'), 37.0 (C-10), 37.1 (C-13'), 37.7 (C-13), 38.6 (C-22,22'), 39.1 (C-1,1'), 39.8 (C-8), 39.9 (C-8'), 40.6 (C-31), 40.8 (C-31'), 42.6 (C-14,14'), 46.7 (C-19), 47.1 (C-19'), 47.4 (C-4), 47.4 (C-4'), 50.1 (C-9), 50.2 (C-9'), 50.5 (C-18,18'), 54.9 (C-35,35'), 55.0 (C-5), 55.1 (C-5'), 55.6 (C-17,17'), 79.7 (C-38), 109.5 (C-29,29'), 151.2 (C-20,20'), 155.9 (C-37), 176.4 (C-28,28',36,36'), 218.1 (C-3), 218.4 (C-3') |

Betulonic acid and its derivatives were subsequently subjected to spectroscopic analysis in order to resolve their molecular structure. The Electrospray mass spectrometric analysis confirmed their pentacyclic styrene nature of these compounds. The samples were mass analyzed on a Micromass Quattro II triple quadrupole instrument with electrospray (ES) ionization in the positive mode. Samples were introduced by continuous infusion at a rate of 5 µL/min as a nominal 200 µM concentration solution in a 75.25.2 (v/v) acetonitrile-water-acetic acid. When necessary, product ion spectra were obtained by maintaining argon gas in the collision chamber of the instrument at a pressure of 4×10$^{-3}$ mBar.

Figure 2A:
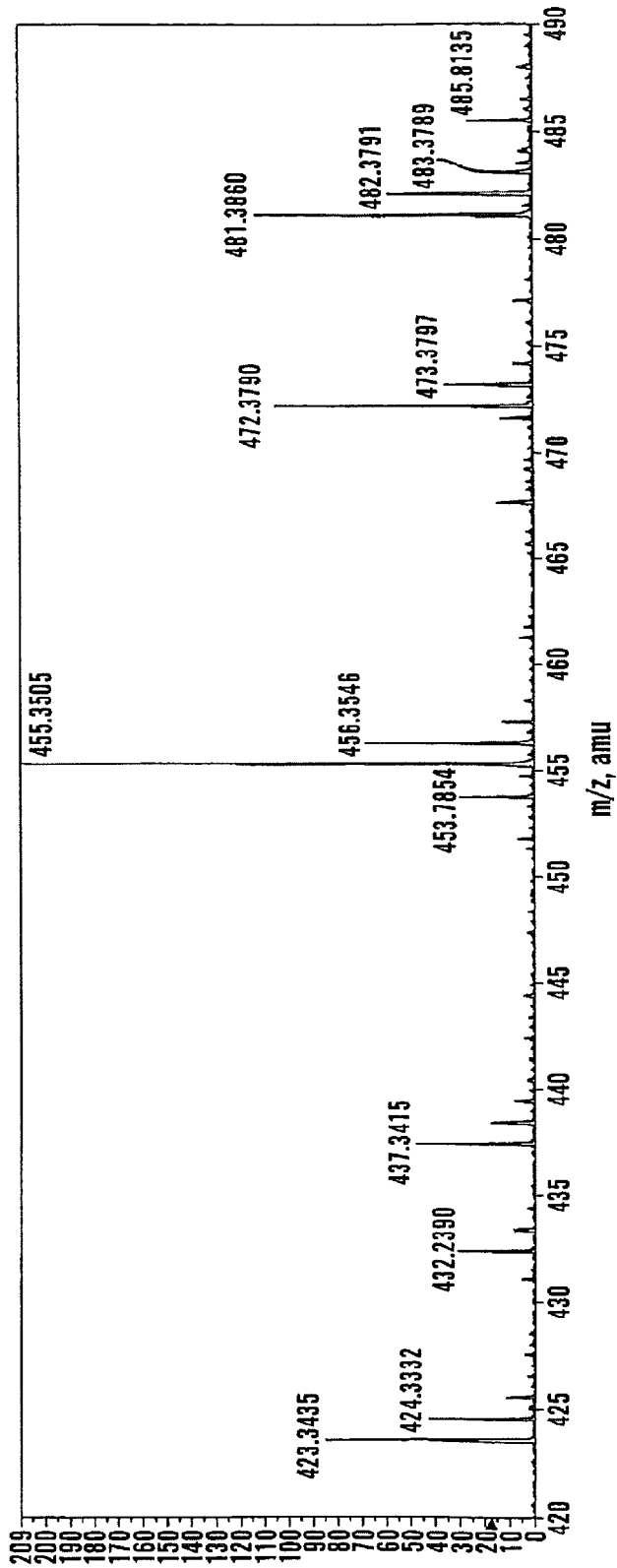
FIG. 2A is a chromatogram that included parts of MS spectra of betulonic acid after internal calibration, and included calibrant signals: m/z 365.3016, 423.3434, 481.3853, 539.4272, and 597.4690 are the calculated masses for poly(propylene glycol) bis(2-aminopropyl ether). In the spectra, [M+H]⁺ and [M+NH₄]⁺ ions (m/z 455 and 472 for betulonic acid) are found, and losses also seen in the MS spectra, deriving from in-source fragmentation (m/z 437 for betulonic acid).
Figure 2B:
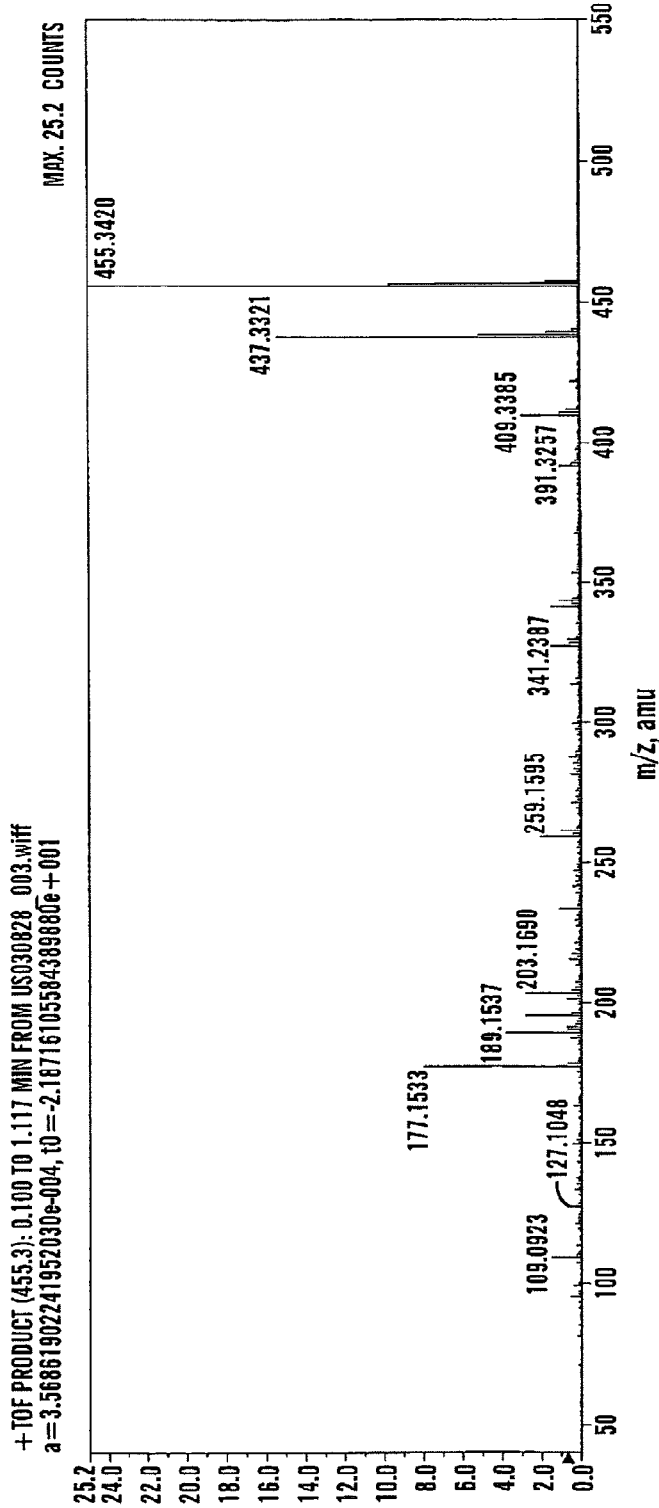
FIG. 2B shows the MS spectra of m/z 544, 471, and 455 for betulonic acid.

FIG. 2A included parts of MS spectra of betulonic acid after internal calibration, and included calibrant signals: m/z 365.3016, 423.3434, 481.3853, 539.4272, and 597.4690 are the calculated masses for poly(propylene glycol) bis(2-aminopropyl ether). In the spectra, [M+H]$^+$ and [M+NH$_4$]$^+$ ions (m/z 455 and 472 for betulonic acid) are found, and losses also seen in the MSMS spectra, deriving from in-source fragmentation (m/z 437 for betulonic acid). FIG. 2B shows the MSMS spectra of m/z 544, 471, and 455 for betulonic acid.

Figure 3A:
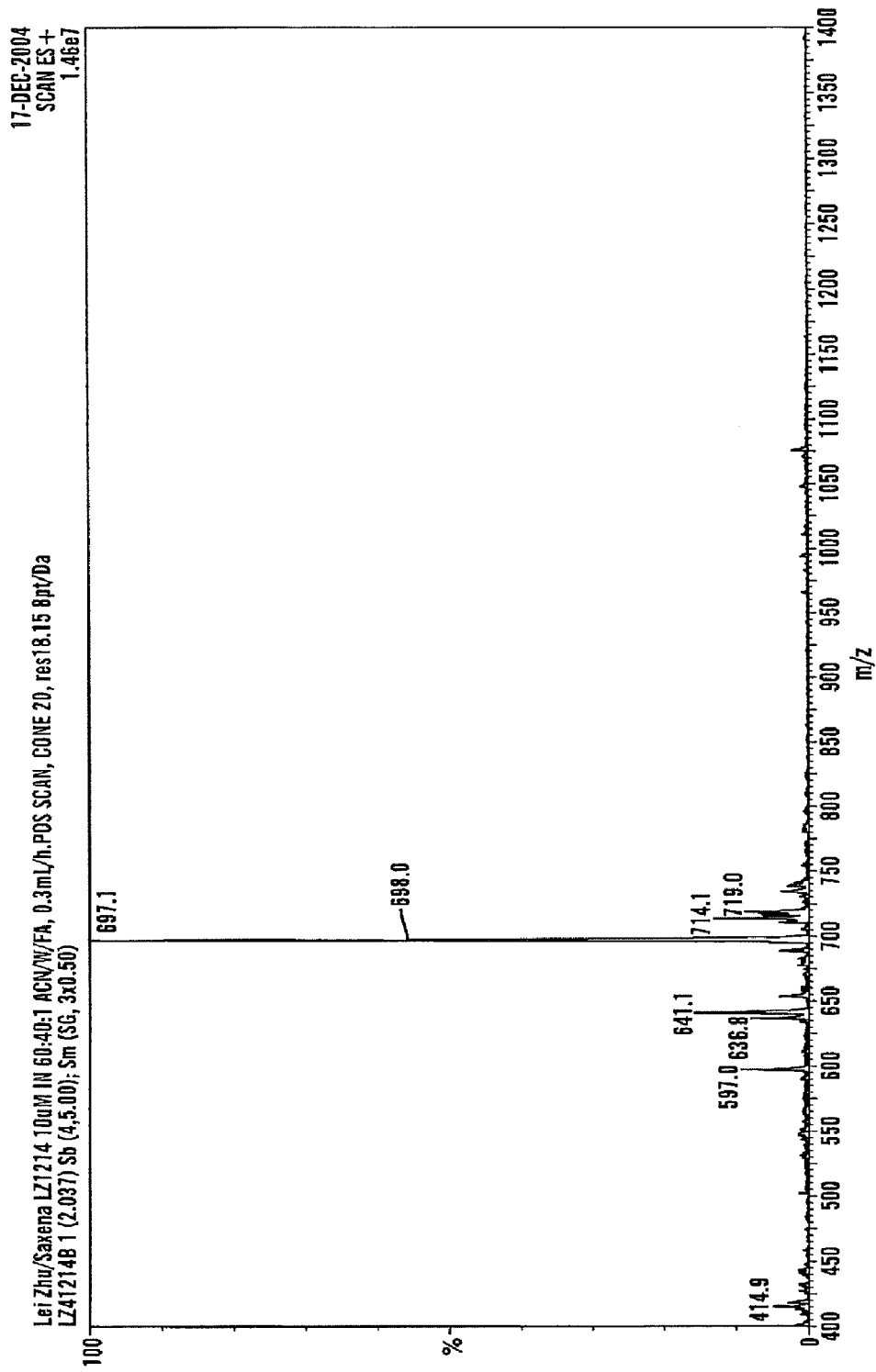
FIG. 3A-C are MS spectra of monomer ester showing that it is essentially a single compound, appearing as the m/z 697 singly protonated ion (FIG. 3A). From a higher resolution, more slowly recorded ESI-MS scan (FIG. 3B), the monoisotopic molecular mass of the neutral compound is computed as 696.5±0.2 Da. The singly protonated positive ion of this compound is rather labile. As shown in the product ion spectrum of FIG. 3C, the collision induced decomposition (CID) of the m/z 697 ion has two efficient pathways, one involving the loss of a 56 Da neutral, the other the loss of a 100 Da neutral. The fragmentation requires relatively low collision energy (10 volts). As a consequence, the m/z 641 and 597 ions also show up in the ordinary mass spectrum of FIG. 3A under source conditions where average stability molecules would not fragment.
Figure 3B:
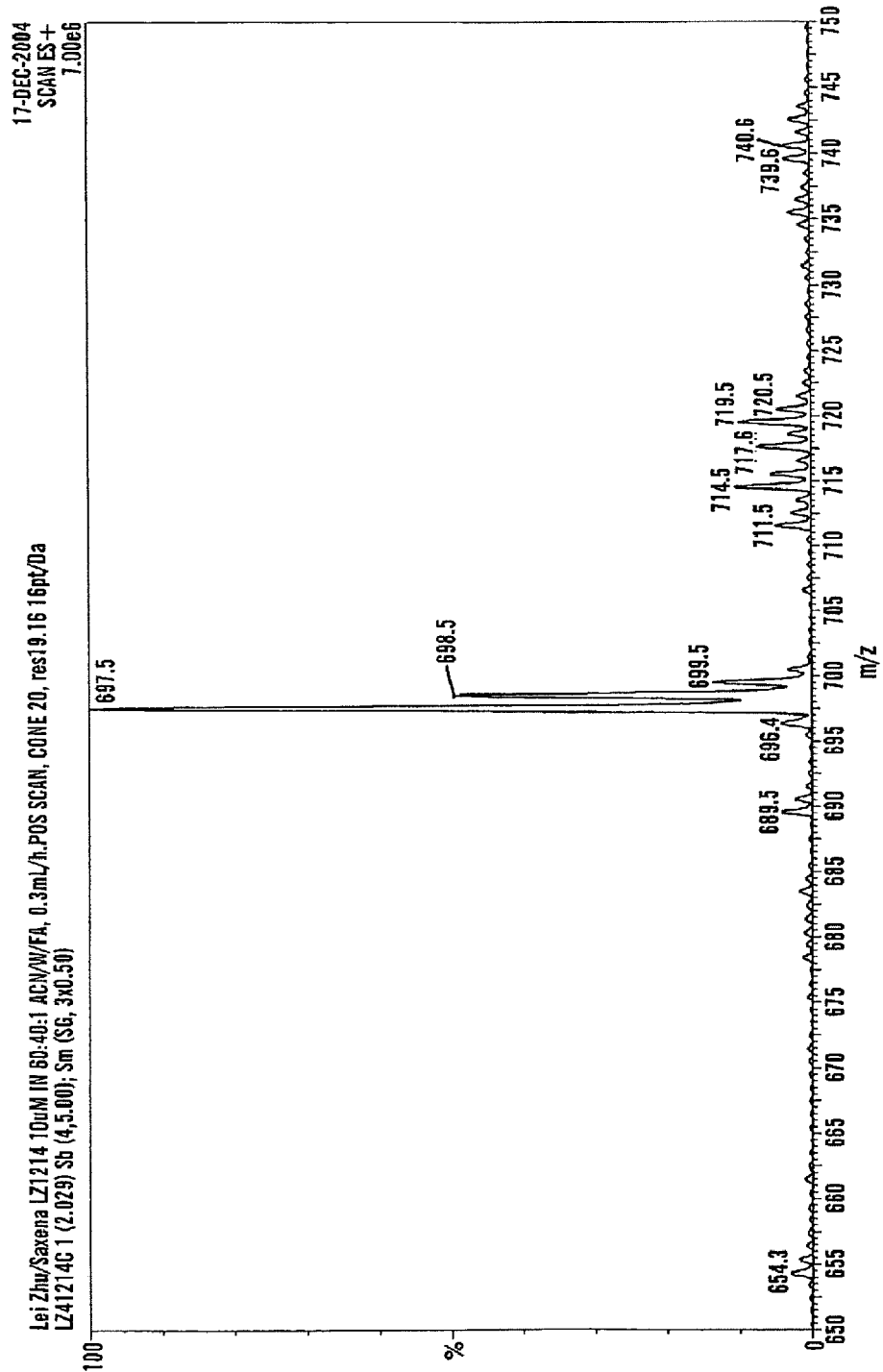
Figure 3C:
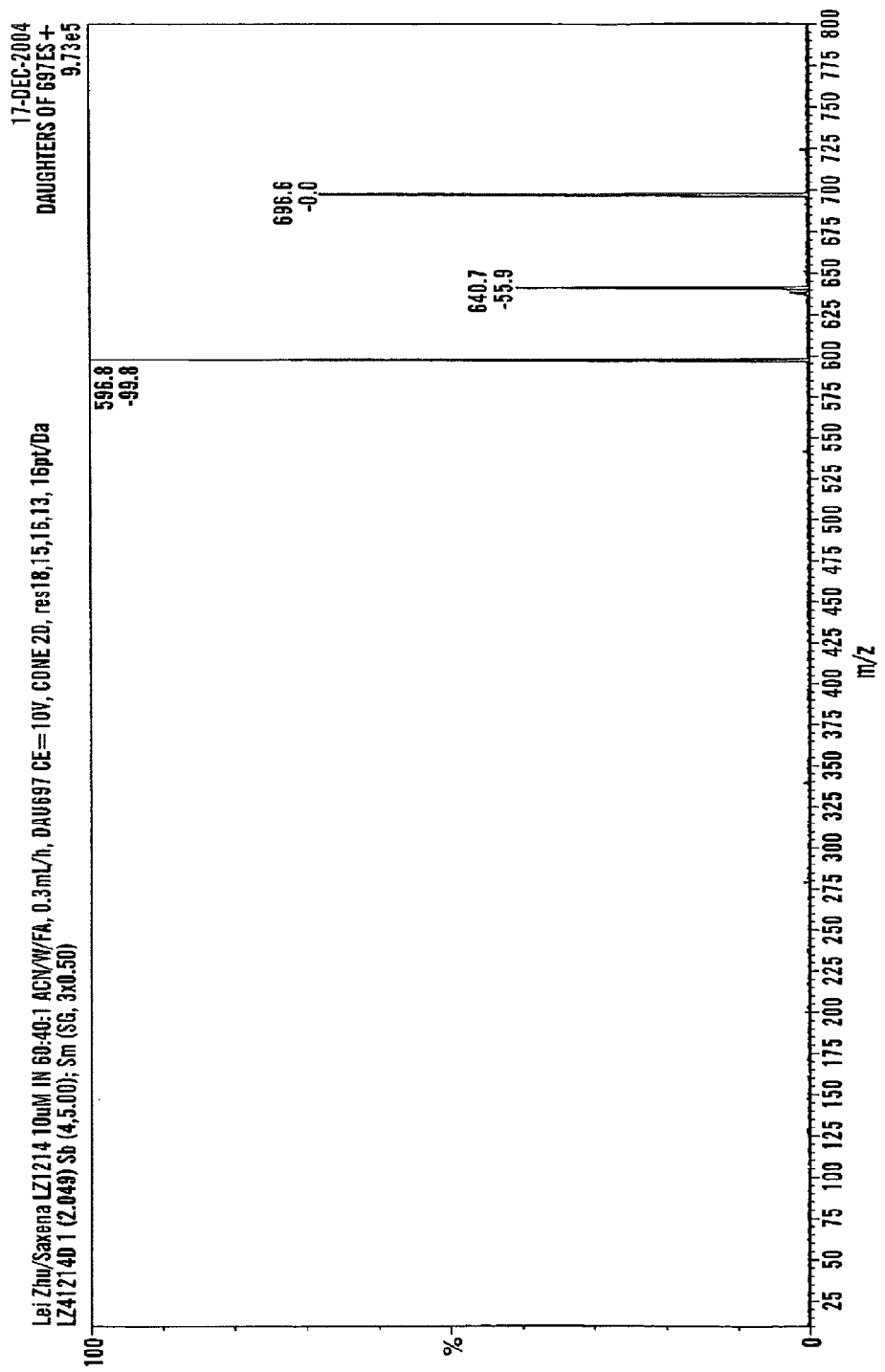

The MS spectra of monomer ester (FIGS. 3A-C) show that it is essentially a single compound, appearing as the m/z 697 singly protonated ion (FIG. 3A). From a higher resolution, more slowly recorded ESI-MS scan (FIG. 3B) the monoisotopic molecular mass of the neutral compound is computed as 696.5±0.2 Da. The singly protonated positive ion of this compound is rather labile. As shown in the product ion spectrum (FIG. 3C), the collision induced decomposition (CID) of the m/z 697 ion has two efficient pathways, one involving the loss of a 56 Da neutral, the other the loss of a 100 Da neutral. The fragmentation requires relatively low collision energy, 10 volts. As a consequence, the m/z 641 and 597 ions also show up in the ordinary mass spectrum of FIG. 3A under source conditions where average stability molecules would not fragment.

Figure 4A:
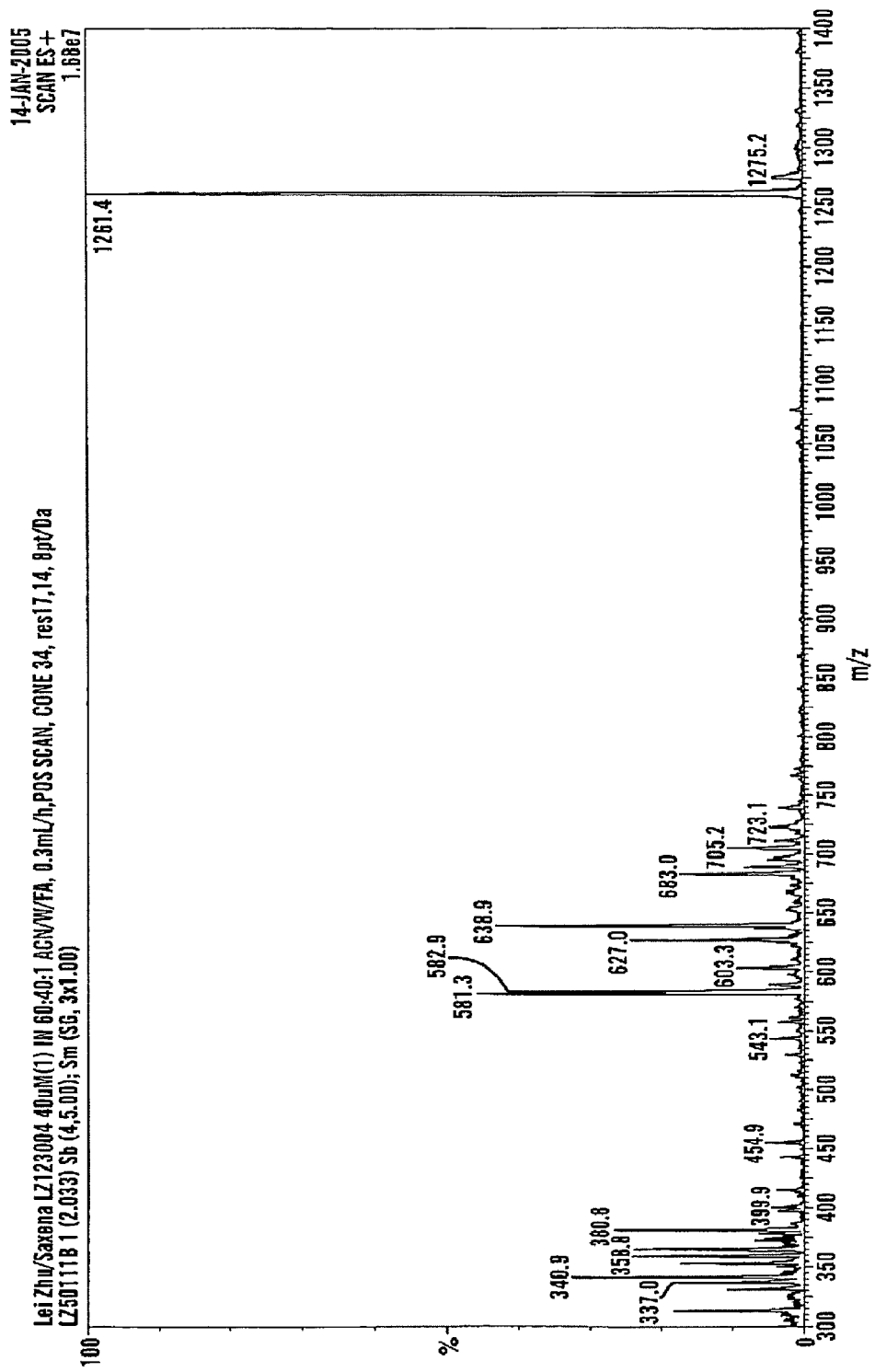
FIGS. 4A-B show the MS spectra of dimer ester.
Figure 4B:
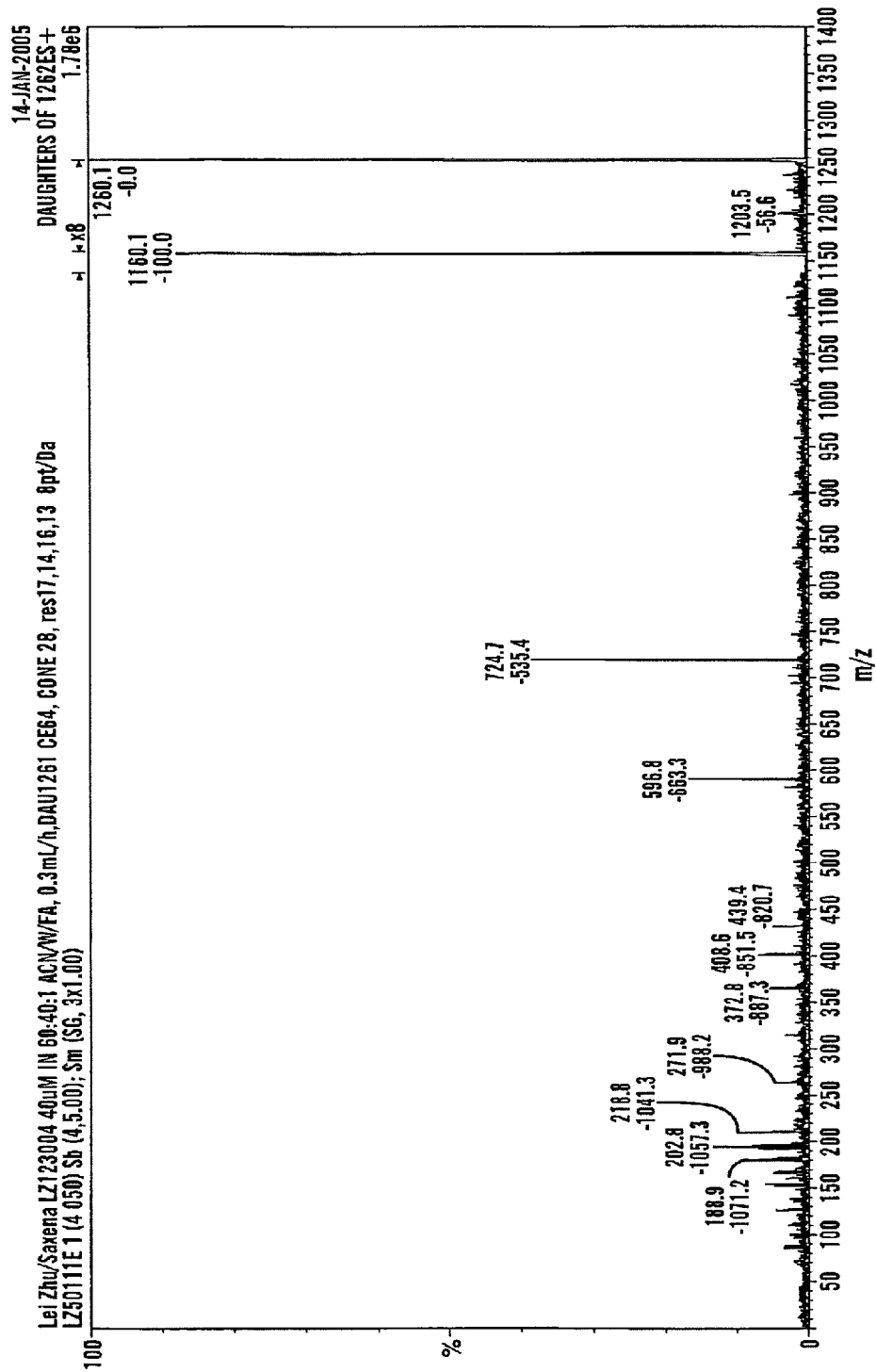

The MS spectra of dimer ester is shown in FIGS. 4A-B. As shown in FIG. 4A, the most intense peak in the ESI mass spectrum is the singly protonated ion at m/z 1261. The low level impurities with ion at m/z 581, 627, 639, and 683 are present. Since the sensitivity for the structure is low, 40 µM concentration solution was used to observe a strong m/z 1261 peak. As shown in FIG. 4B, the predominant fragmentation process, as it was in monomer ester, is the loss of a 100 Da neutral, presumably in the form of isobutylene+CO$_2$. Among the additional, very weak, product ions those at m/z 1204 and 734 are significant, because they can be interpreted as a loss of C$_4$H$_8$ and a loss of a betulonic acid residue, respectively.

Example 5

Synthesis of Monolysinated Betulonic Acid

N$_\alpha$-butyloxycarbonyl-N$_\epsilon$-benzyloxycarbonyl-Lysine (Boc-Lys (Cbz)-OH), having the formula (4)

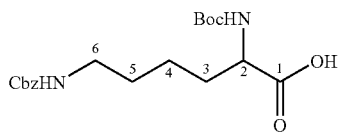

4 was obtained from Sigma-Aldrich. Both amines on C-2 and C-6 were protected by butyloxycarbonyl (Boc) and carbobenzoxy (Cbz), respectively.

N$_\alpha$-butyloxycarbonyl-N$_\epsilon$-benzyloxycarbonyl-Lysine methylester (Boc-Lys (Cbz)-OMe) was prepared as described in Kobayashi et al., *J. Org. Chem.* 66:6626-6633 (2001), which is hereby incorporated by reference in its entirety). To a 7.5 mL of trimethylsilyldiazomethane containing 1.0 g of Boc-Lys(Cbz)-OH (4) was added 5 mL anhydrous methanol while stirring at room temperature. The mixture was stirred at room temperature for 20 min, and concentrated in vacuo. The residue was subjected to a silica gel column chromatography to yield 1.0 g of Boc-Lys(Cbz)-OMe of formula (5):

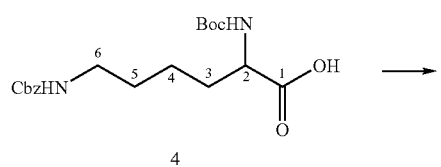

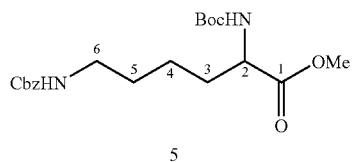

5

1.0 g of Boc-Lys(Cbz)-OMe (5) was dissolved in 40 mL MeOH:Ethyl acetate. 100 mg of Palladium on active carbon (Pd/C) was added to the solution. The solution was stirred under hydrogen for 2 hrs. The organic solution was filtered through Celite and washed with 10 mL MeOH. The filtrate was evaporated under reduced pressure to yield Boc-Lys-OMe of formula (6)

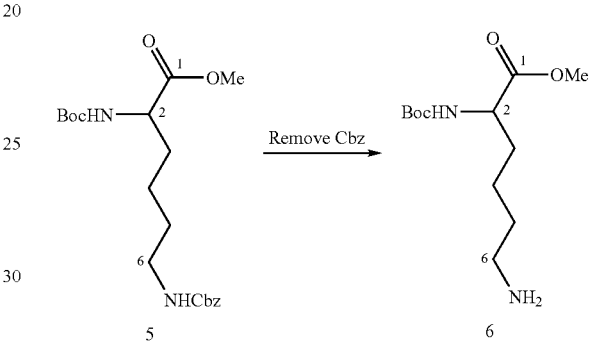

as a white solid, which was used directly for conjugation with betulonic acid (3).

Conjugation of betulonic acid to Boc-Lys-OMe monomer was carried out as described in Zhao et al., *J. Org. Chem.* 69:270-279 (2004), which is hereby incorporated by reference in its entirety. To a 30 mL solution of Boc-Lys-OMe (6) in anhydrous tetrahydrofuran ("THF") in an ice bath while stirring, 940 mg of betulonic acid (3), 350 mg of 1-Hydroxybenzotriazole Hydrate ("HOBt"), 530 mg of 1,3-dicyclohexylcarbodiimide ("DCC"), and 435 µL triethylamine were added. The mixture was stirred at 0° C. for 2 hrs and then at room temperature for 48 hrs. The resulting suspension was filtered through filter paper and the filtrate was concentrated in vacuo. The residue was subjected to silica gel column chromatography to obtain 1.3 g of monomer of formula (7)

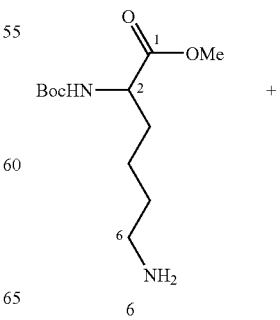

6

-continued

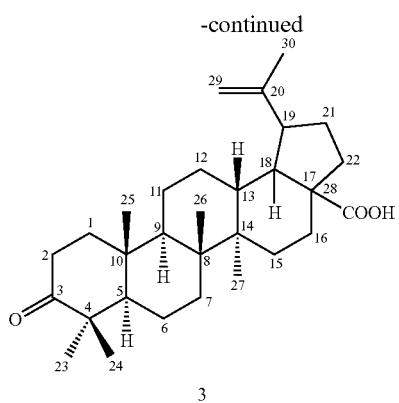

3

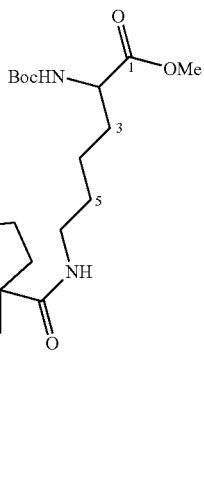

7 as a white solid.

Example 6

Conjugation of Two Monolysinated Betulonic Acid 150 mg of monomer (7) and 10.9 mg lithium hydroxide monohydrate (LiOH.H₂O) was dissolved in 3 mL THF and 100 µL H₂O. The resulting solution was stirred at room temperature until (7) was completely used up as monitored by thin layer chromatography ("TLC"). The solution was concentrated in vacuo. The resulting solid was subjected to silica gel column chromatography to obtain 142.6 mg of Monomer-Boc of formula (7a)

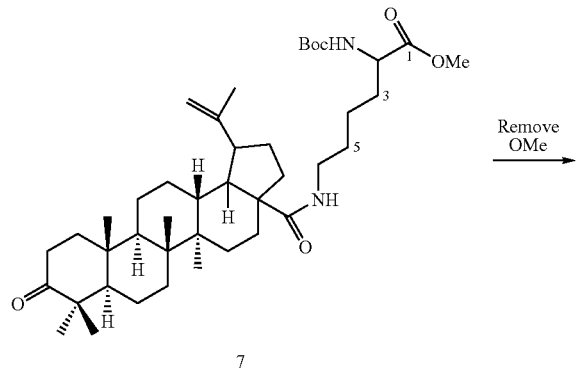

-continued

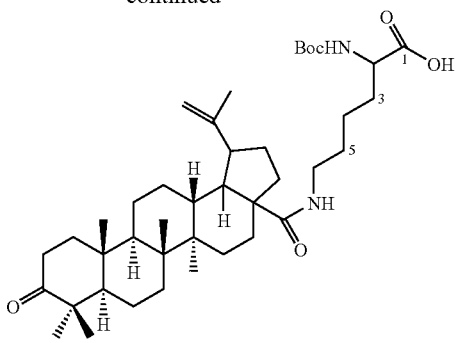

7a as white solid.

Monomer-OMe (N$_\epsilon$-betuloniccarbonyl-Lysine Methyl Ester) was prepared as described in Chun et al., *J. Org. Chem.* 69:7344-7347 (2004), which is hereby incorporated by reference in its entirety. Specifically, 20 mg of monomer (7) was dissolved in anhydrous 1 mL CH₂Cl₂ at 0° C. A solution of 11 µL trifluoroacetic acid (TFA) in 11 µL CH₂Cl₂ was added drop wise. The reaction mixture was stirred at room temperature for 12 h. The solvent was evaporated under vacuum. The residue was triturated with petroleum ether. The organic solvent was evaporated under vacuum to obtain crude Monomer-OMe of formula (7b)

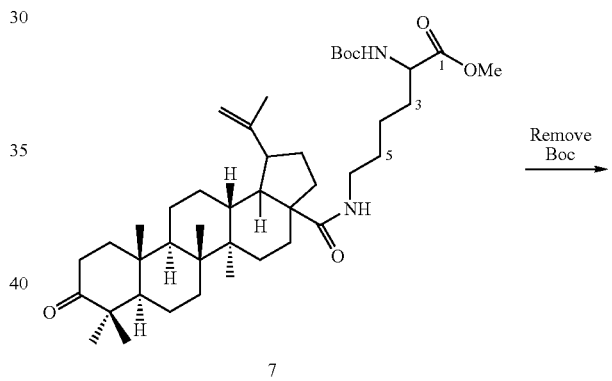

7

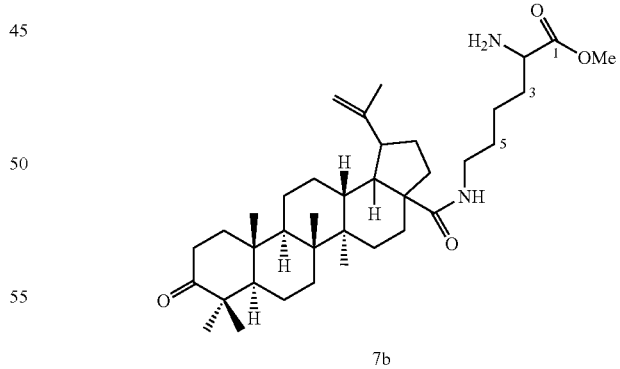

7b

To a solution of 19 mg of Monomer-Boc (7a) and 4.1 mg of HOBt in 0.5 mL dried dimethylformamide (DMF), 6 mg of DCC was added at 0° C. After the mixture was stirred for 30 min, a solution of 11.6 µL triethylamine and (7b) in 0.5 mL dried DMF was added drop wise. Stirring was continued at 0° C. for 4 h and then at room temperature for 3 days. The solvent was evaporated under reduced pressure and the resulting residue was silica gel column chromatographed to obtain 28.3 mg of dimer of formula (8)

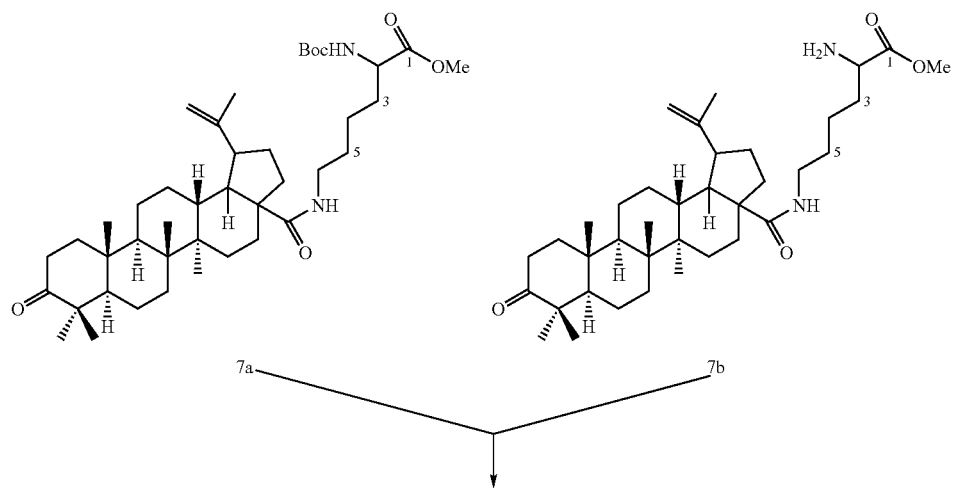

7a  7b

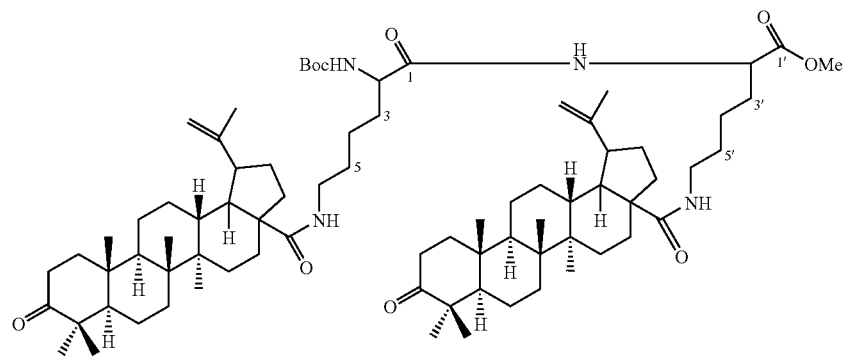

8

Example 7

Conjugation of Two Dimers 150 mg of dimer (8) and 10.9 mg of LiOH.H$_2$O were dissolved in 3 mL THF and 100 μL H$_2$O. The resulting solution was stirred at room temperature until (8) was completely used up as monitored by TLC. The solution was concentrated in vacuo. The resulting solid was subjected to silica gel column chromatography to obtain 142.6 mg of Dimer-Boc of formula (8a)

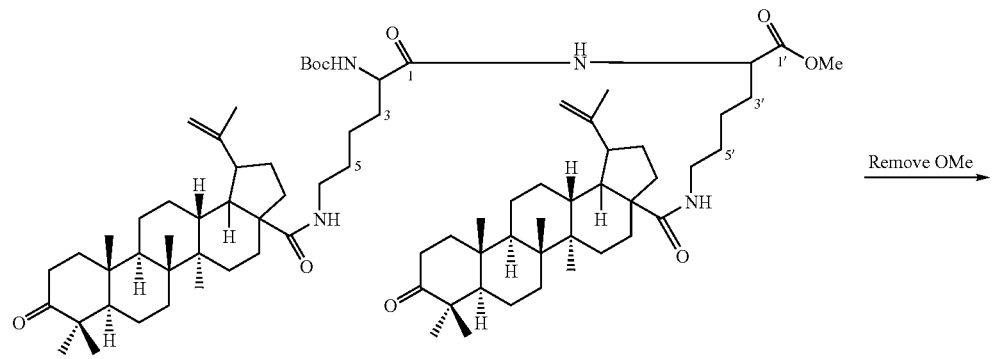

Remove OMe

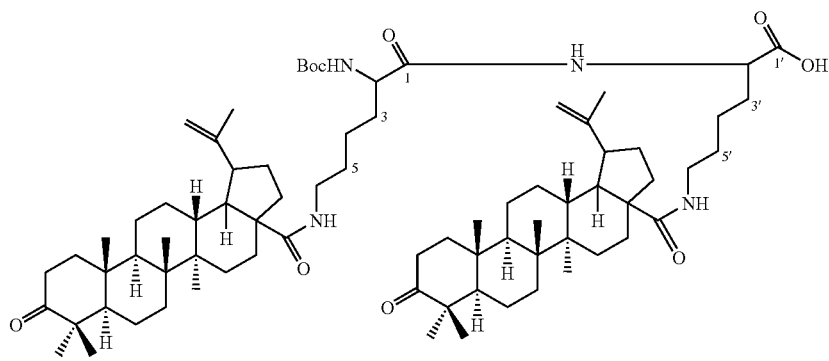

8a 100 mg of dimer (8) was dissolved in anhydrous 1 mL CH$_2$Cl$_2$ at 0° C. A solution of 31 μL TFA in 31 μL CH$_2$Cl$_2$ was added drop wise. The reaction mixture was stirred at room temperature for 12 hrs. The solvent was evaporated under vacuum. The residue was triturated with petroleum ether. The organic solvent was evaporated under vacuum to obtain crude Dimer-OMe of formula (8b)

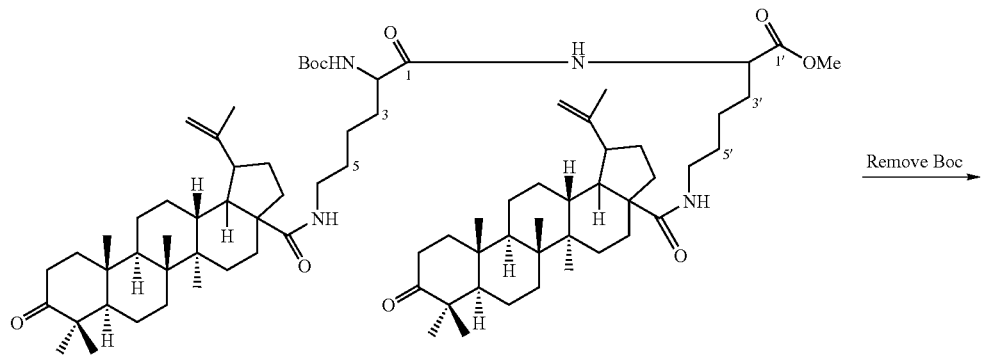

8

Remove Boc →

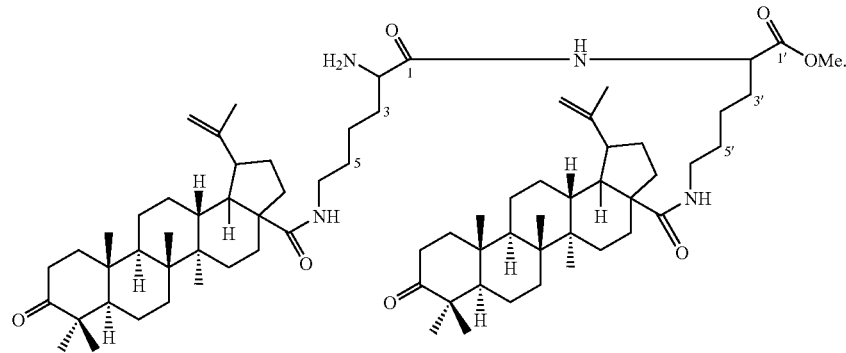

8b

To a solution of 100 mg of Dimer-Boc (8a) and 12 mg HOBt in 2 mL dried DMF, 18 mg of DCC was added at 0° C. After the mixture was stirred for 30 min, a solution of 22 μL triethylamine and (8b) in 1.7 mL dried DMF was added drop wise. Stirring was continued at 0° C. for 4 hrs and then at room temperature for 5 d. The solvent was evaporated under reduced pressure and the resulting residue was silica gel column chromatographed to obtain 20.8 mg of tetramer of formula (9)

8.3 mg of tetramer (9) and 1 mg of LiOH.H$_2$O was dissolved in 300 μL MeOH and 50 μL H$_2$O. The resulting solution was stirred at room temperature until (9) was completely used up as monitored by TLC. The solution was concentrated in vacuo. The resulting solid was subjected to silica gel column chromatography to obtain 3 mg of Tetramer-Boc (10)

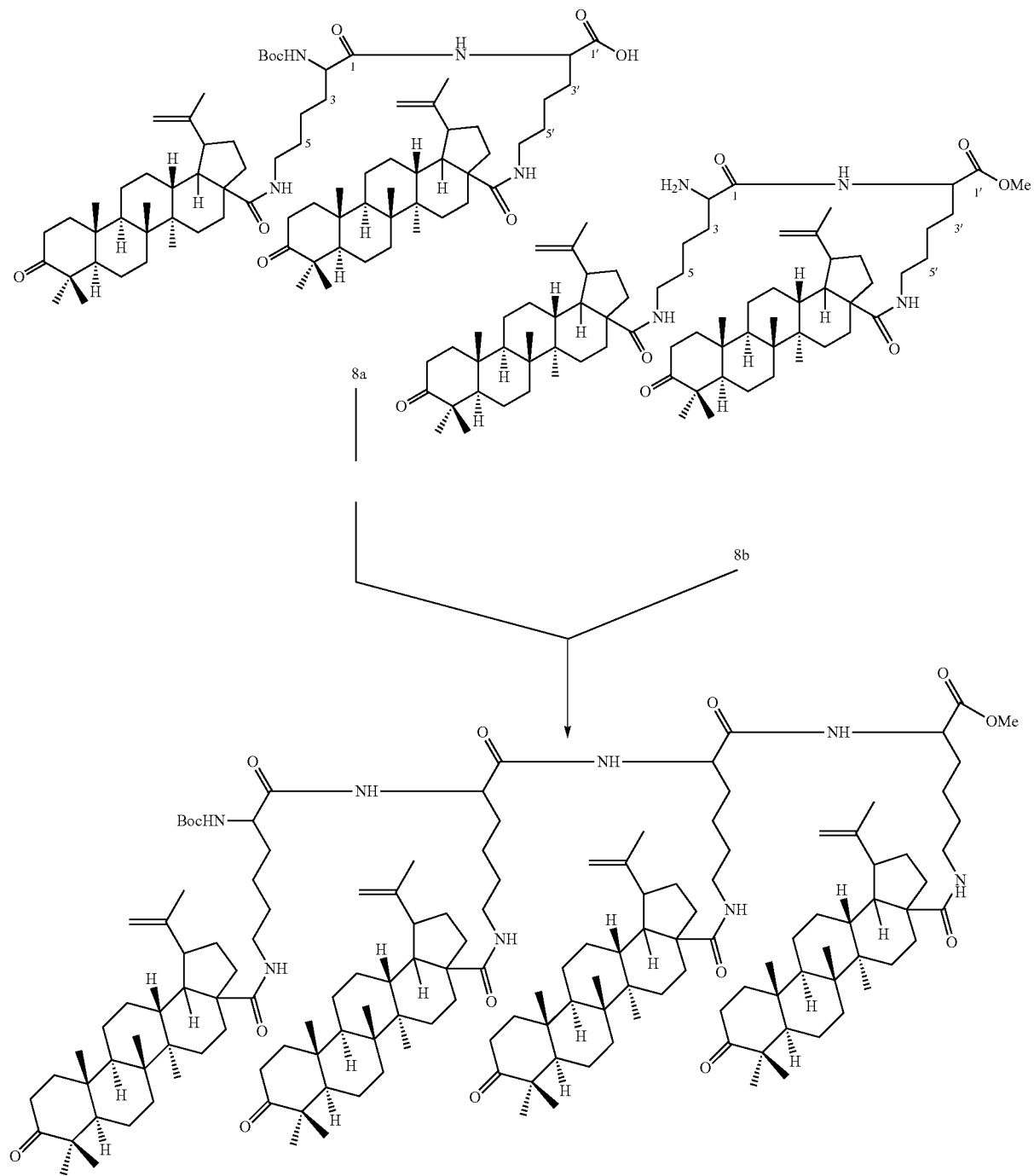

as a white solid.

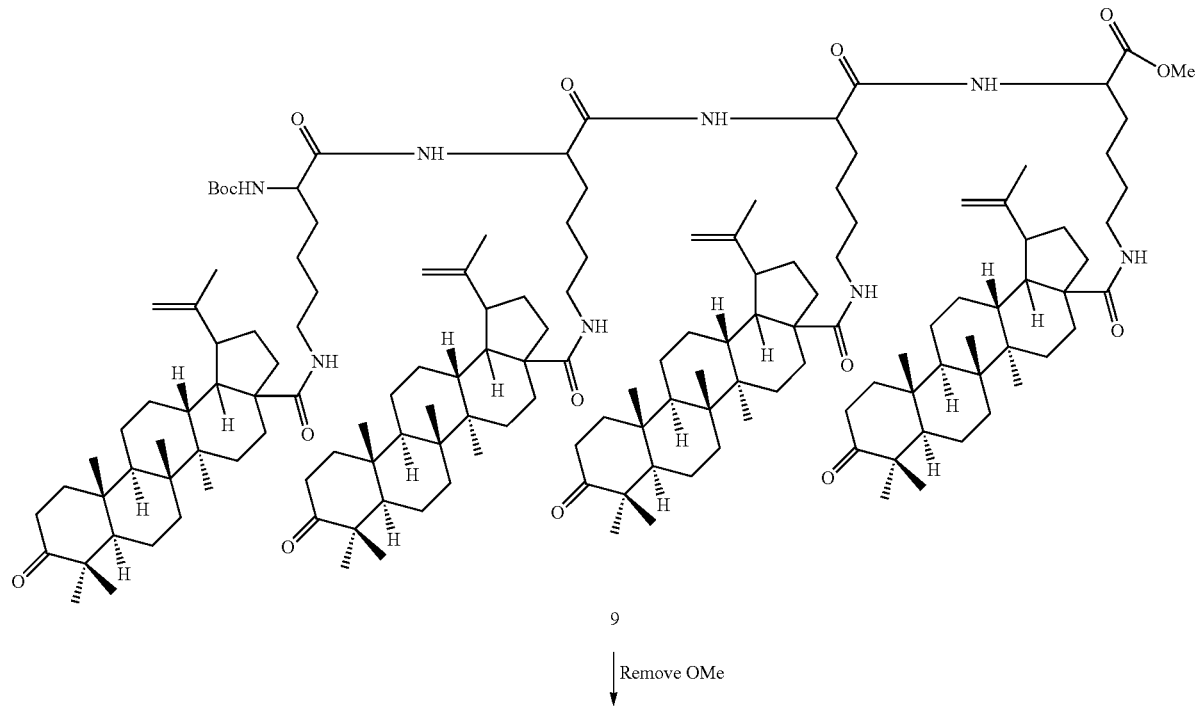
9
↓ Remove OMe
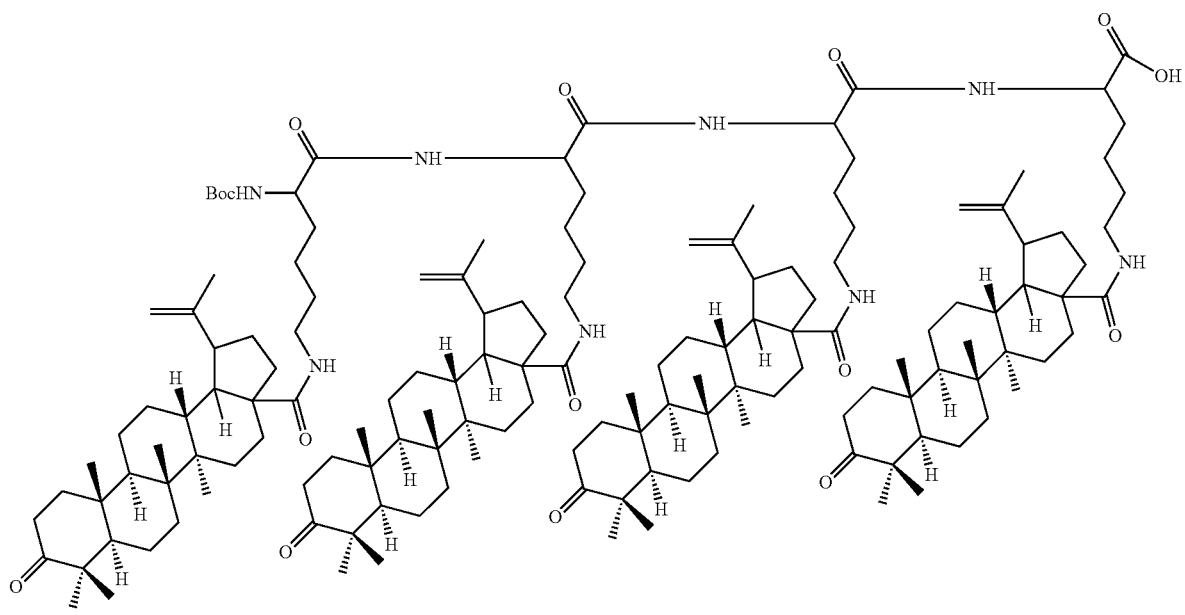
10 as white solid with 3.4 mg of unreacted tetramer (9). Tetramer (9), abbreviated as
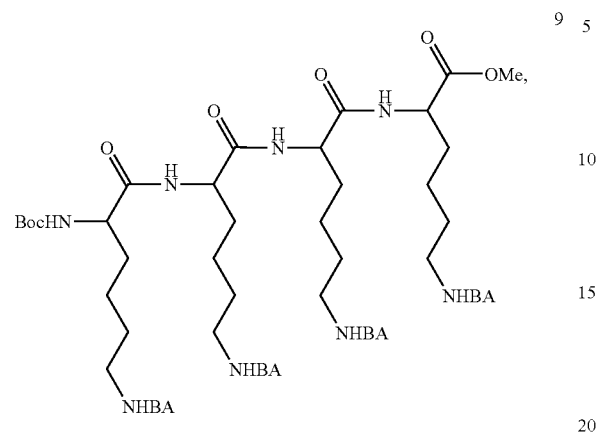
can be used for synthesis of pentamer-BA of formula (15)
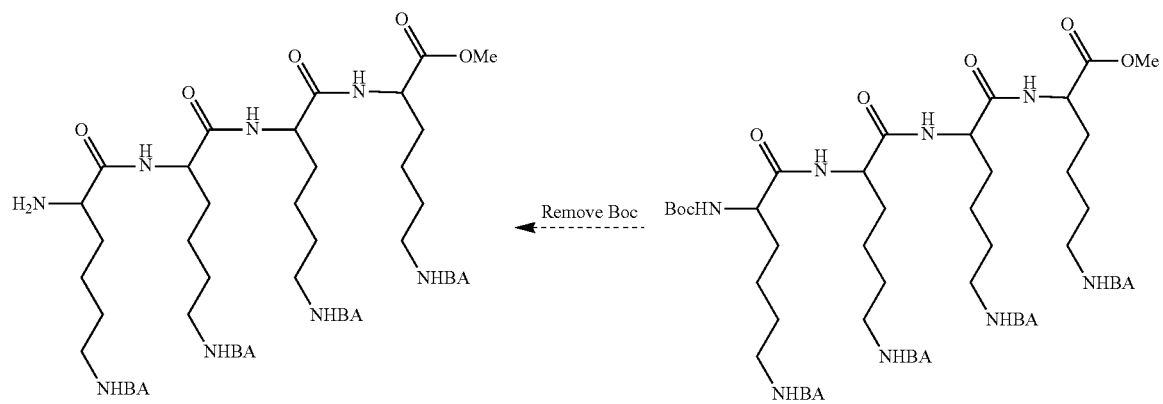
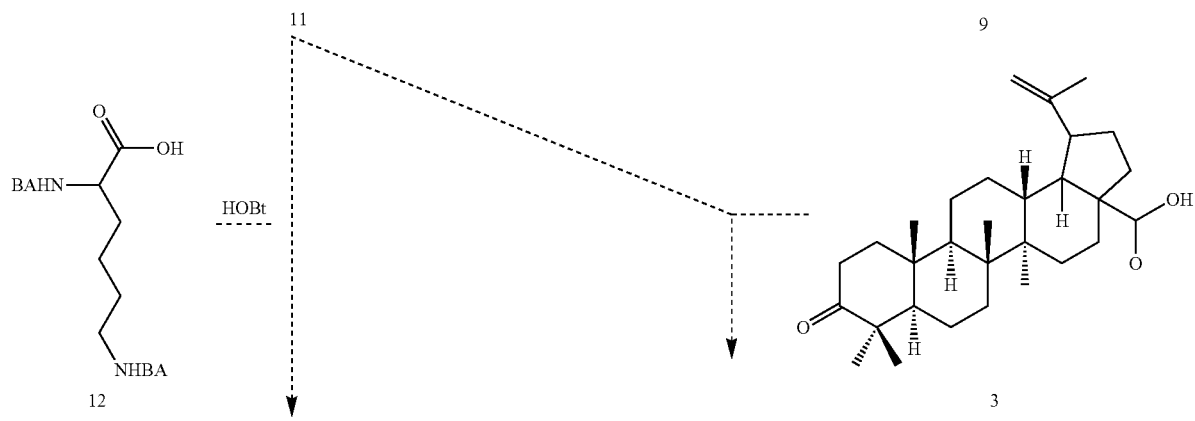

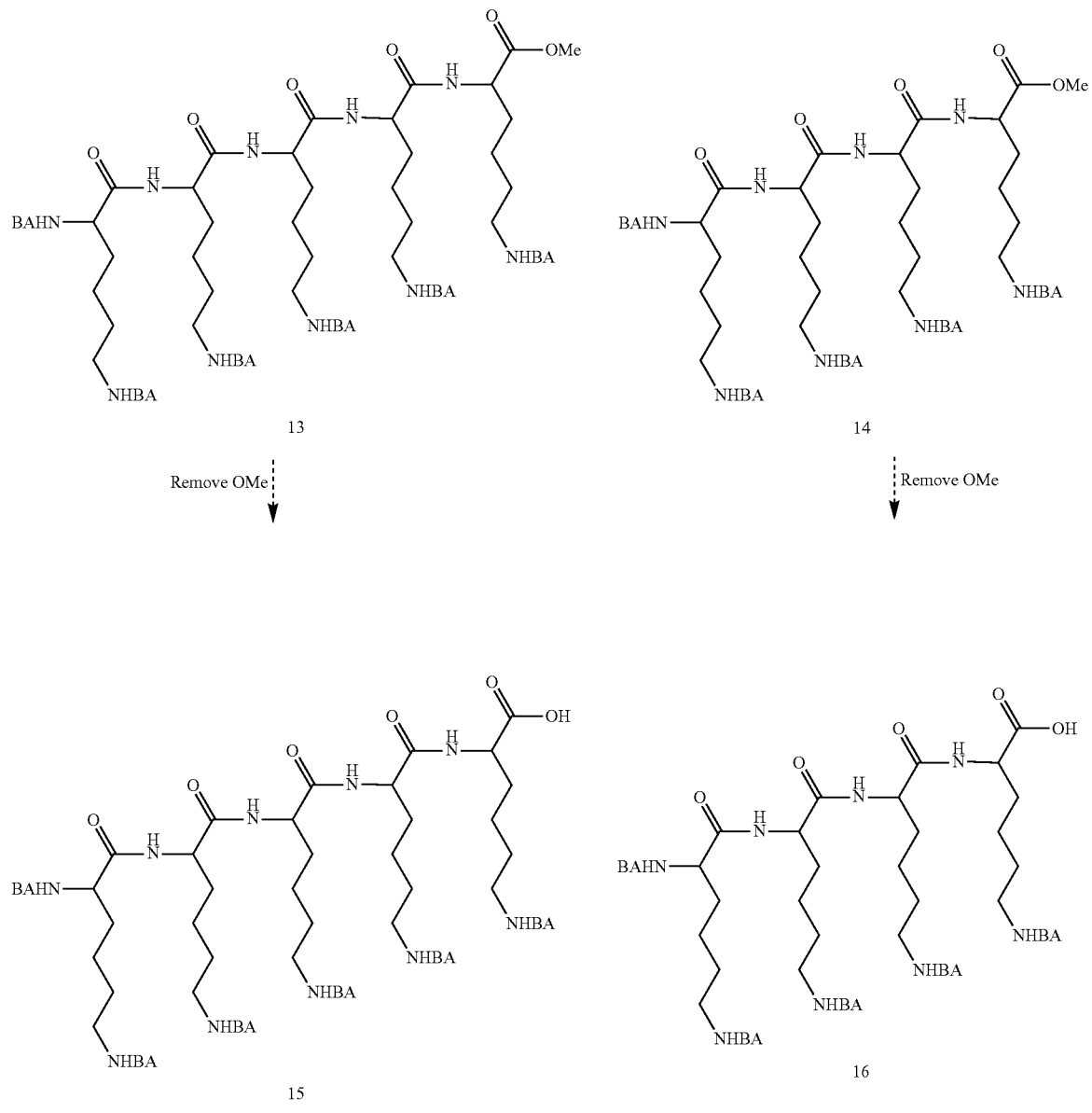

which contains six molecules of betulonic acid (3). In particular, selective deprotection can be carried out on tetramer (9) to remove Boc group and generate tetramer-OMe of formula (11). Conjugation of (11) with monomer derivative of formula (12) could yield pentamer-OMe of formula (13). Hydrolysis on (13) to selective remove methyl ester could form pentamer (5):

In addition, tetramer-OMe (11) could connect to betulonic acid (3) directly instead of the monomer derivative (12). This will yield tetramer-BA of formula (16), which contains five molecules of betulonic acid (3). Conjugation of (11) with betulonic acid (3) yields tetramer-BA-OMe of formula (14). The same hydrolysis on (14) to remove methyl ester generates tetramer-BA of formula (16).

Example 8

Preparation of Pentamer with Six Molecules of Betulonic Acid

A simple and direct way to prepare pentamer is to conjugate pentalysine with betulonic acid. However, pentalysine itself, without any protecting groups, is unstable, because it is easily polymerized and cyclized. The C-1a carboxyl group of pentalysine can be easily coupled with α-amine on C-2e or primary amines on C-6(a-e) of another molecule to form a polymer. This polymer is composed of different numbers of amino acid groups, yielding different lengths of peptide. In addition, the coupling reaction can happen in the same molecule, which connects the amino and carboxy ends of the pentalysine and cyclizes, which is illustrated as follows:

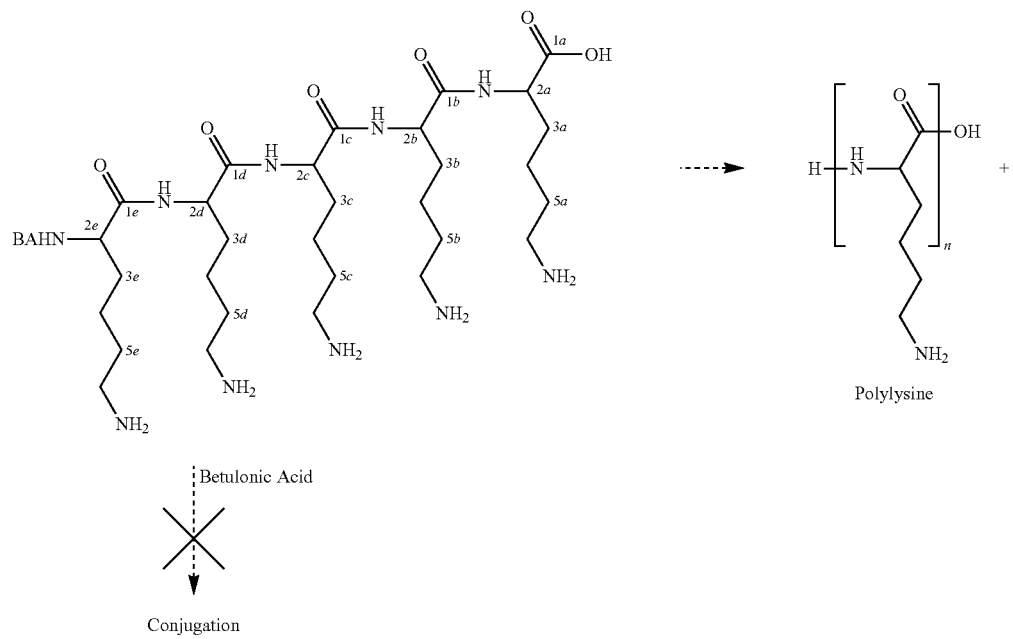
Polylysine
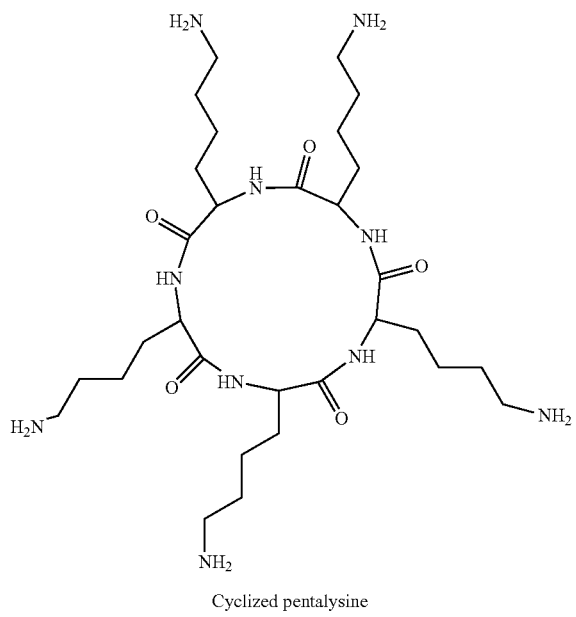
Cyclized pentalysine
A pentalysine derivative is needed to conjugate with betulonic acid. Further, pentalysine methyl ester of formula (17)

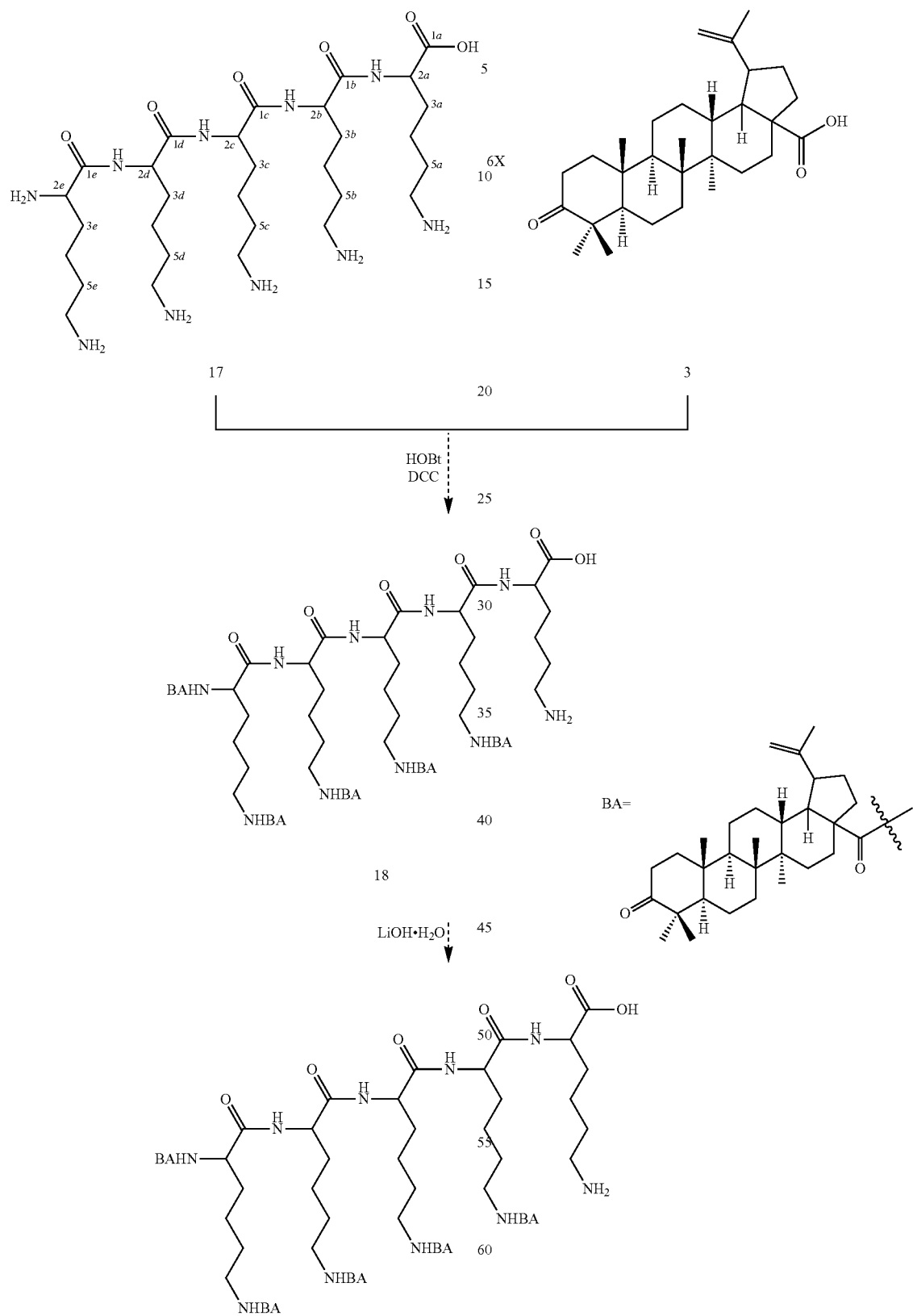

has C-1a carboxyl protected by ester with all other amines free to conjugate. In particular, pentalysine methyl ester (17) could react with six molecules of betulonic acid (3) and is catalyzed by DCC and HOBt to yield pentamer methyl ester of formula (18). Subjecting the ester to hydrolysis removes the methyl protecting group to generate pentamer of formula (19), which contains six molecules of betulonic acid. Pentamer (19) with six molecules of betulonic acid and free carboxyl can be used for immunoconjugation with an antibody.

Example 9

Immunoconjugates

Immunoconjugates of betulin derivatives were made by conjugation of α-globulin with lysinated betulonic acid. The synthetic structural modification strategy described previously is seen as a prelude to create sites for conjugation to a monoclonal antibody. As an exploratory feasibility study, monomer was conjugated with rabbit γ-globulin via an activated carboxyl group (COOH). Carbodiimide method is presently assessed. This bioconjugation reaction made use of different activated intermediates.

According to the carbodiimide method with 1,3-dicyclohexylcarbodiimide ("DCC"), monomers (13 mg, 0.02 mmol) as described above were dissolved in 0.2 mL of dry DMF with N-hydroxysuccinimide (NHS) (3.3 mg, 0.03 mmol) and a 20% molar excess of DCC. After 18 h of stirring at 4° C., the resulting activated ester was added slowly to the protein solution (10 mg of γ-globulin in 2 mL of 0.1 M carbonate buffer of pH 9.6) with vigorous stirring. The reaction mixture was stirred gently at 4° C. for 24 h to complete the conjugation and then dialyzed (Spectra/Por 7, Spectrum Laboratories) exhaustively against 250 mL of 0.01 M sodium phosphate buffer pH 7.2 containing 0.015 M NaCl (PBS) for 72 h with two exchanges of this buffer to give the monomer-antibody conjugate. The mixture was centrifuged (10,500 rpm) for 6 minutes and then supernatant was stored for cell cultures.

According to the carbodiimide method with 1-ethyl-3[3-dimethylaminopropyl carbodiimide ("EDC"), EDC solution (0.4 mg of EDC in 50 µL of DMF) and NHS solution (0.4 mg of NHS in 25 µL DMF) were freshly prepared and added to a monomer solution (0.2 µg of monomer in 500 µL of DMF). The reaction was kept at room temperature for 30 min and then kept at 4° C. overnight. The mixture was added slowly to 2 mg γ-globulin which was dialyzed against 250 mL of 0.1 M pH 9.4 carbonate buffer 4° C. 18 h. The reaction was carried out at 4° C. for overnight. The reaction mixture was dialyzed against 200 mL of 0.01 M phosphate buffer pH 7.2 containing 0.015 NaCl (PBS) for 72 h with two exchange of this buffer to give the monomer-antibody conjugate. The mixture was centrifuged (10,500 rpm) for 6 minutes and then precipitate was stored for cell culture.

Example 10

General Experimental Procedures

Chromatography

Flash column chromatography ("FCC") was performed using silica gel grade 9385 of 230-400 mesh (E. Merck). A stepwise solvent polarity gradient was employed. TLC was performed on aluminum sheets precoated with silica gel 60 (HF-254, E. Merck) to a thickness of 0.25 mm.

NMR Spectroscopy

Suitably pure products were taken on a Varian Inova AS 500 spectrometer operating at 500 MHz, equipped with a 5 mm triple resonance three axis gradient probe. Temperature calibrations were carried out using 100% methanol, with calibration values provide by Varian Instruments (Palo Alto, Calif.). Proton frequencies were reference to $CDCl_3$. NMR data processing and Varian Instruments carried spectral integration out using the VNMR software supplied. All NMR spectra were taken at NMR Core Facility Department of Chemistry, Hunter College, The City University of New York.

Mass Spectrometry

Accurate mass analysis obtained at the Biopolymer Mass Spectrometry Core Facility (Cornell University) was taken on a Micromass Quattro II triple quadrupole instrument with electrospray ionization in the positive ion mode. Samples were introduced by continuous infusion at a rate of 5 µL/min as a nominal 200 µM concentration solution in a 75:25:2 (v/v) acetonitrile/water/acetic acid solvent. When necessary, product ion spectra were obtained by maintaining argon gas in the collision chamber of the instrument at a pressure of $4 \times 10^{-3}$ mBar.

Gas Chromatography

To circumvent the problem of assessing the purity of betulin derived compounds, a rapid gas chromatographic method was developed. A 30 mm×25 mm×0.25 µm film thickness fused silica capillary column SAC-5 containing 5% phenyl and 95% dimethylpolysiloxane provides reproducible relative retention times for the betulin derivatives. All chromatographic analysis was performed on a Shimadzu Gas Chromatograph-14A with a typical setting:

| | |
|---|---|
| GC column: | SAC-5 Fused Silica Capillary Column containing 5% phenyl and 95% dimethyl polysiloxane; 30 mm × 25 mm × 0.25 µm file thickness; Conditioned overnight prior to all sample run |
| Flow rate: | 60 mL/min |
| Gas pressure: | Air (50 kPa); $H_2$ (55 kPa); p1 (80 kPa); p2 (150 kPa) |
| Temperature: | 300° C. injector/column/detector |
| Injector: | Split |
| Detector: | FID |
| Vol. of sample: | 8 µL in chloroform. |

Example 11

Standard Solubility Curve of Betulonic Acid

In order to determine the solubility of betulonic acid and its derivatives in various solvents, a standard solubility curve of various concentration of betulonic acid in chloroform (Table 4) versus corresponding peak area from gas chromatogram was generated.

TABLE 4

Standard Solubility Curve of Betulonic Acid in Chloroform

| Concentration of BA (mol/L) | Concentration of BA (mg/mL) | Peak Area ($\times 10^{-4}$) |
|---|---|---|
| 0.5 | 227 | 286.5 |
| 0.25 | 113.5 | 78.0 |
| 0.125 | 56.8 | 46.8 |
| 0.0625 | 28.4 | 51.4 |
| 0.01 | 4.5 | 17.4 |
| 0.005 | 2.3 | 5.3 |
| 0.001 | 0.5 | 9.5 |

Figure 5:
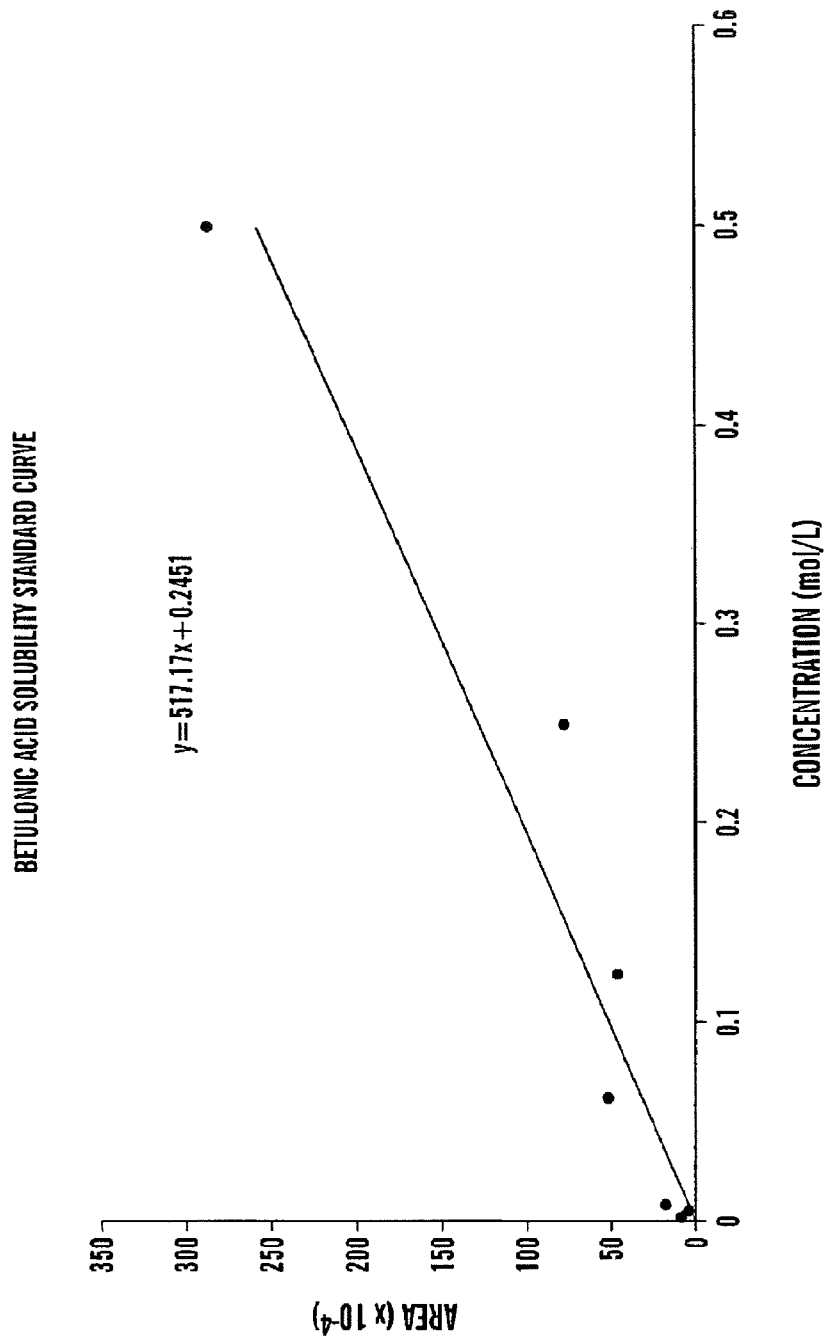
FIG. 5 is a graph showing the standard solubility curve of betulonic acid concentration versus peak area.

8 µL of each known concentration of betulonic acid and solution with unknown concentration were analyzed by gas chromatography ("GC"). The standard solubility curve of betulonic acid concentration versus peak area is shown in FIG. 5. Solvents containing unknown concentration of betulonic acid were evaporated. The residue was dissolved in chloroform analyzed on GC. The concentration of betulonic acid unknown concentration was determined from the standard curve by using the corresponding peaks in the chromatogram.

The standard solutions of betulonic acid were prepared as follows. 45.4 mg of betulonic acid was dissolved in 200 µL neat chloroform to yield 0.5 mol/L concentration of betulonic acid. After three times of double dilution, three different known concentrations (0.25 mol/L, 0.125 mol/L, and 0.0625 mol/L) of betulonic acid were obtained. 2.27 mg of betulonic acid was dissolved in 500 µL neat chloroform to yield 0.01 mol/L concentration of betulonic acid. Double dilution of this solution generated a 0.005 mol/L concentration of betulonic acid. 0.227 mg of betulonic acid was dissolved in 500 µL neat chloroform to yield 0.001 mol/L concentration of betulonic acid.

Example 12

Solubility of Betulonic Acid and Its Derivatives in DMSO Diluted with Culture Medium 3 mg of betulonic acid was dissolved in 200 µL of neat DMSO. Betulonic acid solution in neat DMSO was then diluted with culture medium containing 10% Fetal Bovine Serum ("FBS") to yield a 1% concentration of DMSO to obtain a $1 \times 10^{-3}$ mol/L (0.5 mg/mL) concentration of betulonic acid. Since the betulonic acid was not completely dissolved, suspension was centrifuged at 10,500 rpm for 5 min.

The concentration of betulonic acid in the precipitate and the supernatant was determined from a standard solubility curve. Only 0.4 mg out of 3 mg of betulonic acid was dissolved. The remaining 2.6 mg of betulonic acid was precipitate. Hence, 13% betulonic acid was completely soluble.

Since 1% DMSO in culture medium was not sufficient to solubilize 3 mg of betulonic acid, the concentration of DMSO in culture medium was increased stepwise to completely dissolve betulonic acid. Results of this stepwise increase of DMSO experiment are set forth in Table 5.

TABLE 5

Results of Stepwise Increase in DMSO Concentration Experiment

| | 1 | 2 | 3 | 4 |
|---|---|---|---|---|
| BA (mg) | 0.5 | 0.5 | 0.5 | 0.5 |
| Vol. of Neat DMSO to dissolve BA (µL) | 33 | 103 | 153 | 220 |
| Vol. of Culture Medium (mL) | 1.07 | 1.0 | 0.95 | 0.88 |
| Total Vol. After dilution (mL) | 1.1 | 1.1 | 1.1 | 1.1 |
| Con. of BA (mg/mL) | 0.5 | 0.5 | 0.5 | 0.5 |
| Con. of BA (mol/L) | $1 \times 10^{-3}$ | $1 \times 10^{-3}$ | $1 \times 10^{-3}$ | $1 \times 10^{-3}$ |
| % of DMSO in total Vol. | 3% | 9% | 14% | 20% |
| State of solution | Suspension | Suspension | Cloudy | Clear Solution |

It is shown in Table 5, that 220 µL neat DMSO diluted to 20% with the culture medium was able to dissolve 0.5 mg betulonic acid and its derivatives completely to yield a clear solution.

Each solution of betulonic acid and its derivatives was lyophilized and extracted with ethyl ether. Ethyl ether was then evaporated. The residue containing betulonic acid and/or its derivatives were re-dissolved in chloroform and analyzed on GC. Concentration of drug in the above solutions was analyzed by GC and determined from the standard solubility curve. The concentration of betulonic acid and/or its derivatives in 20% DMSO in culture medium was calculated as shown in Table 6.

TABLE 6

Concentration of BA or Derivatives in 20% DMSO

| | Amount of drug (mg) | Volume of Culture Medium containing 20% DMSO (mL) | Concentration of drug (mg/mL) | Concentration of drug (mol/L) |
|---|---|---|---|---|
| Boc-Monomer | 1.0 | 1.5 | 0.7 | $1 \times 10^{-3}$ |
| Boc-Dimer | 1.0 | 1.6 | 0.6 | $5 \times 10^{-4}$ |
| Boc-Tetramer | 1.0 | 1.7 | 0.6 | $2.5 \times 10^{-4}$ |

The concentrations of betulonic acid determined by GC were close to the calculated values (Table 7), thus confirming that most of betulonic acid and/or its derivatives were completely solubilized.

TABLE 7

Calculated Concentration Values of Betulonic Acid and Derivatives

| | 1 | 2 | 3 | 4 |
|---|---|---|---|---|
| Compound name | Betulonic Acid | Boc-Monomer | Boc-Dimer | Boc-Tetramer |

TABLE 7-continued

Calculated Concentration Values of Betulonic Acid and Derivatives

| | 1 | 2 | 3 | 4 |
|---|---|---|---|---|
| Con. in culture medium containing 20% DMSO (mol/L) | $1 \times 10^{-3}$ | $1 \times 10^{-3}$ | $5 \times 10^{-4}$ | $2.5 \times 10^{-4}$ |
| Con. of betulonic acid portion (mol/L) | $1 \times 10^{-3}$ | $1 \times 10^{-3}$ | $1 \times 10^{-3}$ | $1 \times 10^{-3}$ |
| Total Volume (mL) | 1.4 | 0.75 | 0.75 | 0.93 |
| Chloroform (μL) | 100 | 100 | 100 | 100 |
| Area of GC spectrum ($\times 10^{-4}$) | 6.9 | 4.0 | N/A | 3.7 |
| Cal. Con. of betulonic acid (mol/L) | $0.92 \times 10^{-3}$ | $0.97 \times 10^{-3}$ | N/A | $0.72 \times 10^{-3}$ |

These experiments provided accurate solubility of the compounds in DMSO in culture medium for in vitro cytotoxicity assay.

Example 13

Solubility of Betulonic Acid in Ethanol and Culture Medium

Ethanol was chosen as a biocompatible solvent for use in in vivo studies. Up to 43.3 mg of betulonic acid was completely dissolved in 1 mL of neat (100%) ethanol to yield a saturated solution. This solution can be diluted with culture medium to yield 0.8 mg of betulonic acid completely dissolved in 1.76 mL of culture medium containing 10% human serum with 10% ethanol concentration to generate a concentration of $1 \times 10^{-3}$ mol/mL (0.5 mg/mL) of betulonic acid.

Example 14

Solubilization of Betulonic Acid in Phosphate Buffered Saline (PBS) Containing Human γ-Globulin, Human Albumin and Ethanol Human γ-Globulin and human albumin are two major biocompatible components in human serum. Betulonic acid was dissolved in neat ethanol and diluted with PBS containing various concentrations of γ-globulin and Albumin (Table 8).

TABLE 8

Dilution of BA with PBS at Various Concentrations

| Betulonic Acid (mg) | Ethanol (μL) | Human γ-globulin (27 mg/mL in PBS) (mL)* | Human Albumin (42 mg/mL in PBS) (mL)* | Con. (mol/L) | Observation |
|---|---|---|---|---|---|
| 1.3 | 280 | 2.50 | 0 | $1 \times 10^{-3}$ | Suspension |
| 1.0 | 220 | 1.48 | 0.49 | $1 \times 10^{-3}$ | Cloudy |
| 1.5 | 330 | 1.48 | 1.48 | $1 \times 10^{-3}$ | Little Cloudy |
| 1.4 | 308 | 0.69 | 2.07 | $1 \times 10^{-3}$ | Almost Clear |
| 1.6 | 352 | 0.32 | 2.85 | $1 \times 10^{-3}$ | Clear Solution |
| 1.3 | 280 | 0 | 2.50 | $1 \times 10^{-3}$ | Complete Clear |

*Percentage of human γ-globulin or human albumin in PBS is the same as in human serum.

As shown in Table 8, betulonic acid could be dissolved in PBS with increasing concentration of human albumin. It was completely dissolved in human albumin PBS solution with 10% ethanol to yield a $1 \times 10^{-3}$ mole/L concentration of betulonic acid.

Example 15

Solubility of Betulonic Acid in Human Serum

Betulonic acid dissolved in neat ethanol was diluted with neat human serum to sustain it in solution as shown in Table 9.

TABLE 9

BA Dissolved in Neat Ethanol Diluted with Human Serum

| Betulonic Acid (mg) | Vol. of Ethanol (μL) | Vol. of Human Serum (μL) | Total volume (mL) | Con. of Betulonic Acid (mol/L) | Con. of Betulonic Acid (mg/mL) | Observation |
|---|---|---|---|---|---|---|
| 1.34 | 31 | 700 | 731 | $4 \times 10^{-3}$ | 1.8 | Clear Solution |

The results of Table 9 show that 1.34 mg betulonic acid was dissolved in 31 µL neat ethanol and diluted with human serum to yield a 4.2% final concentration of ethanol and a $4 \times 10^{-3}$ mol/L concentration of drug. The compounds remained soluble and are suitable for in vivo studies. Thus, improvements in the solubility of betulonic acid and its derivatives in biocompatible medium have been achieved.

In addition, betulonic acid and its lysinated derivatives may be completely dissolved in neat ethanol and diluted with PBS containing 4% human albumin (similar to the concentration of albumin in human serum) to achieve a final concentration of 10% ethanol to yield a $1 \times 10^{-3}$ mol per liter concentration of betulonic acid. The results of in vitro studies are consistent with previous results. In in vivo study, solubilized betulonic acid and monomer-Boc at a final concentration of 22% ethanol and 2×10−3 mol per liter of betulonic acid are well tolerated by mice with prostate cancer cell xenografts.

Addition of 10% glycerol further facilitated betulonic acid and its derivatives in solution for extended periods of time.

Example 16

Preparation of Cell Samples

Human T-B hybridoma cell line 174XCEM was exposed to a low multiplicity of infection ("MOI") (MOI=1.0) of stock HIV-1 IIIB isolate for 2 hours at 37° C., washed ×3 with phosphate buffered saline ("PBS"), then plated at 250,000 cells/well in the presence of various agents, shown in Table 10. Dimethyl sulfoxide ("DMSO") buffer was used as a "no virus" control. A commercially available synthetic peptide, thrombospondin peptide ("TSP"), known as having HIV-1 inhibitory activity, was used as an "inhibitory activity" control. Two HIV isolates were used, a patient isolate ("child HIV"), and the standard CXCR4 co-receptor utilizing isolate IIIB.

TABLE 10

Test Agents

| Agent | Concentration |
| --- | --- |
| TSP peptide ("control") | 1 µg/ml |
| betulinol ("OL") | 1 µg/ml (in DMSO) |
| betulonic acid ("BOA") | 1 µg/ml (in DMSO) |
| 3-acetoxy betulin ("BL") | 1 µg/ml (in DMSO) |
| betulin dimethyl ether ("BDE") | 1 µg/ml (in DMSO) |
| 28-acetoxy betulin ("BU") | 1 µg/ml (in DMSO) |
| betulone aldehyde ("AL") | 1 µg/ml (in DMSO) |
| betulin diacetate ("BA") | 1 µg/ml (in DMSO) |

Example 17

Assay for HIV-1 Inhibitory Effect

The assay methods described herein are known in the art, and are described in detail, for example, in Crombie et al., *J. Exp. Med.* 187:25-35 (1998), which is hereby incorporated by reference in its entirety.

Cultures were maintained in culture medium (RPMI-1640+10% fetal bovine serum ("FBS")) for 4 days, the culture supernatants were then collected, lysed with Triton®-X 100 surfactant, and HIV-1 gag (p24) antigen activity assessed by a standard technique, the Antigen Capture ELISA (enzyme-linked immunosorbent assay) (Roche-NEN).

Figure 6:
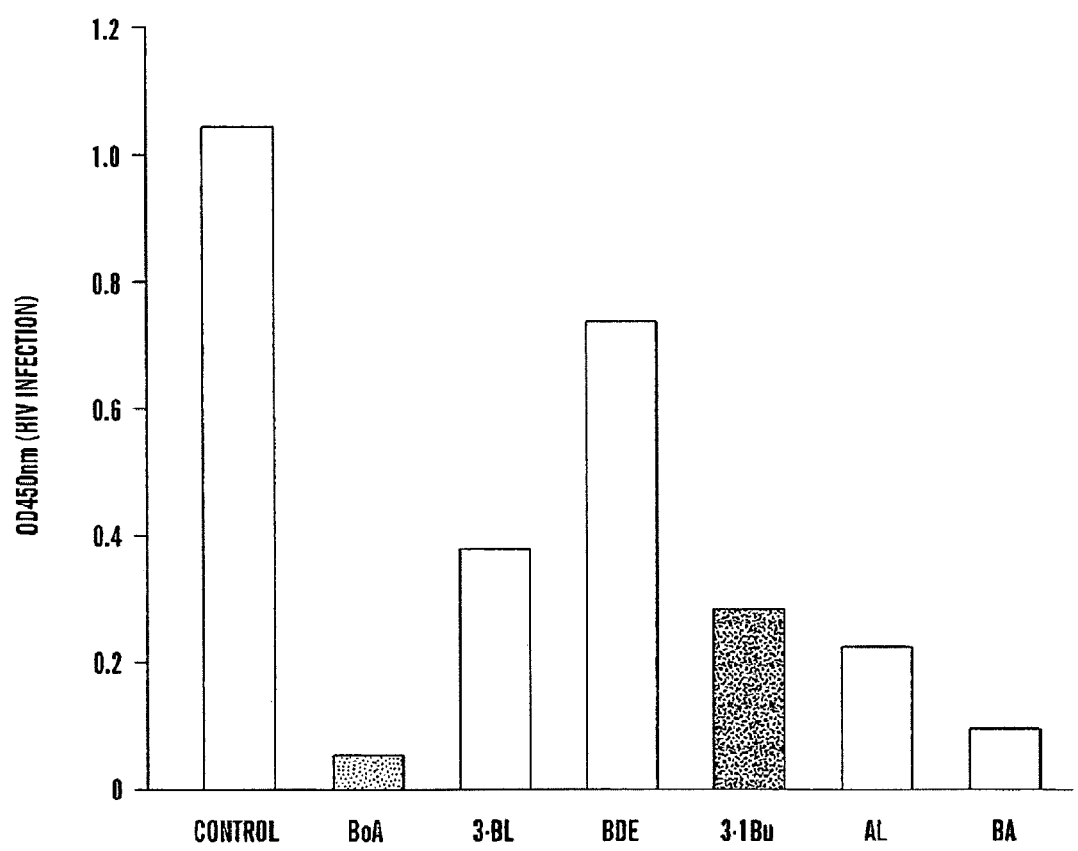
FIG. 6 is a graphic representation of the HIV inhibitory effect of various betulinol derivatives.

Results are shown in FIG. 6. Data are presented in optical density ("OD") units, which are linear with ng/ml of p24 Ag from 0.15 to 1.5 OD, and can be converted to pg/ml of HIV-1 antigen using a standard curve. (Note that the "no virus" DMSO control had an OD reading<0.05, and is not shown in FIG. 6; "control" represents the "inhibitory effect" control, TSP peptide).

Surprisingly, as is clearly seen from FIG. 6, betulin dimethyl ether (BDE), 3-acetoxy betulin (BL) and 28-acetoxy betulin (BU), provide anti-HIV-1 activity superior to that previously disclosed in the art for other betulinol derivatives. The anti-HIV activity of betulonic acid and betulin diacetate has previously been disclosed, for example, in U.S. Pat. No. 6,172,110 to Lee et al., which is hereby incorporated by reference in its entirety. The anti-HIV activity of betulone aldehyde has previously been disclosed, for example, in U.S. Pat. Nos. 5,869,535 and 6,225,353 to Pezzuto et al., which are hereby incorporated by reference in their entirety.

Example 18

Effect on Cell Viability

The cell samples were assessed by trypan blue dye exclusion at four days and seven days. Unlike prior art betulin derivatives, such as, for example, betulonic acid, betulin dimethyl ether, 3-acetoxy betulin, and 28-acetoxy betulin had no effect on total cell number or cell viability.

Example 19

Anti-HIV-1 Effect

Figure 7:
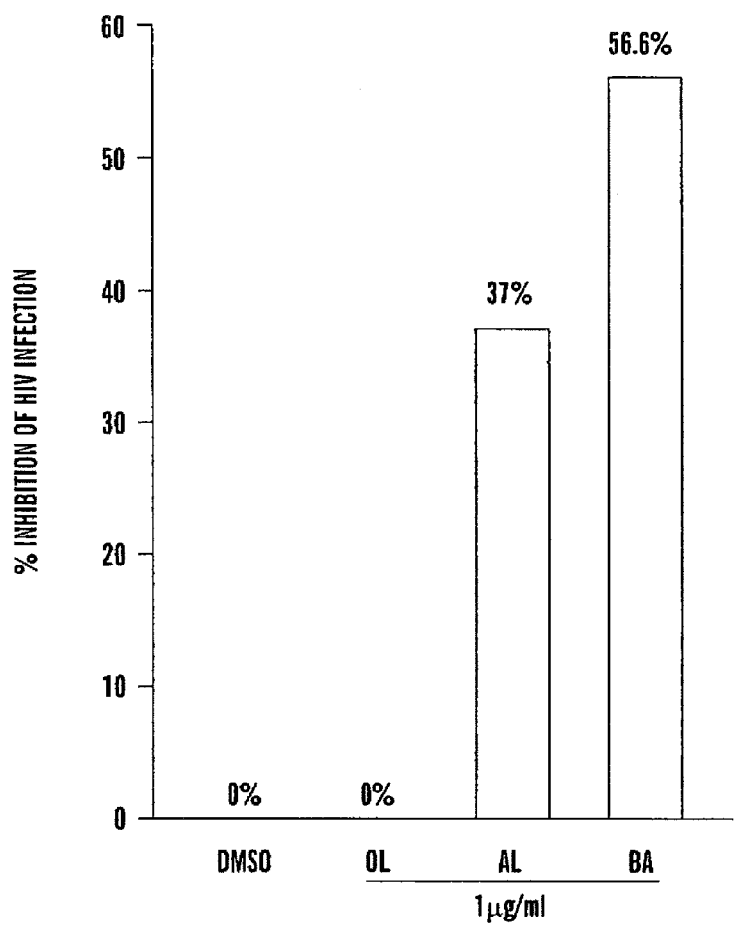
FIG. 7 is a graphic representation of % inhibition of HIV infection by certain betulinol derivatives.

The known anti-HIV-1 inhibitory peptide thrombospondin (TSP), produced 92% inhibition. The DMSO control and OL showed no effect. As shown in FIG. 7, betulone aldehyde (AL) showed 37% inhibition and betulin diacetate (BA) showed 57% inhibition.

Example 20

Dose Dependent Anti-HIV-1 Effect

Figure 8:
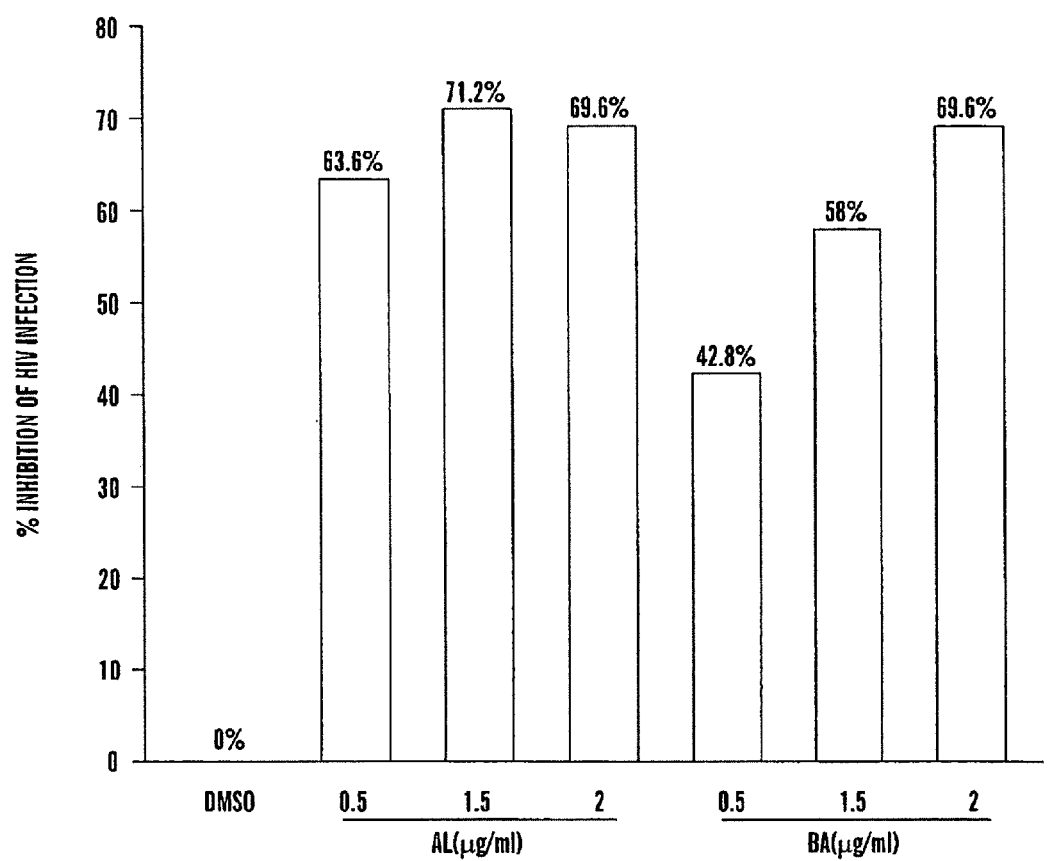
FIG. 8 is a graphic representation of % inhibition of HIV infection by varying doses of certain betulinol derivatives.
Figure 9:
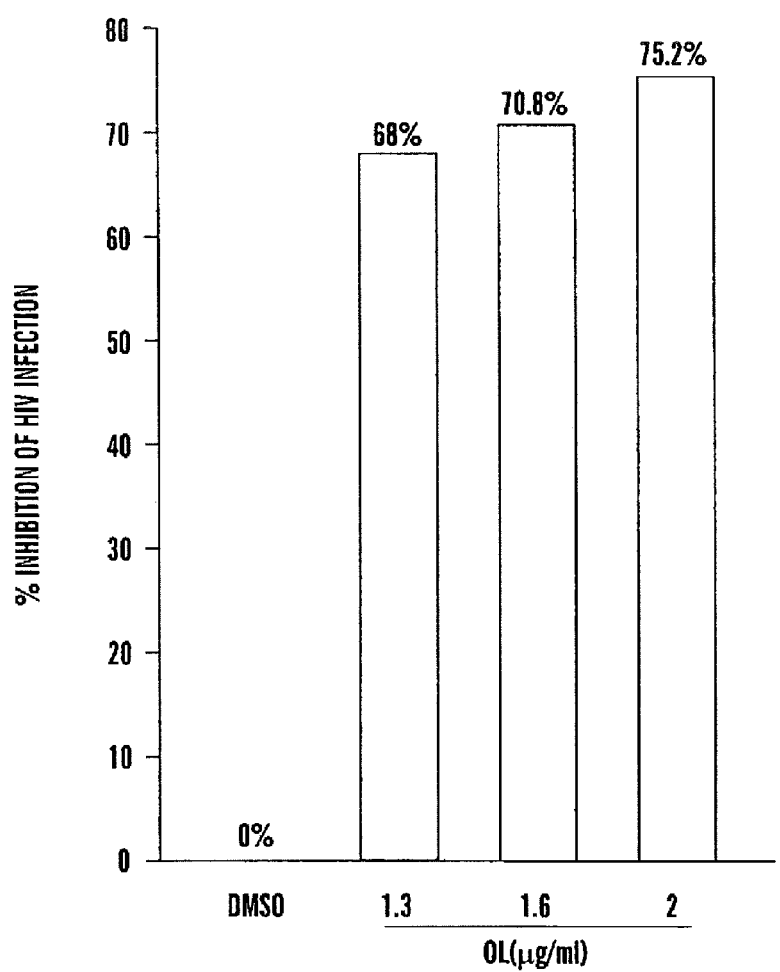
FIG. 9 is a graphic representation of % inhibition of HIV infection by varying doses of betulinol.
Figure 10:
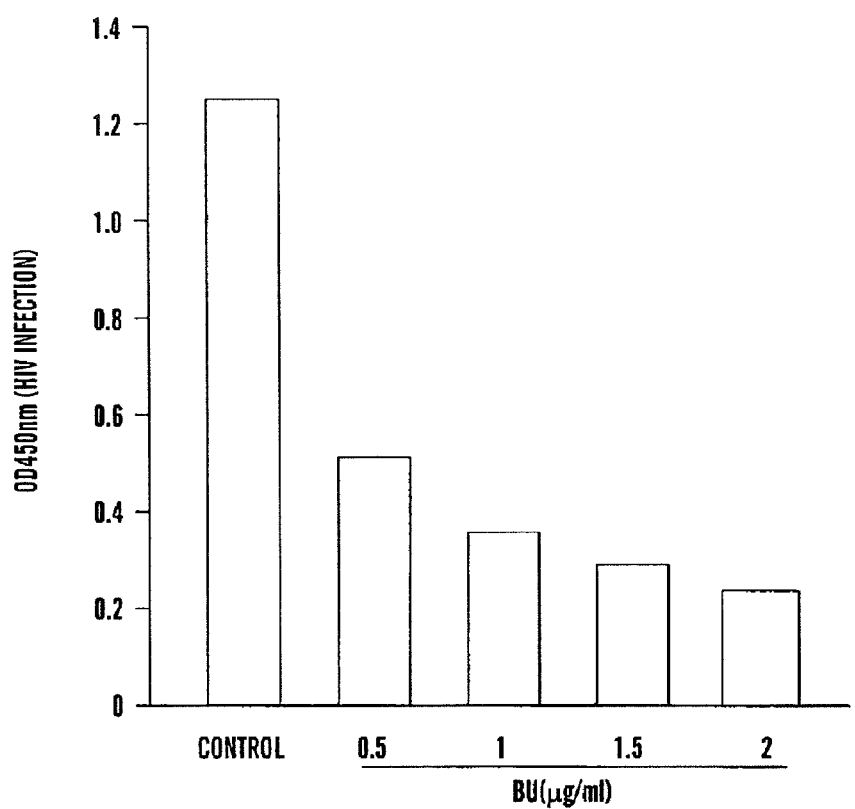
FIG. 10 is a graphic representation of HIV inhibitory effect of varying doses of 28-acetoxy betulin.

As illustrated in FIG. 8, betulone aldehyde (AL) and betulin diacetate (BA) were tested for dose-related effects, with doses of 0.5, 1.5, and 2 µg/ml. Progressive increases in anti-HIV effect were shown, again without cell toxicity. As illustrated in FIG. 9, varying doses of the parental compound betulinol (OL) (1.3, 1.6, and 2 µg/ml) showed increasing anti-HIV effect. As illustrated in FIG. 10, varying doses of 28-acetoxy betulin (BU) (0.5, 1, 1.5, and 2 µg/ml) showed comparable anti-HIV-1 activity. Doses higher than 2 µg/ml could not be used, because the concentration of the vehicle used to dissolve these agents (DMSO) would be too high for the present culture system.

Example 21

Effect on 174XCEM Cells Chronically Infected with Another HIV-1 Isolate

Agents were also evaluated for an effect on 174XCEM cells chronically infected with another HIV-1 isolate. In this system, the standard anti-HIV TSP peptide had no effect. Betulinol and betulone aldehyde had minimal effect. Betulin diacetate showed 20% inhibition at the single dose tested at 1 µg/ml. Although the degree of activity seen in this experiment with chronically infected cells is modest, it should be noted that no current anti-HIV agent, with the exception of α-inteferon, has any effect on release of virus from a chronically infected cell.

Example 22

Comparison of Anti-HIV-1 Activity of Betulinol Derivatives with Known HIV Inhibitors Viral isolates: standard HIV-1 lab isolate IIIB, highly sensitive to all known anti-HIV compounds, and two patient isolates obtained from Haiti, with varying degrees of anti-HIV drug sensitivity.

Target cells: CD4+ Jurkat and CEM-SS human T lymphoblasts, were grown in culture medium (RPMI 1640 plus 10% heat-inactivated FBS). Human peripheral blood mononuclear cells ("PBMC") were derived from heparinized venous blood by density gradient centrifugation using Ficol-paque (Amersham-Pharmacia). For HIV infections, PBMCs were pre-activated with 1 µg/ml phytohemagglutinin ("PHA") and 32 U/ml interleukin-2 ("IL-2") for 2-3 days prior to exposure to HIV-1.

HIV infection: HIV-1 infections were performed as previously described herein. Briefly, 2.5×105 target cells (cell lines or PHA-activated PBMCs) were exposed to stock virus (500 pg of HIV-1 p24 antigen) for 2 h at 37° C., washed twice with PBS, and replated with fresh medium. One half of the culture supernatants were removed from each well every 3-4 days and replaced with fresh medium. At various times after viral inoculation, HIV-1 activity was determined by antigen capture ELISA (Roche-NEN) for HIV-1 p24 gag protein in Triton®-X 100 solubilized culture supernatants, as described.

Drugs: The reverse transcriptase inhibitor AZT and the HIV protease inhibitors ritonavir and nelfinavir were used alone, and in potential synergy experiments with compounds of Formula I. The drugs were added to target cell cultures either before or after the two hour incubation of target cells with virus. AZT was used in concentrations of 0.01-5 µM and the protease inhibitors at concentrations of 0.5-10 µM.

Example 23

Effect of Betulinol Derivatives on HIV-1 RT and Protease, Using Purified Viral Enzymes To evaluate the mechanism of action of compounds of Formula I, direct effects on the two key viral enzymes were measured.

Purified viral enzymes: Reverse transcriptase corresponding to native RT dimer (66 kd/51 kd) purity>98% was obtained from the National Institute of Health ("NIH") AIDS Research and Reference Reagent Program (catalog no. 3555). HIV-1 protease (KIIA, molecular weight 10.7 kd) was obtained from the same source (catalog no. 4375). The protease is identical to wild-type HIV-1 IIIB (HXB2 clone) protease, except for four amino acid substitutions which render it highly resistant to autoproteolysis and oxidative inactivation, making in vitro assays easier.

HIV enzyme assays: HIV RT was assessed by ELISA (Roche-NEN) using the purified enzyme with polyrA/T as substrate and AZT as a positive control, with varying concentrations of compounds of Formula I added. HIV protease was similarly assessed using, as substrate, a 9 amino acid synthetic peptide spanning the p17/p24 junction of HIV gag. Specific activity against this peptide is 12.1 µM/min/mg over 10 min.

Example 24

Effect of Betulinol Derivatives on Cell Proliferation

Compounds of Formula I were evaluated for cellular effects which might indicate toxicity or non-specific antiviral properties. Effects of varying doses of compounds of Formula I on T cell proliferation was assessed by standard methods. In addition, potential induction of apoptosis by these compounds at the anti-HIV doses used, as well as at high concentrations of compounds was assessed.

Apoptosis identification: Levels of apoptosis were assessed by TO-PRO-3 staining (VanHooijdonk, et al., Cytometry 17:185-189 (1994), which is hereby incorporated by reference in its entirety). Briefly, cells were air dried on slides fixed in 4% paraformalydehyde for 10 min. at room temperature, washed with PBS, and treated with 70% EtOH for 15 min. at −20° C. The slides were fixed in a 1:9 solution of acetic acid:ethanol for 1 h, washed, then treated with 2% Triton®X-100 for 2 min., followed by exposure to RNAse A for 20 min. at 4° C. 2-3 drops of a 0.5 µM solution of TO-PRO-3 (Molecular Probes, Invitrogen Life Technologies, Eugene, Oreg.) were added and slides incubated for 10 min. at room temperature in the dark. Slides were then washed, treated with the anti-quenching agent Vectashield (Vector Labs, Inc., Burlingame, Calif.), sealed, and visualized with a fluorescent microscope for evidence of membrane and nuclear integrity.

Example 25

Effect of Betulinol Derivatives on HIV Binding to Target Cells

This is a further investigation of the mechanism of action of compounds of Formula I. It assessed whether these compounds have any membrane-specific properties, interfering with HIV gp120 envelope binding to the two receptors for the virus, CD4 and co-receptor (CXCR4 or CCR5).

HIV envelope proteins: Recombinant HIV-1 gp120 of CXCR4 phenotype (obtained from NIH AIDS Program, described above) and CCR5 phenotype were used.

Cell targets: T cell targets bearing HIV co-receptors and CD4 (CEM-T) or co-receptors but no CD4 (CEM-SS) were utilized. Different target cells bearing CXCR4 but not CCR5 (M07E) were also used.

Cell surface SDF-1/gp120 binding assays: Binding of HIV envelope to CXCR4 and its competition with SDF-1 was assessed by a very sensitive fluorescence binding assay. This involved oligomeric X4 gp160, representing multimers of gp120 and its non-covalently bound transmembrane portion, gp41. This type of assay is necessitated by the low affinity of the gp120-CXCR4 interaction in vitro, as contrasted with gp120 binding to its alternate chemokine receptor CCR5 (Lin et al., J. Virol. 77:931-942 (2003), which is hereby incorporated by reference in its entirety). Detailed methods, including demonstration of specificity and CD4 independence of the binding assay, have been published (Staudinger et al., Biochem. Biophys. Res. Comm. 280:1003-1007 (2001); Bandres et al., J. Virol, 72:2500-2504 (1998), which are hereby incorporated by reference in their entirety).

Varying concentrations of oligomeric X4 gp160 were added for 1 h at 37° C. to target cells. The cells were then washed and incubated with 10 µg/ml of human mAb 1331A, specific for the C terminus of gp120, or with a human mAb against the HIV-1 core protein p24 as a control, both conjugated to phycoerythrin ("PE"), and fluorescence intensity assessed. Displacement of a fixed amount of oligomeric viral envelope, as detected by the human anti-gp120 mAb, by increasing amounts of compounds of Formula I were examined. Positive controls for CD4 (monoclonal antibody) CXCR4 (SDF-1, 500 to 1500 ng/ml), and CCP5 (1500 ng/ml RANTES) were included.

Example 26

Effect of Betulinol Derivatives on HIV Promoter (TR)-Driven Transcription

The effects of compounds of Formula I on HIV promoter (LTR)-driven transcription, emphasizing HIV-1 Tat and NPκB activity was evaluated. Plasmid constructs, plasmid transfections and reporter assays: The reporter plasmid pC15CAT (Arya et al., *Science* 229:69-73 (1985), which is hereby incorporated by reference in its entirety) contains sequences for SV40 regulatory genes, bacterial chloramphenical acetyl transferase ("CAT"), and the HIV-1 long terminal repeat ("LTR"). The HIV-1 tat plasmid pCV-1 (Arya et al., *Science* 229:69-73 (1985), which is hereby incorporated by reference in its entirety) contains a 1.8 kb cDNA fragment encompassing both exons of tat. For transfections, cells were washed with serum-free RPMI-1640, and $2\times10^6$ cells per condition are resuspended in 1 ml of Optimum media (Gibco, Life Technologies, Gaithersburg, Md.) along with 2-6 μg plasmid DNA and DMRIE-C transfection reagent (Gibco, Life Technologies, Gaithersburg, Md.). Cells were incubated at 37° C. for 5 h, and fresh RPMI 1640 containing 10% FBS added. 36 h after transfection, select samples were treated with compound. CAT assays were performed using a kit (Roche), as per the manufacturer's directions.

Electrophoretic Mobility Shift Assay ("EMSA"): This is a standard assay for assessing NFκ activity. Target cells were exposed to compounds of Formula I alone, in the presence of a known NFκB activator (TNF-α), or with HIV-1 for 48 h. Nuclear extracts were then prepared using a Nuclear extract kit (Sigma). 10 μg of nuclear extract was dissolved in a buffer containing 1 ng of 32P-5' end labeled, KB probe, 1 μg of poly(dI-dC), 50 ng of sonicated salmon sperm DNA, 10 mM $MgCl_2$, mM KCl, 1 mM DTT, 12.5 mM HEPES pH 7.8, 10% glycerol, and 0.05% Nonidet p-40. Mixtures were incubated for 15 min. at 4° C. and protein bound DNA complexes were analyzed by electrophoresis on a 6% polyacrylamide gel. Controls include a competition assay with unlabelled κB oligonucleotide added at a 50 fold excess to probe.

Example 27

Determination of the Inhibition of HIV Infection by Betulinol Derivatives using H9 (Lymphoma Cells)

Figure 11:
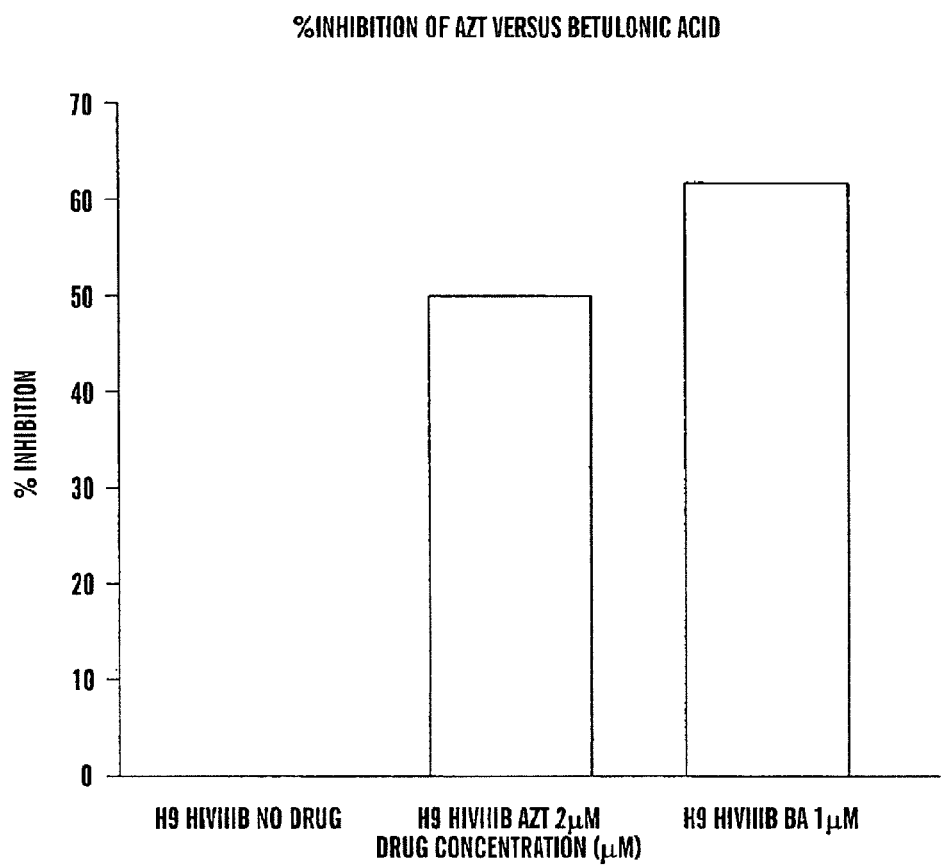
FIG. 11 is a graphic representation of % inhibition of AZT versus betulonic acid of H9 cells infected with HIV-IIIB.

$1.5\times10^5$ of H9 cells were exposed to a stock HIV-1 IIIB isolate (at an MOI of 1.0) at 37° C. for 2 hours, washed 3 times with PBS, and plated out in 1 mL of RPMI media containing 10% FBS in the presence of betulonic acid with or without AZT. On day 3, half of the media (0.5 mL) was replaced with fresh media and appropriate drugs. On day 7, the culture supernatants were collected, solubilized in Triton-X100, and HIV-1 Gag antigen p24 were assessed and presented in optical density ("OD") units using a standard assay (p24 ELISA Kit from Perkin Elmer, Wellesley, Mass.). Results are set forth in FIG. 11. The decrease of OD units represented the drug inhibition effects on HIV infection. This method is from Crombie et al., *J. Exp. Med.* 187:25-35 (1998), which is hereby incorporated by reference in its entirety.

Example 238

Figure 12:
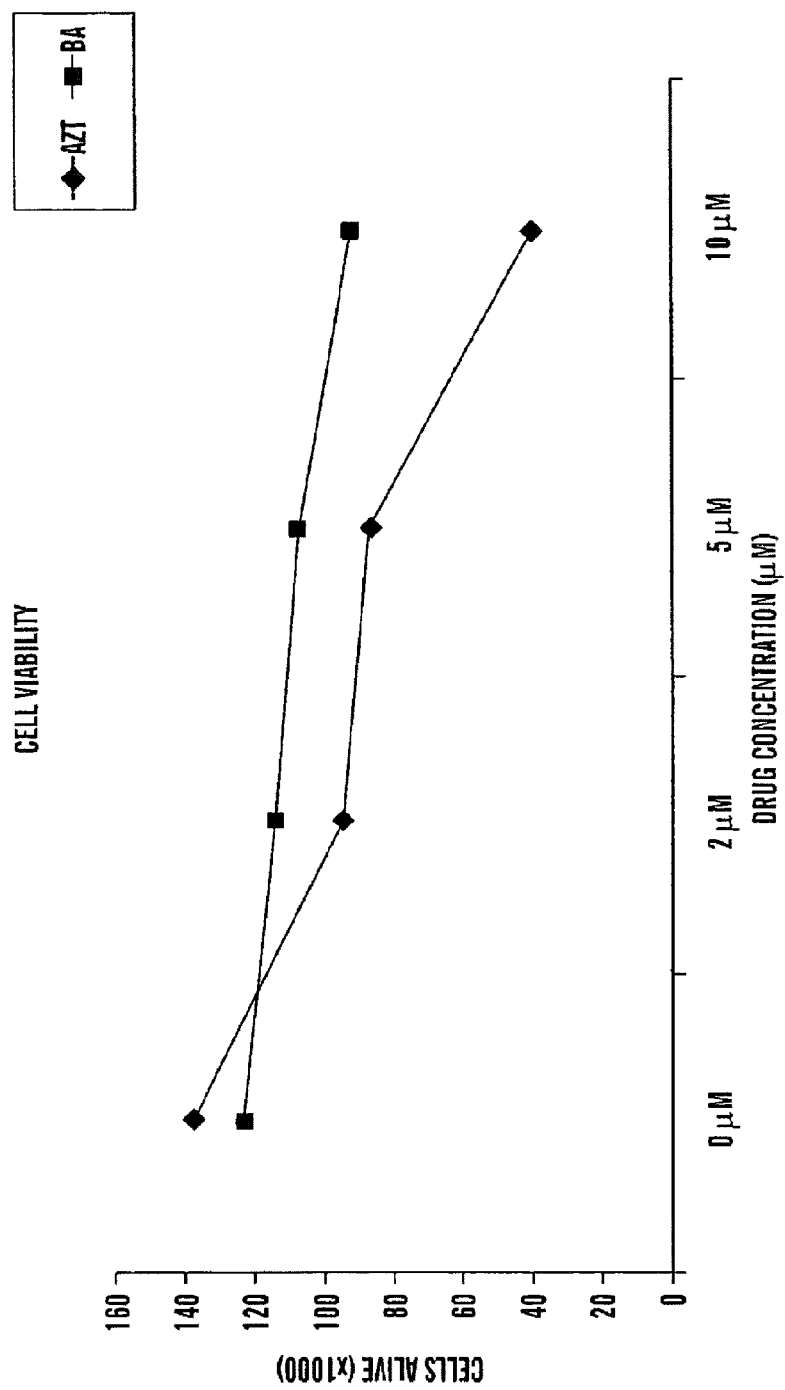
FIG. 12 is a graphical representation of cell viability of H9 (lymphoma) cells in the presence of AZT versus betulonic acid.

Viability of Lymphoma Cells In the Presence of AZT Versus Betulonic Acid $1.5\times10^5$ of H9 (lymphoma) cells were plated in each culture well in 1 mL of RPMI media containing 10% FBS in the presence of 0, 2, 5, 10, and 20 mM of betulonic acid and AZT and incubated at 37° C. On day 3, the drug effects on cell viability were assessed using Trypan Blue Dye Exclusion Assay. Results are set forth in FIG. 12. The data is presented as both living cell counts and percentage. Chemical resources were obtained through Sigma Aldrich.

Example 29

Figure 13:
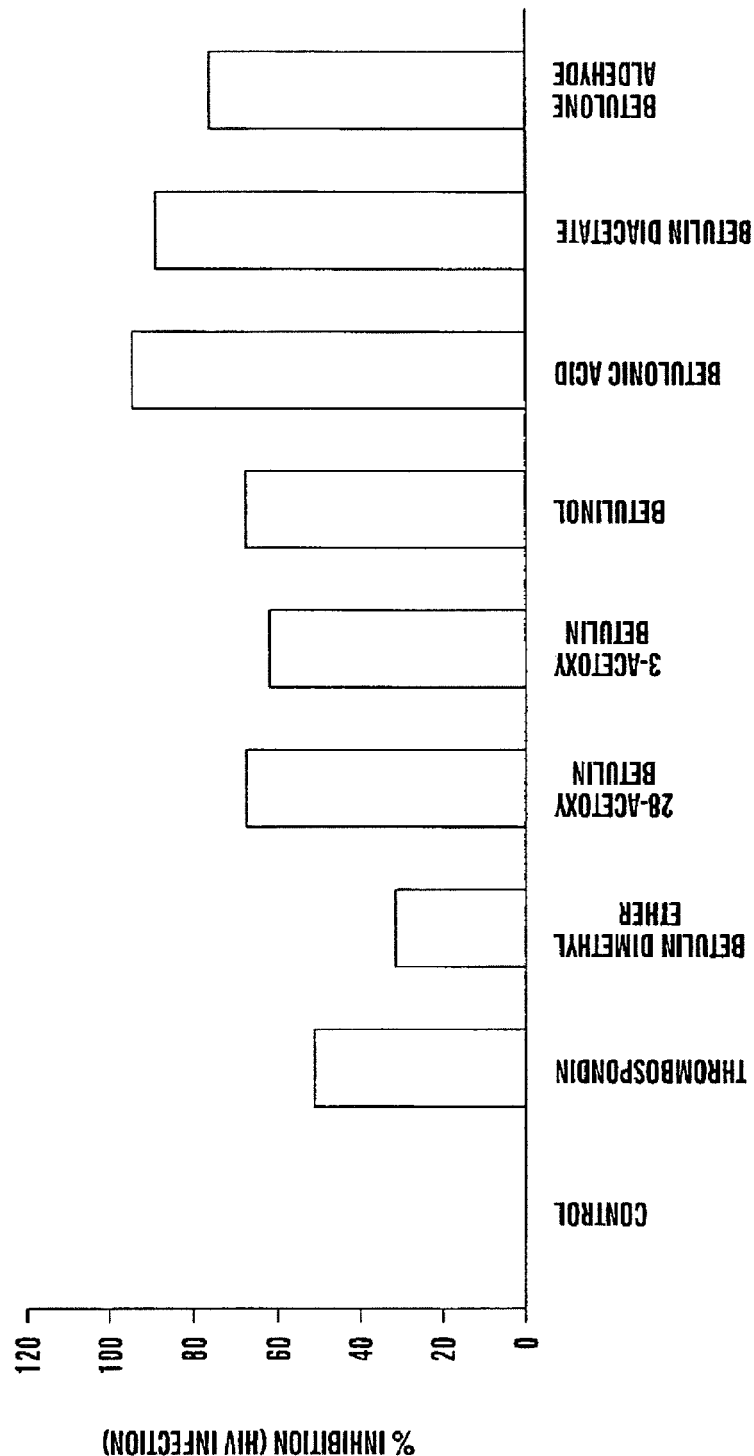
FIG. 13 is a graphical representation of the anti-HIV activity of betulinol derivatives in CEM (CD4+T) cells.

Determination of the Inhibition of HIV Infection by Betulinol Derivatives Using Crombie's Method Acute HIV infection was performed using HIV-1 isolate IIIB stock virus. In brief, CEM (CD4+T) cells ($2.5\times10^5$ target cells) were exposed to stock virus at a MOI of either 0.02 or 0.15 for 2 h at 37° C., washed twice with PBS, and replated in tissue culture microwells with 0.3 ml of fresh culture medium. Compounds of Formula I dissolved in DMSO were added into the culture and were tested for anti-HIV activity with reference to thrombospondin (TSP), a known anti-HIV drug. Three days after inoculation, one half of culture supernatant from each well was replaced with fresh medium. HIV activity was determined on day seven using an ELISA antigen capture assay for HIV-1 p24 (Gag) core protein (Dupont Medical Products, Boston, Mass.) with Triton X-100 solubilized culture supernatants. Inhibition was calculated as percent of the control. Thrombospondin (TSP) was used at a concentration of 1 mg/mL and yielded an inhibition of 51%. Compounds of Formula I were also used at a concentration of 1 ug/mL. Results are set forth in FIG. 13.

Example 30

Betulonic Acid as Anti-AZT Resistant Compounds

Figure 14:
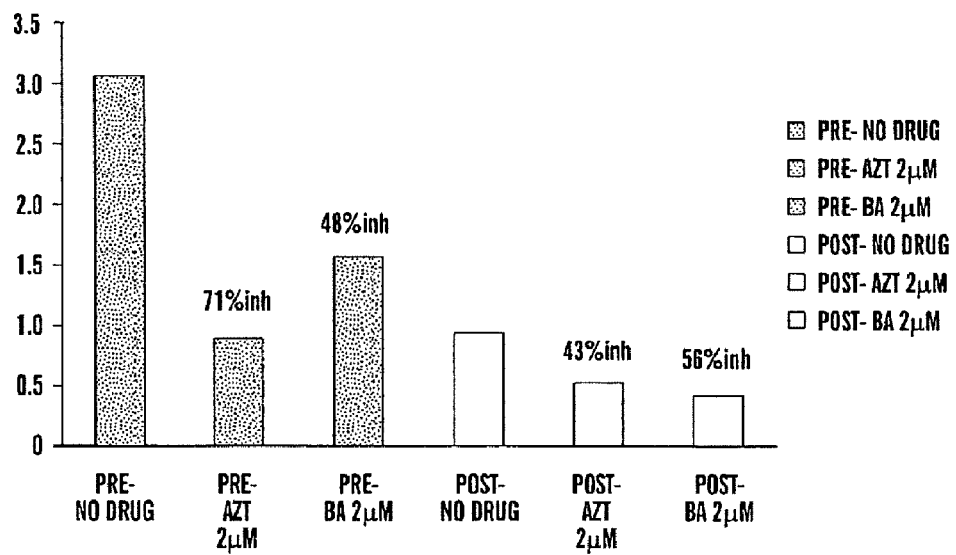
FIG. 14 shows the results of AZT resistance for patients suffering from HIV.
Figure 15:
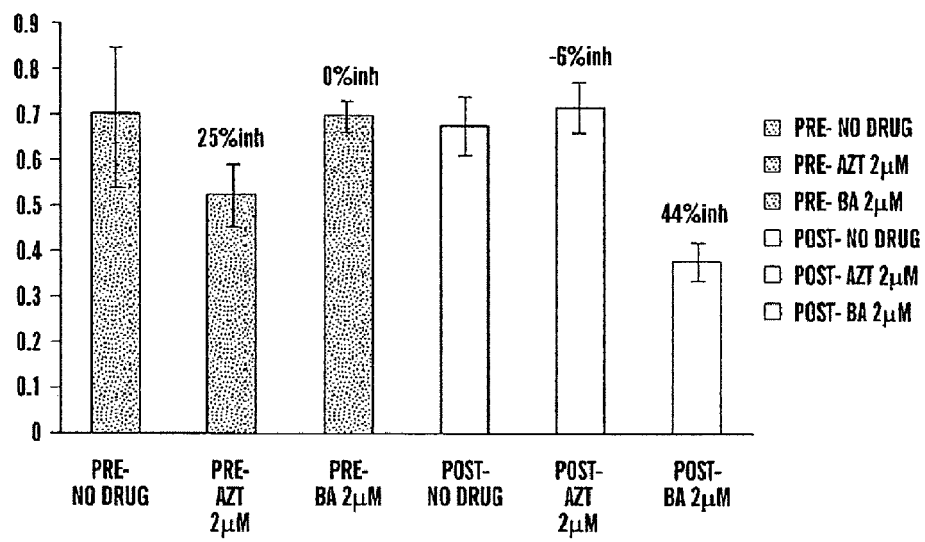
FIG. 15 shows the results of AZT resistance for patients suffering from HIV.

In order to evaluate the anti-HIV activity of betulonic acid and its derivatives, isolates from patients suffering from HIV prior to treatment and following the treatment with AZT were obtained. These isolates were used to infect MT-2 cells in vitro. The results on day 5 (FIG. 14) and day 8 (FIG. 15) indicated that the isolates from patients post-treatment became resistant to AZT. The effect of AZT and betulonic acid on the AZT-resistant strain showed that on day 5 the AZT was ineffective, whereas betulonic acid showed a 44% inhibition in the HIV infection. On day 8, the inhibition with betulonic acid increased further. It is anticipated that other betulinol derivatives like betulinol aldehyde and diacetate and their conjugates, including peptide coupled compounds (e.g., attached via a lysine, histidine, arginine) will yield significantly higher inhibition to AZT-resistant HIV strains.

These results suggest the possibility for treatment of patients who become resistant to AZT or other anti-HIV therapy.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating HIV-1 infection in a subject, said method comprising: administering to a subject with HIV-1 infection a therapeutically effective amount of a compound having the formula

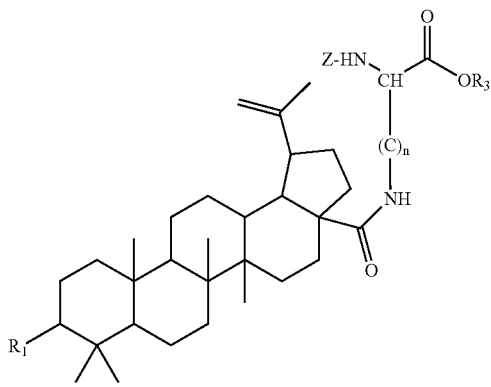

or a pharmaceutically acceptable salt thereof, wherein
$R_1$ is selected from the group consisting of —$CH_3$, =O, —OH, —$OCH_3$, —$OC(O)CH_3$, —NHNH-2,4-Dinitrophenyl, and =S and
$R_3$ is selected from the group consisting of H and $C_1$-$C_5$ alkyl,
n is an integer from 1 to 12; and
Z is H or a protective group.

2. The method according to claim 1, wherein the subject is a mammal.

3. The method according to claim 1, wherein the compound is administered as a tablet in a dosage range of 1 mg-500 mg.

4. The method according to claim 1, wherein Z is selected from the group consisting of butyloxycarbonyl and carbobenzoxy.

5. The method according to claim 1, wherein $R_1$ is =O, $R_3$ is methyl, and n is 4.

6. The method according to claim 1, wherein $R_1$ is =O, $R_3$ is H, Z is —C(=O)—O-t-butyl, and n is 4.

7. The method according to claim 1, wherein $R_1$ is —OH, $R_3$ is H, Z is —C(=O)—O-t-butyl, and n is 4.

8. The method according to claim 1, wherein n is 2-8.

9. The method according to claim 1, wherein said subject has AIDS.

* * * * *